(12) United States Patent
Goto et al.

(10) Patent No.: US 7,569,258 B2
(45) Date of Patent: *Aug. 4, 2009

(54) CHLOROFLUOROBENZENE LIQUID CRYSTAL COMPOUND, LIQUID CRYSTAL COMPOSITION, AND LIQUID CRYSTAL DISPLAY DEVICE

(75) Inventors: Yasuyuki Goto, Tokyo (JP); Teru Shimada, Ichihara (JP); Teruyo Sugiura, Ichihara (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 301 days.

This patent is subject to a terminal disclaimer.

(21) Appl. No.: 11/368,305

(22) Filed: Mar. 3, 2006

(65) Prior Publication Data

US 2006/0198968 A1      Sep. 7, 2006

(30) Foreign Application Priority Data

Mar. 3, 2005   (JP) .............................. 2005-059154

(51) Int. Cl.
C09K 19/30      (2006.01)
C09K 19/12      (2006.01)
C07C 25/13      (2006.01)

(52) U.S. Cl. .............. 428/1.1; 252/299.63; 252/299.66; 570/127; 570/129; 570/131

(58) Field of Classification Search ................. 428/1.1; 252/299.63, 299.66; 570/127, 129, 131
See application file for complete search history.

(56) References Cited

U.S. PATENT DOCUMENTS

| | | | |
|---|---|---|---|
| 5,279,764 A | 1/1994 | Reiffenrath et al. | 252/299.66 |
| 6,025,370 A * | 2/2000 | Todo et al. | 514/312 |
| 6,056,893 A | 5/2000 | Reiffenrath et al. | 252/299.6 |
| 6,329,027 B1 | 12/2001 | Kondo et al. | 428/1.1 |
| 2006/0210725 A1 * | 9/2006 | Fujita et al. | 428/1.1 |
| 2007/0221881 A1 * | 9/2007 | Fujita et al. | 252/299.61 |

FOREIGN PATENT DOCUMENTS

| | | |
|---|---|---|
| DE | 42 19 819 | 12/1993 |
| EP | 0 451 854 | 10/1991 |
| EP | 0 364 538 | 5/1992 |
| EP | 0 959 060 | 11/1999 |

OTHER PUBLICATIONS

Michael Hird et al., "The Synthesis and Transition Temperatures of Some Ortho-Dichloroterphenyls for Ferroelectric Mixtures" Mol. Cryst. Liq. Cryst, 1995, vol. 260, pp. 227-240.

* cited by examiner

Primary Examiner—Shean C Wu
(74) Attorney, Agent, or Firm—J.C. Patents

(57) ABSTRACT

Such a liquid crystal compound is provided that has stability to heat, light and so forth, has a nematic phase in a wide temperature range, has a small viscosity, a suitable optical anisotropy, and suitable elastic constants $K_{33}$ and $K_{11}$ ($K_{33}$: bend elastic constant, $K_{11}$: splay elastic constant), and has suitable negative dielectric anisotropy and excellent compatibility with other liquid crystal compounds. A liquid crystal composition containing the liquid crystal compound, and a liquid crystal display device containing the liquid crystal composition are also provided.

The liquid crystal compound is represented by one of formulas (a) to (d), the liquid crystal composition contains the liquid crystal compound, and the liquid crystal display device contains the liquid crystal composition:

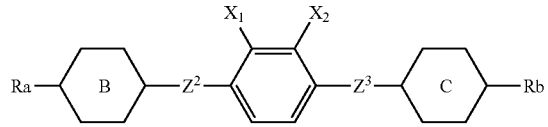

(a)

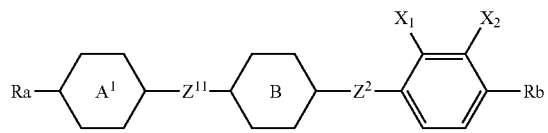

(b)

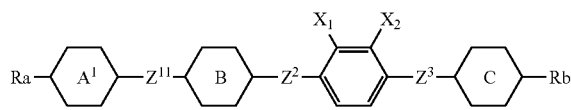

(c)

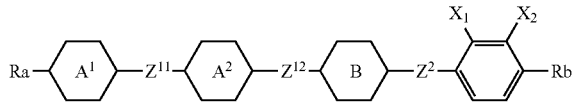

(d)

wherein Ra and Rb are independently linear alkyl or linear alkoxy, rings $A^1$, $A^2$, B and C are independently trans-1,4-cyclohexylene or 1,4-phenylene, $Z^{11}$, $Z^{12}$, $Z^2$ and $Z^3$ are independently a single bond or alkylene, and one of $X_1$ and $X_2$ is fluorine, and the other thereof is chlorine.

14 Claims, No Drawings

CHLOROFLUOROBENZENE LIQUID CRYSTAL COMPOUND, LIQUID CRYSTAL COMPOSITION, AND LIQUID CRYSTAL DISPLAY DEVICE

BACKGROUND OF THE INVENTION

1. Field of the Invention

The present invention relates to a liquid crystal compound, a liquid crystal composition, and a liquid crystal display device. More specifically, the invention relates to a chlorofluorobenzene derivative, which is a liquid crystal compound, a liquid crystal composition containing the compound and having a nematic phase, and a liquid crystal display device containing the composition.

2. Related Art

A liquid crystal display device utilizes optical anisotropy and dielectric anisotropy inherent to a liquid crystal compound (which means, in the invention, a generic term for a compound having a liquid crystal phase such as a nematic phase, a smectic phase and so forth, and also for a compound having no liquid crystal phase but being useful as a component of a composition). On a liquid crystal display device, various modes including a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, and so forth.

Among these operation modes, an ECB mode, an ISP mode, a VA mode and so forth are operation modes utilizing vertical orientation of liquid crystal molecules, and it has been known that in particular an IPS mode and a VA mode are capable of improving the narrow viewing angle, which is a problem of the conventional display modes, such as a TN mode, an STN mode and so forth.

As a component of a liquid crystal composition having a negative dielectric anisotropy capable of being used in a liquid crystal display device of these operation modes, a large number of such liquid crystal compounds have been investigated that hydrogen on a benzene ring is replaced by fluorine (see, for example, JP H2-503441 A/1990 and JP H02-4725 A/1990).

For example, a compound (A) represented by the following structural formula has been investigated (see, for example, JP H2-503441 A/1990). However, a compound, in which hydrogen on a benzene ring is replaced by fluorine, represented by the compound (A) is poor in compatibility with other compounds in a low temperature region.

As a compound, in which hydrogen on a benzene ring is substituted by chlorine and fluorine, for example, a compound (B) represented by the following structural formula has been reported (see, for example, WO 98/23561 A/1998). However, the compound (B) does not have a high clear point and has a large viscosity.

As a compound, in which hydrogen on a benzene ring is substituted by chlorine, for example, a compound (C) represented by the following structural formula has been reported (see, for example, Molecular Crystals and Liquid Crystals, vol. 260, pp. 227-240 (1995)). However, the compound (C) has a significantly narrow range (mesomorohic range) where the compound shows liquid crystallinity and has a small negative dielectric anisotropy.

As chiral dopants in liquid-crystalline media for electro-optical displays, for example, a compound (D) represented by the following structural formula has been reported (see, for example, JP H10/158652 A/1998). However, the compound (D) has a significantly narrow range (mesomorphic range) where the compound shows liquid crystallinity.

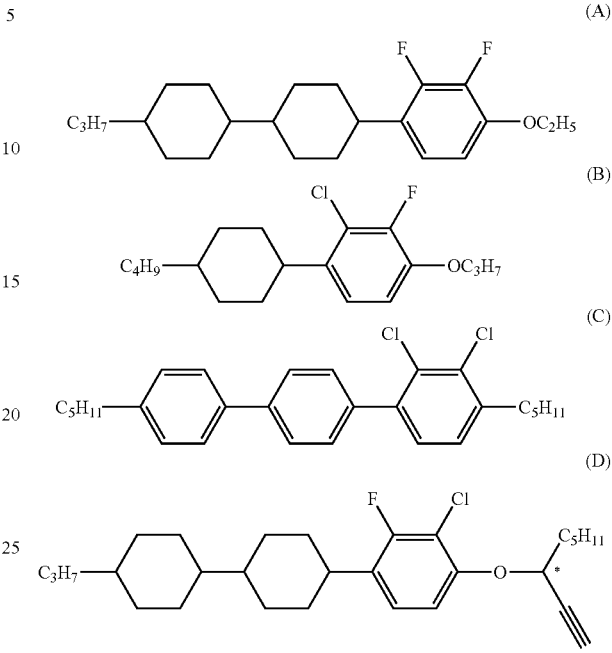

Therefore, a liquid crystal display device having such an operation mode as an IPS mode, a VA mode and so forth still has problems in comparison to CRT, and improvement in response time, improvement in contrast, and decrease in driving voltage are demanded.

The liquid crystal display device driven in an IPS mode or a VA mode is constituted mainly by a liquid crystal composition having a negative dielectric anisotropy, and in order to improve the aforementioned characteristics, a liquid crystal compound contained in the liquid crystal composition is demanded to have the following characteristics (1) to (8). Namely, the compound:

(1) is chemically stable and physically stable,
(2) has high clear point (transition temperature between a liquid crystal phase and an isotropic phase),
(3) has low minimum temperature of a liquid crystal phase (such as a nematic phase, a smectic phase and so forth), particularly a low minimum temperature of a nematic phase,
(4) has small viscosity,
(5) has suitable optical anisotropy,
(6) has suitable negative dielectric anisotropy,
(7) has suitable elastic constants $K_{33}$ and $K_{11}$ ($K_{33}$: bend elastic constant, $K_{11}$: splay elastic constant), and
(8) is excellent in compatibility with other compounds.

In the case where a composition containing a chemically and physically stable compound as in (1) is used in a display device, a voltage holding ratio can be increased.

In the case of a composition containing a liquid crystal compound having a high clear point or a low minimum temperature of a liquid crystal phase as in (2) or (3), the temperature range of a nematic phase can be enhanced, whereby the display device can be used in a wide temperature range.

In the case where a composition containing a compound having small viscosity as in (4) or a compound having suitable elastic constants $K_{33}$ and $K_{11}$ as in (7) is used in a display device, the response time can be improved. In the case where a composition containing a compound having suitable optical anisotropy as in (5) is used in a display device, the display device can be improved in contrast.

A liquid crystal composition containing a liquid crystal compound having a negatively large dielectric anisotropy has low threshold voltage, and therefore, in the case of a display device using a composition containing a compound having suitable negative dielectric anisotropy as in (6), the display device can have a low driving voltage and small electric power consumption. In the case where a composition containing a compound having suitable elastic constant $K_{33}$ as in (7) is used in a display device, the driving voltage of the display device can be controlled, and the electric power consumption thereof can also be controlled.

A liquid crystal compound is generally used as a composition obtained by mixing with other many liquid crystal compounds for exhibiting such characteristics that are difficult to obtain with a sole compound. Therefore, a liquid crystal compound used in a display device desirably has good compatibility with other compounds as in (8). A display device is used in a wide temperature range including temperatures below freezing point in some cases, and therefore, a compound used in the composition desirably has good compatibility in a low temperature range in some cases.

SUMMARY OF THE INVENTION

The invention concerns a liquid crystal compound represented by one of formulas (a) to (d):

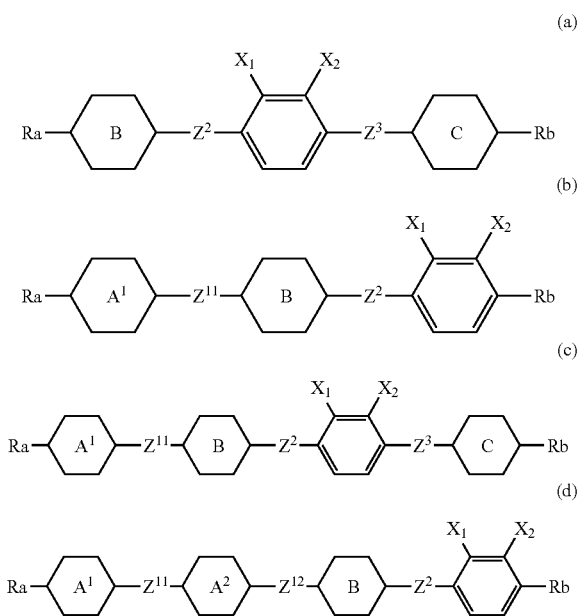

wherein Ra and Rb are independently hydrogen or linear alkyl having 1 to 10 carbons, provided that in the alkyl, —$CH_2$— may be replaced by —O—, —$(CH_2)_2$— may be replaced by —CH=CH—, and hydrogen may be replaced by a halogen; rings $A^1$, $A^2$, B and C are independently trans-1,4-cyclohexylene or 1,4-phenylene; $Z^{11}$, $Z^{12}$, $Z^2$ and $Z^3$ are independently a single bond or alkylene having 2 or 4 carbons, provided that in the alkylene, —$CH_2$— may be replaced by —O— and —$(CH_2)_2$— may be replaced by —CH=CH—; and one of $X_1$ and $X_2$ is fluorine, and the other thereof is chlorine, provided that:

in a case where:
in formula (a), rings B and C are trans-1,4-cyclohexylene, and $Z^2$ and $Z^3$ are a single bond,
in formula (b), rings $A^1$ and B are trans-1,4-cyclohexylene, $Z^{11}$ is a single bond, and $Z^2$ is —$CH_2O$—, and
in formula (d), rings $A^1$, $A^2$ and B are trans-1,4-cyclohexylene, $Z^{11}$ and $Z^{12}$ are a single bond, and $Z^2$ is a single bond or —$CH_2O$—, Rb is one of linear alkoxy having 1 to 9 carbons, linear alkoxyalkyl having 2 to 9 carbons, linear alkenyl having 2 to 10 carbons, linear alkenyloxy having 2 to 9 carbons, linear fluoroalkyl having 1 to 10 carbons, and linear fluoroalkoxy having 1 to 9 carbons.

The invention also concerns a liquid crystal composition comprising the liquid crystal compound.

The invention also concerns a liquid crystal display device comprising a liquid crystal composition comprising the liquid crystal compound.

DETAILED DESCRIPTION

A first object of the invention is to provide such a liquid crystal compound that has stability to heat, light and so forth, has a nematic phase in a wide temperature range, has a small viscosity, a suitable optical anisotropy, and suitable elastic constants $K_{33}$ and $K_{11}$, and has suitable negative dielectric anisotropy and excellent compatibility with other liquid crystal compounds.

A second object of the invention is to provide such a liquid crystal composition containing the liquid crystal compound that has a low viscosity, a suitable optical anisotropy, a suitable negative dielectric anisotropy, a low threshold voltage, a high maximum temperature of a nematic phase (phase transition temperature between a nematic phase and an isotropic phase), and a low minimum temperature of a nematic phase.

A third object of the invention is to provide such a liquid crystal display device containing the composition that has a short response time, a small electric power consumption, a small driving voltage, and a large contrast, and can be used in a wide temperature range.

As a result of earnest investigations on the aforementioned problems made by the inventors, it has been found that:

a liquid crystal compound having a particular structure, in which hydrogen on a benzene ring is replaced by chlorine and fluorine, has stability to heat, light and so forth, has a nematic phase in a wide temperature range, has a small viscosity, a suitable optical anisotropy, and suitable elastic constants $K_{33}$ and $K_{11}$ ($K_{33}$: bend elastic constant, $K_{11}$: splay elastic constant), and has suitable negative dielectric anisotropy and excellent compatibility with other liquid crystal compounds, a liquid crystal composition containing the liquid crystal compound has a low viscosity, a suitable optical anisotropy, a suitable negative dielectric anisotropy, a low threshold voltage, a high maximum temperature of a nematic phase, and a low minimum temperature of a nematic phase, and a liquid crystal display device containing the composition has a short response time, a small electric power consumption, a small driving voltage, and a large contrast, and can be used in a wide temperature range, and thus the invention has been completed.

The invention has the following features:

1. A liquid crystal compound represented by one of formulas (a) to (d):

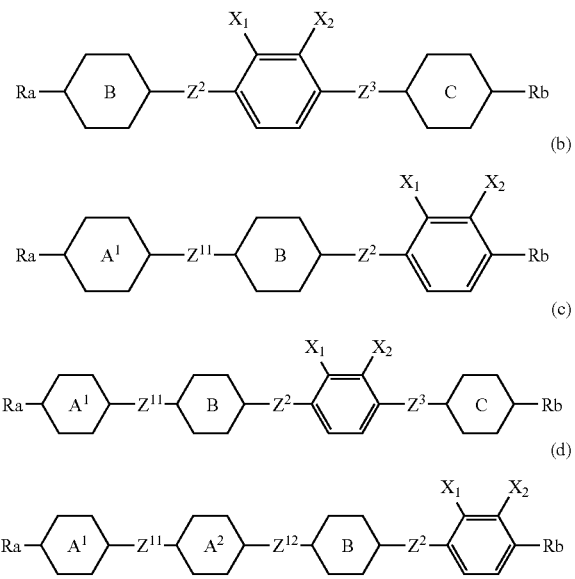

wherein Ra and Rb are independently hydrogen or linear alkyl having 1 to 10 carbons, provided that in the alkyl, —CH$_2$— may be replaced by —O—, —(CH$_2$)$_2$— may be replaced by —CH=CH—, and hydrogen may be replaced by a halogen; rings A$^1$, A$^2$, B and C are independently trans-1,4-cyclohexylene or 1,4-phenylene; Z$^{11}$, Z$^{12}$, Z$^2$ and Z$^3$ are independently a single bond or alkylene having 2 or 4 carbons, provided that in the alkylene, —CH$_2$— may be replaced by —O— and —(CH$_2$)$_2$— may be replaced by —CH=CH—; and one of X$_1$ and X$_2$ is fluorine, and the other thereof is chlorine, provided that:

in a case where:
in formula (a), rings B and C are trans-1,4-cyclohexylene, and Z$^2$ and Z$^3$ are a single bond,
in formula (b), rings A$^1$ and B are trans-1,4-cyclohexylene, Z$^{11}$ is a single bond, and Z$^2$ is —CH$_2$O—, and
in formula (d), rings A$^1$, A$^2$ and B are trans-1,4-cyclohexylene, Z$^{11}$ and Z$^{12}$ are a single bond, and Z$^2$ is a single bond or —CH$_2$O—, Rb is one of linear alkoxy having 1 to 9 carbons, linear alkoxyalkyl having 2 to 9 carbons, linear alkenyl having 2 to 10 carbons, linear alkenyloxy having 2 to 9 carbons, linear fluoroalkyl having 1 to 10 carbons, and linear fluoroalkoxy having 1 to 9 carbons.

2. A liquid crystal compound represented by one of formulas (a-1) to (d-1):

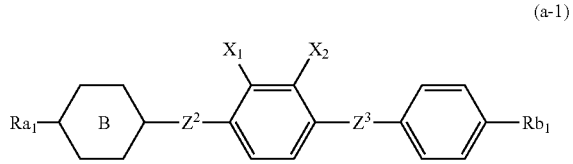

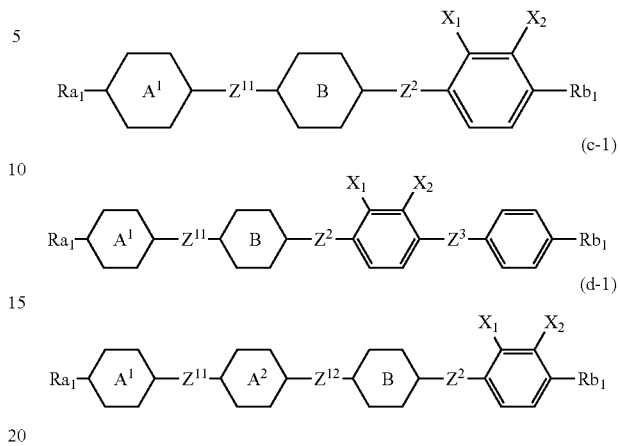

wherein Ra$_1$ and Rb$_1$ are independently linear alkyl having 1 to 10 carbons, provided that in the alkyl, —CH$_2$— may be replaced by —O—, —(CH$_2$)$_2$— may be replaced by —CH=CH—, and hydrogen may be replaced by a halogen; rings A$^1$, A$^2$ and B are independently trans-1,4-cyclohexylene or 1,4-phenylene; Z$^{11}$, Z$^{12}$, Z$^2$ and Z$^3$ are independently a single bond or alkylene having 2 or 4 carbons, provided that in the alkylene, —CH$_2$— may be replaced by —O— and —(CH$_2$)$_2$— may be replaced by —CH=CH—; and one of X$_1$ and X$_2$ is fluorine, and the other thereof is chlorine, provided that:

in a case where:
in formula (b-1), rings A$^1$ and B are trans-1,4-cyclohexylene, Z$^{11}$ is a single bond, and Z$^2$ is —CH$_2$O—, and
in formula (d-1), rings A$^1$, A$^2$ and B are trans-1,4-cyclohexylene, Z$^{11}$ and Z$^{12}$ are a single bond, and Z$^2$ is a single bond or —CH$_2$O—, Rb$_1$ is one of linear alkoxy having 1 to 9 carbons, linear alkoxyalkyl having 2 to 9 carbons, linear alkenyl having 2 to 10 carbons, linear alkenyloxy having 2 to 9 carbons, linear fluoroalkyl having 1 to 10 carbons, and linear fluoroalkoxy having 1 to 9 carbons.

3. The liquid crystal compound according to item 2, wherein the compound represented by formula (a-1) or (b-1), wherein Ra$_1$ and Rb$_1$ are independently linear alkyl having 1 to 10 carbons, linear alkoxy having 1 to 9 carbons, linear alkoxyalkyl having 1 to 9 carbons, linear alkenyl having 2 to 10 carbons, linear alkenyloxy having 2 to 9 carbons, linear fluoroalkyl having 1 to 10 carbons or linear fluoroalkoxy having 1 to 9 carbons, and Z$^{11}$, Z$^{12}$, Z$^2$ and Z$^3$ are independently a single bond, —(CH$_2$)$_2$—, —CH=CH—, —CH$_2$O— or —OCH$_2$—.

4. The liquid crystal compound according to item 2, wherein the compound represented by formula (c-1) or (d-1), wherein Ra$_1$ and Rb$_1$ are independently linear alkyl having 1 to 10 carbons, linear alkoxy having 1 to 9 carbons, linear alkoxyalkyl having 1 to 9 carbons, linear alkenyl having 2 to 10 carbons, linear fluoroalkyl having 1 to 10 carbons or linear fluoroalkoxy having 1 to 9 carbons, and Z$^{11}$, Z$^{12}$, Z$^2$ and Z$^3$ are independently a single bond, —(CH$_2$)$_2$—, —CH=CH—, —CH$_2$O— or —OCH$_2$—.

5. The liquid crystal compound according to item 2, wherein the compound represented by one of formulas (a-1) to (d-1), wherein Ra$_1$ is linear alkyl having 1 to 10 carbons or linear alkenyl having 2 to 10 carbons, Rb$_1$ is linear alkyl having 1 to 10 carbons or linear alkoxy having 1 to 9 carbons, and $Z^{11}$, $Z^{12}$, $Z^2$ and $Z^3$ are independently a single bond, —(CH$_2$)$_2$—, —CH=CH—, —CH$_2$O— or —OCH$_2$—.

6. The liquid crystal compound according to item 2, wherein the compound represented by one of formulas (a-1) to (d-1), wherein $Z^{11}$, $Z^{12}$, $Z^2$ and $Z^3$ are independently a single bond, —(CH$_2$)$_2$— or —CH=CH—.

7. The liquid crystal compound according to item 2, wherein the compound represented by one of formulas (a-1) to (d-1), wherein Ra$_1$ is linear alkyl having 1 to 10 carbons or linear alkenyl having 2 to 10 carbons, Rb$_1$ is linear alkoxy having 1 to 9 carbons, $Z^{11}$, $Z^{12}$ and $Z^3$ are independently a single bond, —(CH$_2$)$_2$—, —CH=CH—, —CH$_2$O— or —OCH$_2$—, and $Z^2$ is —CH$_2$O—.

8. The liquid crystal compound according to any one of items 2 to 7, wherein the compound represented by one of formulas (a-1) to (d-1), wherein X$_1$ is fluorine, and X$_2$ is chlorine.

9. The liquid crystal compound according to any one of items 2 to 7, wherein the compound represented by one of formulas (a-1) to (d-1), wherein X$_1$ is chlorine, and X$_2$ is fluorine.

10. A liquid crystal compound represented by one of formulas (b-2-1) to (b-7-1):

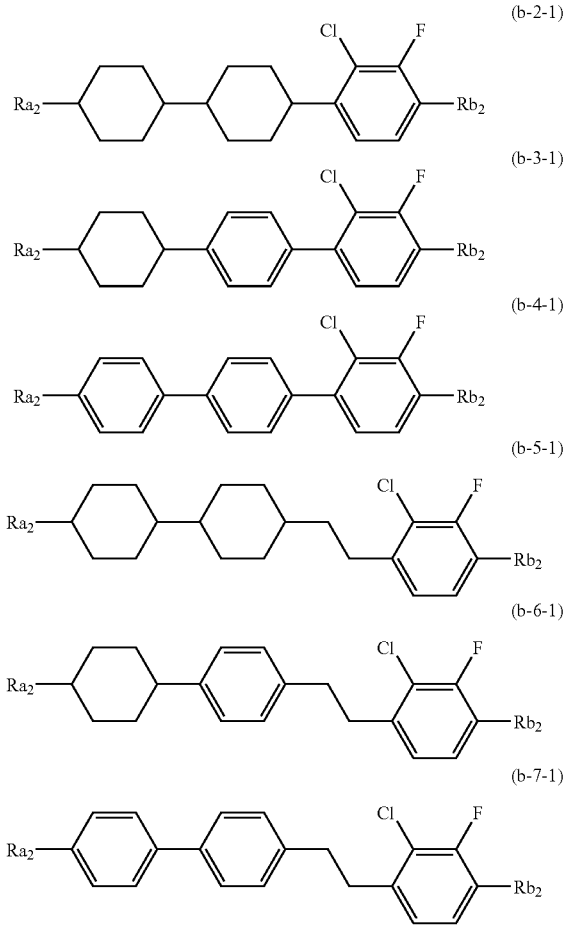

wherein Ra$_2$ is linear alkyl having 1 to 10 carbons or linear alkenyl having 2 to 10 carbons, Rb$_2$ is linear alkyl having 1 to 10 carbons or linear alkoxy having 1 to 9 carbons, and the cyclohexylene ring is trans-1,4-cyclohexylene.

11. A liquid crystal compound represented by one of formulas (b-2-2) to (b-7-2):

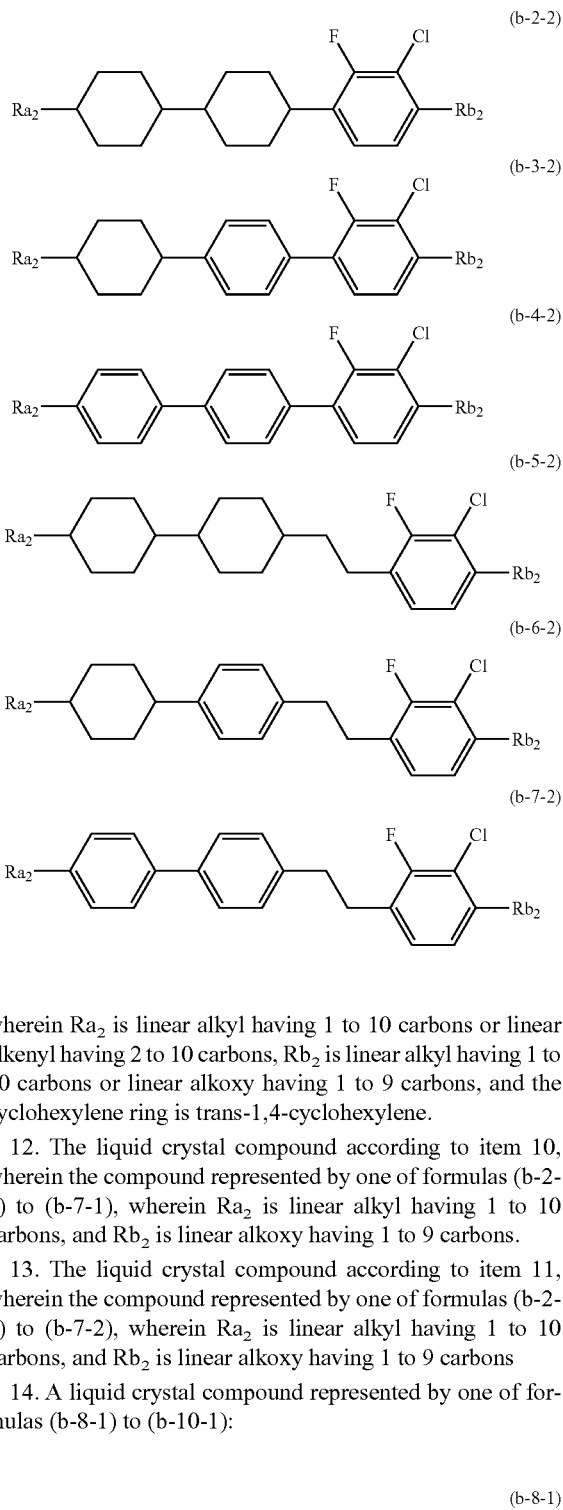

wherein Ra$_2$ is linear alkyl having 1 to 10 carbons or linear alkenyl having 2 to 10 carbons, Rb$_2$ is linear alkyl having 1 to 10 carbons or linear alkoxy having 1 to 9 carbons, and the cyclohexylene ring is trans-1,4-cyclohexylene.

12. The liquid crystal compound according to item 10, wherein the compound represented by one of formulas (b-2-1) to (b-7-1), wherein Ra$_2$ is linear alkyl having 1 to 10 carbons, and Rb$_2$ is linear alkoxy having 1 to 9 carbons.

13. The liquid crystal compound according to item 11, wherein the compound represented by one of formulas (b-2-2) to (b-7-2), wherein Ra$_2$ is linear alkyl having 1 to 10 carbons, and Rb$_2$ is linear alkoxy having 1 to 9 carbons 14. A liquid crystal compound represented by one of formulas (b-8-1) to (b-10-1):

(b-8-1)

-continued

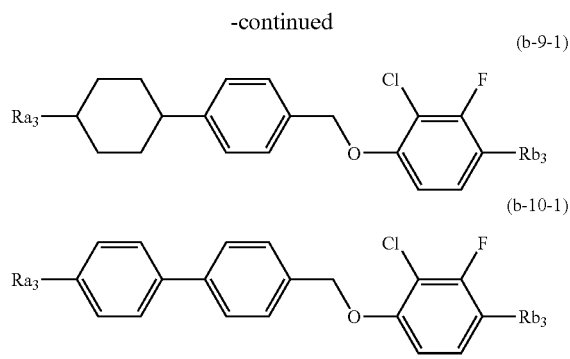
(b-9-1)
(b-10-1)

wherein Ra$_3$ is linear alkyl having 1 to 10 carbons or linear alkenyl having 2 to 10 carbons, Rb$_3$ is linear alkoxy having 1 to 9 carbons, and the cyclohexylene ring is trans-1,4-cyclohexylene.

15. A liquid crystal compound represented by one of formulas (b-8-2) to (b-10-2):

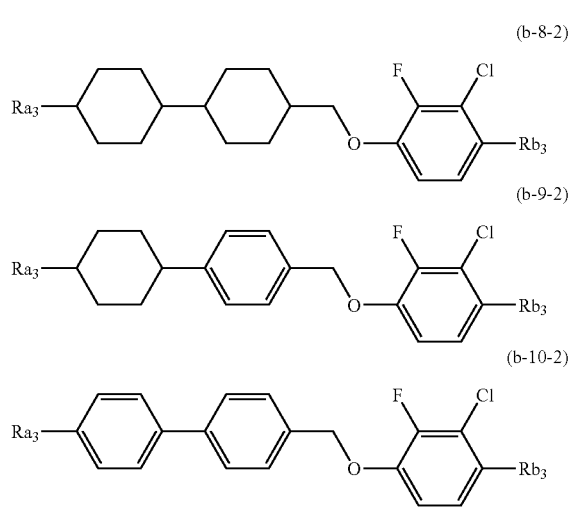
(b-8-2)
(b-9-2)
(b-10-2)

wherein Ra$_3$ is linear alkyl having 1 to 10 carbons or linear alkenyl having 2 to 10 carbons, Rb$_3$ is linear alkoxy having 1 to 9 carbons, and the cyclohexylene ring is trans-1,4-cyclohexylene.

16. The liquid crystal compound according to item 14, wherein the compound represented by one of formulas (b-8-1) to (b-10-1), wherein Ra$_3$ is linear alkyl having 1 to 10 carbons.

17. The liquid crystal compound according to item 15, wherein the compound represented by one of formulas (b-8-2) to (b-10-2), wherein Ra$_3$ is linear alkyl having 1 to 10 carbons.

18. A compound represented by formula (I) or (II):

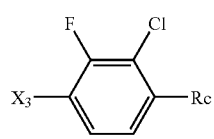
(I)

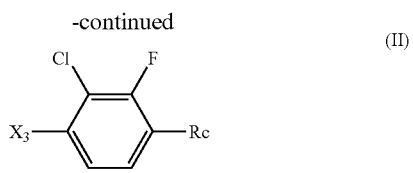
(II)

wherein Rc is alkyl having 1 to 10 carbons, provided that in the alkyl, —CH$_2$— may be replaced by —O—, —(CH$_2$)$_2$— may be replaced by —CH=CH—, and hydrogen may be replaced by a halogen; and X$_3$ is bromine or iodine.

19. A compound represented by formula (II) or (IV) used as an intermediate compound of the liquid crystal compound according to any one of items 1 to 17:

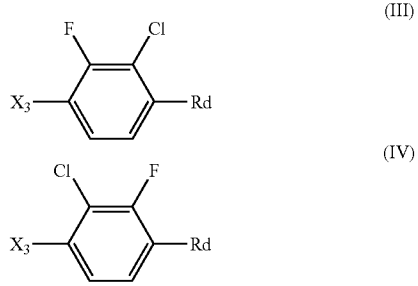
(III)
(IV)

wherein Rd is linear alkyl having 1 to 10 carbons or linear alkoxy having 1 to 9 carbons, and X$_3$ is bromine or iodine.

20. A compound represented by formula (V) or (VI) used as an intermediate compound of the liquid crystal compound according to any one of items 1 to 17:

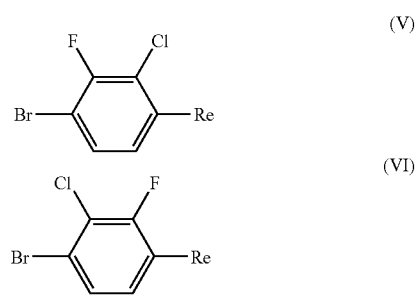
(V)
(VI)

wherein Re is linear alkyl having 1 to 10 carbons, provided that in the alkyl, —CH$_2$— may be replaced by —O—, —(CH$_2$)$_2$— may be replaced by —CH=CH—, and hydrogen may be replaced by a halogen.

21. A liquid crystal composition comprising the liquid crystal compound according to any one of items 1 to 17.

22. A liquid crystal display device comprising a liquid crystal composition comprising the liquid crystal compound according to any one of items 1 to 17.

The invention also concerns a liquid crystal composition containing the compound, and a liquid crystal display device containing the composition.

The liquid crystal compound of the invention has stability to heat, light and so forth, has a nematic phase in a wide temperature range, has small viscosity, suitable optical anisotropy, and suitable elastic constants K$_{33}$ and K$_{11}$ (K$_{33}$:

bend elastic constant, $K_{11}$: splay elastic constant), and has suitable negative dielectric anisotropy and excellent compatibility with other liquid crystal compounds. In particular, the compound of the invention is excellent in such points that the compound has suitable negative dielectric anisotropy and excellent compatibility with other liquid crystal compounds. The liquid crystal compound can be easily produced by using an intermediate compound of the invention having stability to heat, light and so forth capable of being used for wide variety of reactions.

The liquid crystal composition of the invention has low viscosity, suitable optical anisotropy, suitable negative dielectric anisotropy, low threshold voltage, high maximum temperature of nematic phase, and low minimum temperature of nematic phase. In particular, the composition of the invention is excellent in such points that since the liquid crystal compound of the invention has suitable negative dielectric anisotropy and excellent compatibility with other liquid crystal compounds, the compound of the invention can be used in a wide compositional range to prepare a liquid crystal composition having suitable negative dielectric anisotropy.

The liquid crystal display device containing the composition has short response time, small electric power consumption, small driving voltage, and large contrast, and can be used in wide temperature range. Accordingly, the liquid crystal display device can be favorably applied to a liquid crystal display device having such an operation mode as a PC mode, a TN mode, a STN mode, an ECB mode, an OCB mode, an IPS mode, a VA mode and so forth, and in particular, can be favorably applied to a liquid crystal display device having an IPS mode or a VA mode.

The invention will be described more specifically.

In the description, the content (percentage) of a compound means a percentage by weight (% by weight) based on the total weight of the composition.

(Liquid Crystal Compound)

The liquid crystal compounds of the invention have structures represented by formulas (a) to (d) (hereinafter, the compounds are referred to as a liquid crystal compound (1) as a generic term).

In the liquid crystal compound (1), Ra and Rb are independently hydrogen or linear alkyl having 1 to 10 carbons, provided that in the alkyl, —$CH_2$— may be replaced by —O—, and —$(CH_2)_2$— may be replaced by —CH=CH—.

For example, in the case where the linear alkyl is $CH_3$ $(CH_2)_3$—, the linear alkyl may be $CH_3(CH_2)_2O$—, $CH_3$—O—$(CH_2)_2$—, $CH_3$—O—$CH_2$—O—, $H_2C$=CH —$(CH_2)_2$—, $CH_3$—CH=CH—$CH_2$— or $CH_3$— CH=CH—O—, which are obtained by replacing —$CH_2$— by —O—, or replacing —$(CH_2)_2$— by —CH=CH—.

In Ra and Rb, two or more —$CH_2$— may be replaced by —O—, but in consideration of stability of the compound, a group having oxygens not adjacent to each other, such as $CH_3$—O—$CH_2$—O— is preferred in comparison to a group having oxygens adjacent to each other, such as $CH_3$—O— O—$CH_2$—.

More specific examples of Ra and Rb include hydrogen, linear alkyl, linear alkoxyalkyl, linear alkoxyalkoxy, linear alkenyl, linear alkenyloxy, linear alkenyloxyalkyl and linear alkoxyalkenyl.

In these groups, one or more hydrogen may be replaced by a halogen, and preferred examples of the halogen for replacing hydrogen include fluorine and chlorine.

In the groups, the alkyl chain is desirably a linear chain. In the case where the alkyl chain is a linear chain, the temperature range of the liquid crystal phase can be enhanced, and the viscosity thereof can be decreased. In the case where one of Ra and Rb is an optically active group, it is useful as a chiral dopant, and the addition of the compound prevents a reverse twisted domain from being formed in the liquid crystal display device.

Desirable Ra and Rb are linear alkyl, linear alkoxy, linear alkoxyalkyl, linear alkenyl, linear fluoroalkyl or linear fluoroalkoxy, more desirable Ra and Rb are linear alkyl, linear alkoxy, linear alkoxyalkyl, linear alkenyl, —$CH_2F$ or —$OCH_2F$, and further desirable Ra and Rb are linear alkyl, linear alkoxy or linear alkenyl.

In the case where Ra and Rb are the aforementioned groups, the temperature range of the liquid crystal phase of the liquid crystal compound can be enhanced.

The linear alkenyl has a desirable configuration of —CH=CH— depending on the position of the double bond of the alkenyl.

In the alkenyl having a double bond at an odd number position, such as —CH=$CHCH_3$, —CH=$CHC_2H_5$, —CH=$CHC_3H_7$, —CH=$CHC_4H_9$, —$C_2H_4$CH=$CHCH_3$ and —$C_2H_4$CH=$CHC_2H_5$, the configuration is desirably a trans configuration.

In the linear alkenyl having a double bond at an even number position, such as —$CH_2$CH=$CHCH_3$, —$CH_2$CH=$CHC_2H_5$ and —$CH_2$CH=$CHC_3H_7$, the configuration is desirably a cis configuration. The alkenyl compound having the aforementioned configuration has a wide temperature range of the liquid crystal phase, has large elastic constants $K_{33}$ and $K_{11}$ ($K_{33}$: bend elastic constant, $K_{11}$: splay elastic constant), and a small viscosity, and the addition of the compound to a liquid crystal composition increases a maximum temperature (TNI) of a nematic phase.

Specific examples of the linear alkyl include —$CH_3$, —$C_2H_5$, —$C_3H_7$, —$C_4H_9$, —$C_5H_{11}$, —$C_6H_{13}$ and —$C_7H_{15}$, specific examples of the linear alkoxy include —$OCH_3$, —$OC_2H_5$, —$OC_3H_7$, —$OC_4H_9$, —$OC_5H_{11}$ and —$OC_6H_{13}$, specific example of the linear alkoxyalkyl include —$CH_2OCH_3$, —$CH_2OC_2H_5$, —$CH_2OC_3H_7$, —$(CH_2)_2$ $OCH_3$, —$(CH_2)_2OC_2H_5$, —$(CH_2)_2OC_3H_7$, —$(CH_2)_3OCH_3$, —$(CH_2)_4OCH_3$ and —$(CH_2)_5OCH_3$, specific examples of the linear alkenyl include —CH=$CH_2$, —CH=$CHCH_3$, —$CH_2$CH=$CH_2$, —CH=$CHC_2H_5$, —$CH_2$CH=$CHCH_3$, —$(CH_2)_2$ CH=$CH_2$, —CH=$CHC_3H_7$, —$CH_2$CH=$CHC_2H_5$, —$(CH_2)_2$CH=$CHCH_3$ and —$(CH_2)_3$CH=$CH_2$, and specific examples of the linear alkenyloxy include —$OCH_2$CH=$CH_2$, —$OCH_2$CH=$CHCH_3$ and —$OCH_2$CH=$CHC_2H_5$.

Specific examples of the linear alkyl, in which hydrogen is replaced by a halogen, include —$CH_2F$, —$CHF_2$, —$CF_3$, —$(CH_2)_2F$, —$CF_2CH_2F$, —$CF_2CHF_2$, —$CH_2CF_3$, —$CF_2CF_3$, —$(CH_2)_3F$, —$(CF_2)_2CF_3$, —$CF_2CHFCF_3$ and —$CHFCF_2CF_3$, specific examples of the linear alkoxy, in which hydrogen is replaced by a halogen, include —$OCF_3$, —$OCHF_2$, —$OCH_2F$, —$OCF_2CF_3$, —$OCF_2CHF_2$, —$OCF_2CH_2F$, —$OCF_2CF_2CF_3$, —$OCF_2CHFCF_3$ and —$OCHFCF_2CF_3$, and specific examples of the linear alkenyl, in which hydrogen is replaced by a halogen, include —CH=CHF, —CH=$CF_2$, —CF=CHF, —CH=$CHCH_2F$, —CH=$CHCF_3$ and —$(CH_2)_2$CH=$CF_2$.

Among the specific examples of Ra and Rb, —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, —$CH_2OCH_3$, —$(CH_2)_2$ $OCH_3$, —$(CH_2)_3OCH_3$, —CH=$CH_2$, —CH=$CHCH_3$, —$CH_2$CH=$CH_2$, —CH=$CHC_2H_5$, —$CH_2$CH=$CHCH_3$, —$(CH_2)_2CH=CH_2$, —$CH=CHC_3H_7$, —$CH_2CH=CHC_2H_5$, —$(CH_2)_2CH=CHCH_3$, —$(CH_2)_3CH=CH_2$, —$OCH_2CH=CH_2$, —$OCH_2CH=CHCH_3$, —$OCH_2CH=CHC_2H_5$, —$CF_3$, —$CHF_2$, —$CH_2F$, —$OCF_3$, —$OCHF_2$, —$OCH_2F$, —$OCF_2CF_3$, —$OCF_2CHF_2$, —$OCF_2CH_2F$, —$OCF_2CF_2CF_3$, —$OCF_2CHFCF_3$ and —$OCHFCF_2CF_3$ are preferred, —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, —$CH_2OCH_3$, —$CH=CH_2$, —$CH=CHCH_3$, —$CH_2CH=CH_2$, —$CH=CHC_2H_5$, —$CH_2CH=CHCH_3$, —$(CH_2)_2CH=CH_2$, —$CH=CHC_3H_7$, —$CH_2CH=CHC_2H_5$, —$(CH_2)_2CH=CHCH_3$, —$(CH_2)_3CH=CH_2$, —$CHF_2$ and —$OCH_2F$ are more preferred, and —$CH_3$, —$C_2H_5$, —$C_3H_7$, —$C_4H_9$, —$C_5H_{11}$, —$OCH_3$, —$OC_2H_5$, —$OC_3H_7$, —$CH_2OCH_3$, —$CH=CH_2$, —$CH=CHCH_3$, —$(CH_2)_2CH=CH_2$ and —$(CH_2)_2CH=CHCH_3$ are further preferred.

Rings $A^1$, $A^2$, B and C are independently trans-1,4-cyclohexylene or 1,4-phenylene.

In the case where at least two rings among these are trans-1,4-cyclohexane, the optical anisotropy (Δn) and the viscosity can be small, and the addition of the liquid crystal compound to a liquid crystal composition increases the maximum temperature (TNI) of a nematic phase.

In the case where at least one ring among these is 1,4-phenylene, the optical anisotropy (Δn) can be relatively large, and the orientational order parameter can be large.

In the case where at least two rings among these are 1,4-phenylene, the optical anisotropy can be large.

Examples of $Z^{11}$, $Z^{12}$, $Z^2$ and $Z^3$ include a single bond, —$(CH_2)_2$—, —$CH_2O$—, —$OCH_2$—, —$CH=CH$—, —$(CH_2)_4$—, —$CH=CH-(CH_2)_2$—, —$CH_2$—$CH=CH$—$CH_2$—, —$(CH_2)_2$—$CH=CH$—, —$CH=CH$—$CH_2O$— and —$OCH_2$—$CH=CH$—.

In the case where $Z^{11}$, $Z^{12}$, $Z^2$ and $Z^3$ are a bonding group including —$CH=CH$—, —$CH=CH-(CH_2)_2$—, —$(CH_2)_2$—$CH=CH$—, —$CH=CH$—$CH_2O$— and —$OCH_2$—$CH=CH$—, the configuration of the other groups with respect to the double bond is desirably a trans configuration, and in the case where they are —$CH_2$—$CH=CH$—$CH_2$—, the configuration is desirably a cis configuration. According to the configurations of the liquid crystal compound, the temperature range of the liquid crystal phase can be enhanced, and the elastic constants $K_{33}$ can be increased. The addition of the liquid crystal compound to a liquid crystal composition increases the maximum temperature ($T_{NI}$) of a nematic phase.

Among the examples of $Z^{11}$, $Z^{12}$, $Z^2$ and $Z^3$, a single bond, —$(CH_2)_2$—, —$CH_2O$—, —$OCH_2$—, —$CH=CH$— and —$(CH_2)_4$— are preferred, a single bond, —$(CH_2)_2$—, —$CH_2O$—, —$OCH_2$— and —$CH=CH$— are more preferred, and a single bond and —$(CH_2)_2$— are further preferred.

In the case where $Z^{11}$, $Z^{12}$, $Z^2$ and $Z^3$ are a single bond, —$(CH_2)_2$—, —$CH_2O$—, —$OCH_2$—, —$CH=CH$— or —$(CH_2)_4$—, the viscosity of the compound can be relatively small. In the case where $Z^{11}$, $Z^{12}$, $Z^2$ and $Z^3$ are a single bond, —$(CH_2)_2$— or —$CH=CH$—, the viscosity of the compound can be further small.

In the case where $Z^{11}$, $Z^{12}$, $Z^2$ and $Z^3$ include —$CH=CH$—, the temperature range of the liquid crystal phase can be enhanced, the elastic constant ratio $K_{33}/K_{11}$ can be large, and the viscosity of the compound can be small. The addition of the liquid crystal compound to a liquid crystal composition increases the maximum temperature ($T_{NI}$) of a nematic phase.

In the case where $Z^{11}$, $Z^{12}$, $Z^2$ and $Z^3$ are a single bond, the elastic constant $K_{33}$ can be small.

One of $X_1$ and $X_2$ is fluorine, and the other thereof is chlorine, i.e., $X_1$ and $X_2$ are different halogens. In the case where one of $X_1$ and $X_2$ is fluorine with the other thereof being chlorine, the compatibility with other liquid crystal compounds can be improved in comparison to the case where both $X_1$ and $X_2$ are fluorine. Accordingly, the liquid crystal compound (1) can be added in a larger amount than the other liquid crystal compounds, whereby a liquid crystal composition having a higher dielectric anisotropy (Δ∈) than the conventional liquid crystal composition can be obtained, and the temperature range where the liquid crystal composition can be used as a liquid crystal device can be enhanced.

Furthermore, in the case where $X_1$ is chlorine, and $X_2$ is fluorine, the compatibility with other liquid crystal compounds is further improved, and the compounds represented by formulas (b) and (d) are particularly excellent in compatibility.

In the case where:
in formula (a), rings B and C are trans-1,4-cyclohexylene, and $Z^2$ and $Z^3$ are a single bond,
in formula (b), rings $A^1$ and B are trans-1,4-cyclohexylene, $Z^{11}$ is a single bond, and $Z^2$ is —$CH_2O$—, and
in formula (d), rings $A^1$, $A^2$ and B are trans-1,4-cyclohexylene, $Z^{11}$ and $Z^{12}$ are a single bond, and $Z^2$ is a single bond or —$CH_2O$—, Rb is one of linear alkoxy having 1 to 9 carbons, linear alkoxyalkyl having 2 to 9 carbons, linear alkenyl having 2 to 10 carbons, linear alkenyloxy having 2 to 9 carbons, linear fluoroalkyl having 1 to 10 carbons, and linear fluoroalkoxy having 1 to 9 carbons.

The liquid crystal compound (1) may contain such an amount of an isotope, such as $^2H$ (deuterium) and $^{13}C$, that is larger than the natural abundance because the presence of an isotope causes no large difference in characteristics of the compound.

In the case where the liquid crystal compound (1) has three rings having a 1,4-phenylene skeleton and/or a trans-1,4-cyclohexylene skeleton, the viscosity can be small, and the maximum temperature of a nematic phase can be increased.

In the case where the liquid crystal compound (1) has four of the aforementioned rings, the maximum temperature of a nematic phase can be further increased.

The liquid crystal compound (1) can be adjusted to have desired characteristics including the optical anisotropy (Δn) and the dielectric anisotropy (Δ∈) by suitably selecting the end groups Ra and Rb, the rings $A^1$, $A^3$, B and C, and the bonding groups $Z^{11}$, $Z^{12}$, $Z^2$ and $Z^3$ within the aforementioned ranges.

(Preferred Embodiments of Liquid Crystal Compound (1))

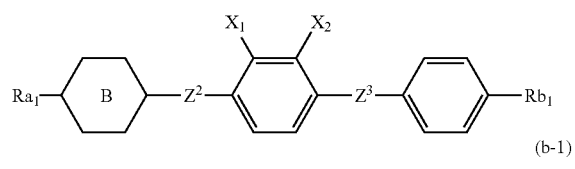

(a-1)

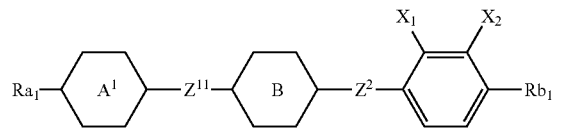

(b-1)

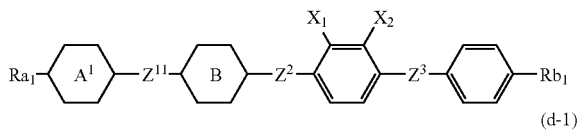
(c-1)

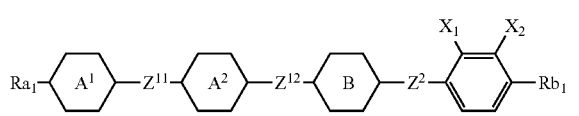
(d-1)

In the liquid crystal compound (1), compounds represented by formulas (a-1) to (d-1) are preferred. The compounds represented by formulas (a-1) to (d-1) can enhance the temperature range of the liquid crystal phase, can decrease the viscosity, can increase the optical anisotropy (Δn), and can negatively increase the dielectric anisotropy (Δε).

In the formulas (a-1) to (d-1), $Ra_1$ and $Rb_1$ are independently linear alkyl having 1 to 10 carbons, provided that in the alkyl, —$CH_2$— may be replaced by —O—, —$(CH_2)_2$— may be replaced by —CH=CH—, and hydrogen may be replaced by a halogen.

Rings $A^1$, $A^2$ and B, the bonding groups $Z^{11}$, $Z^{12}$ and $Z^3$, and the groups $X_1$ and $X_2$ are the same as in the liquid crystal compound (1).

In the case where:

in formula (b-1), rings $A^1$ and B are trans-1,4-cyclohexylene, $Z^{11}$ is a single bond, and $Z^2$ is —$CH_2O$—, and in formula (d-1), rings $A^1$, $A^2$ and B are trans-1,4-cyclohexylene, $Z^{11}$ and $Z^{12}$ are a single bond, and $Z^2$ is a single bond or —$CH_2O$—, $Rb_1$ is one of linear alkoxy having 1 to 9 carbons, linear alkoxyalkyl having 2 to 9 carbons, linear alkenyl having 2 to 10 carbons, linear alkenyloxy having 2 to 9 carbons, linear fluoroalkyl having 1 to 10 carbons, and linear fluoroalkoxy having 1 to 9 carbons.

Among the compounds represented by formulas (a-1) to (d-1), such a compound is preferred that $Ra_1$ and $Rb_1$ are independently linear alkyl having 1 to 10 carbons, linear alkoxy having 1 to 9 carbons, linear alkoxyalkyl having 1 to 9 carbons, linear alkenyl having 2 to 10 carbons, linear alkenyloxy having 2 to 9 carbons, linear fluoroalkyl having 1 to 10 carbons or linear fluoroalkoxy having 1 to 9 carbons, and $Z^{11}$, $Z^{12}$, $Z^2$ and $Z^3$ are independently a single bond, —$(CH_2)_2$—, —CH=CH—, —$CH_2O$— or —$OCH_2$—.

In the preferred compound, it is preferred that $Ra_1$ is linear alkyl having 1 to 10 carbons or linear alkenyl having 2 to 10 carbons, $Rb_1$ is linear alkyl having 1 to 10 carbons or linear alkoxy having 1 to 9 carbons, and $Z^{11}$, $Z^{12}$, $Z^2$ and $Z^3$ are independently a single bond, —$(CH_2)_2$—, —CH=CH—, —$CH_2O$— or —$OCH_2$—.

It is also preferred that $Z^{11}$, $Z^{12}$, $Z^2$ and $Z^3$ are independently a single bond, —$(CH_2)_2$— or —CH=CH—. In the case where the compounds (a-1) to (d-1) have the aforementioned structure, the liquid crystal compound can further decrease the viscosity and can have excellent compatibility with other liquid crystal compounds, and the addition of the compound to a liquid crystal composition increases a maximum temperature (TNI) of a nematic phase.

It is also preferred that $Ra_1$ is linear alkyl having 1 to 10 carbons or linear alkenyl having 2 to 10 carbons, $Rb_1$ is linear alkoxy having 1 to 9 carbons, and $Z^2$ is —$CH_2O$—. In the case where the compounds (a-1) to (d-1) have the aforementioned structure, the dielectric anisotropy can be further negatively increased.

(Preferred Embodiments of Liquid Crystal Compound (b))

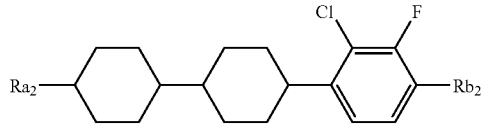
(b-2-1)

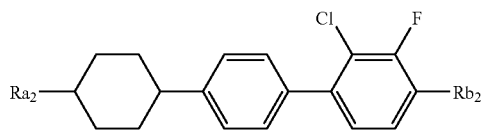
(b-3-1)

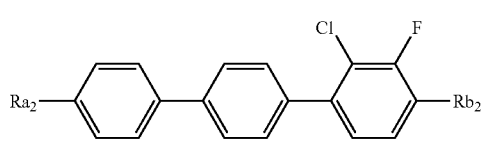
(b-4-1)

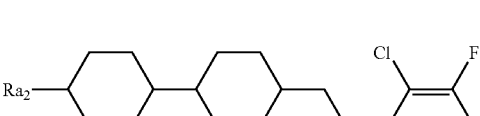
(b-5-1)

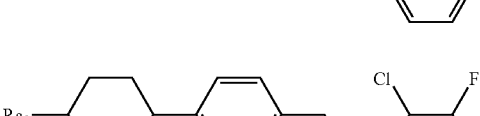
(b-6-1)

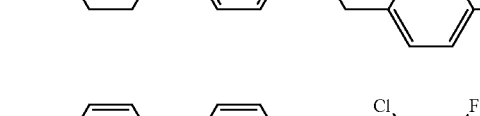
(b-7-1)

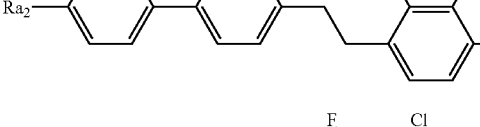
(b-2-2)

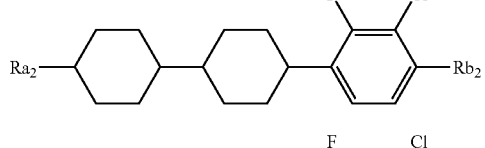
(b-3-2)

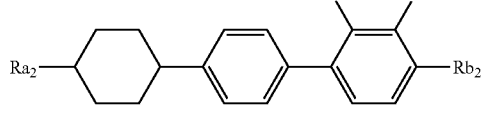
(b-4-2)

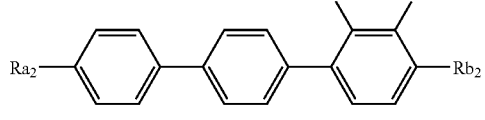
(b-5-2)

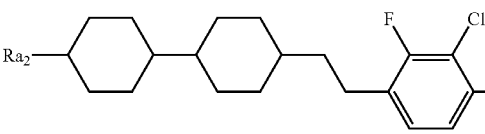

-continued

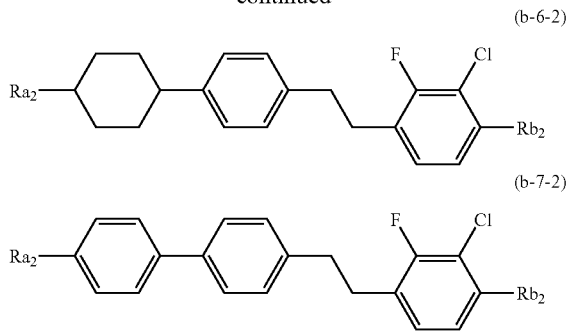

In the liquid crystal compound (1) represented by formula (b), preferred examples of the liquid crystal compound include liquid crystal compounds represented by formulas (b-2-1) to (b-7-1) and (b-2-2) to (b-7-2).

The liquid crystal compounds are particularly excellent in compatibility with other liquid crystal compounds.

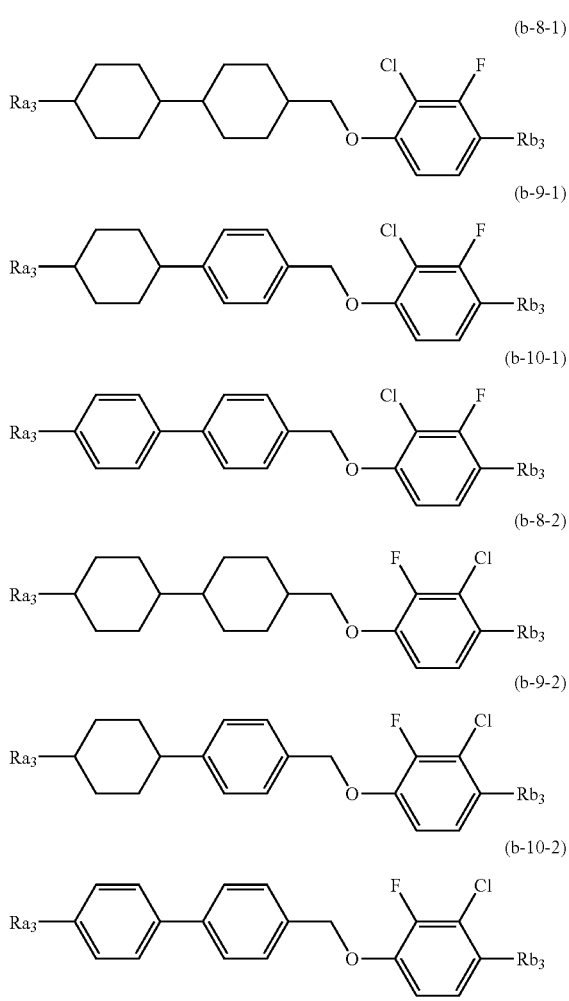

In the liquid crystal compound represented by formula (b), preferred examples of the liquid crystal compound also include liquid crystal compounds represented by formulas (b-8-1) to (b-10-1) and (b-8-2) to (b-10-2).

The liquid crystal compounds are particularly excellent in compatibility with other liquid crystal compounds, and can negatively increase the dielectric anisotropy. In particular, the compound where $Rb_3$ is linear alkoxy can further negatively increase the dielectric anisotropy.

In the case where the liquid crystal compound has the structure represented by formula (1), the compound has suitable negative dielectric anisotropy and is considerably excellent in compatibility with other liquid crystal compounds. Furthermore, the compound has stability to heat, light and so forth, has a nematic phase in a wide temperature range, has small viscosity, suitable optical anisotropy, and suitable elastic constants $K_{33}$ and $K_{11}$. A liquid crystal composition containing the liquid crystal compound (1) is stable under the conditions where a liquid crystal display device is generally used, and suffers no deposition of the compound as crystals (or a smectic phase) upon storing at a low temperature.

Accordingly, the liquid crystal compound (1) can be favorably applied to a liquid crystal composition used in a liquid crystal display device having such an operation mode as a PC mode, a TN mode, a STN mode, an ECB mode, an OCB mode, an IPS mode, a VA mode and so forth, and in particular, can be favorably applied to a liquid crystal composition used in a liquid crystal display device having an IPS mode or a VA mode.

(Synthesis of Liquid Crystal Compound (1))

The liquid crystal compound (1) can be synthesized by suitably combining synthetic methods of organic synthesis chemistry. A method for introducing the target end groups, rings and bonding groups to a starting material is disclosed, for example, in known publications, such as *Organic Synthesis*, published by John Wiley & Sons, Inc., *Organic Reactions*, published by John Wiley & Sons, Inc., *Comprehensive Organic Synthesis*, published by Pergamon Press, and *Shin Jikken Kagaku Koza* (Lectures on New Experimental Chemistry), published by Maruzen, Inc.

(Formation of Bonding Group $Z^{11}$, $Z^{12}$, $Z^2$ or $Z^3$)

An example of the method for forming the bonding group $Z^{11}$, $Z^{12}$, $Z^2$ or $Z^3$ will be described. A reaction scheme for forming the bonding group is shown. In the scheme, $MSG^1$ and $MSG^2$ are a monovalent organic group. The plural groups represented by $MSG^1$ (or $MSG^2$) used in the scheme may be the same as or different from each other. The compounds (1A) to (1G) correspond to the compound (1).

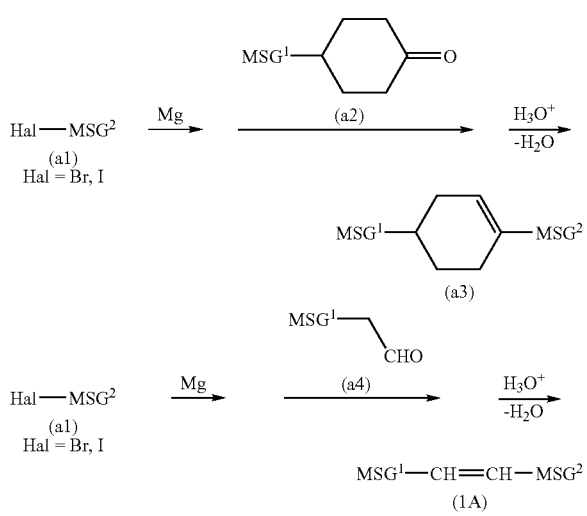

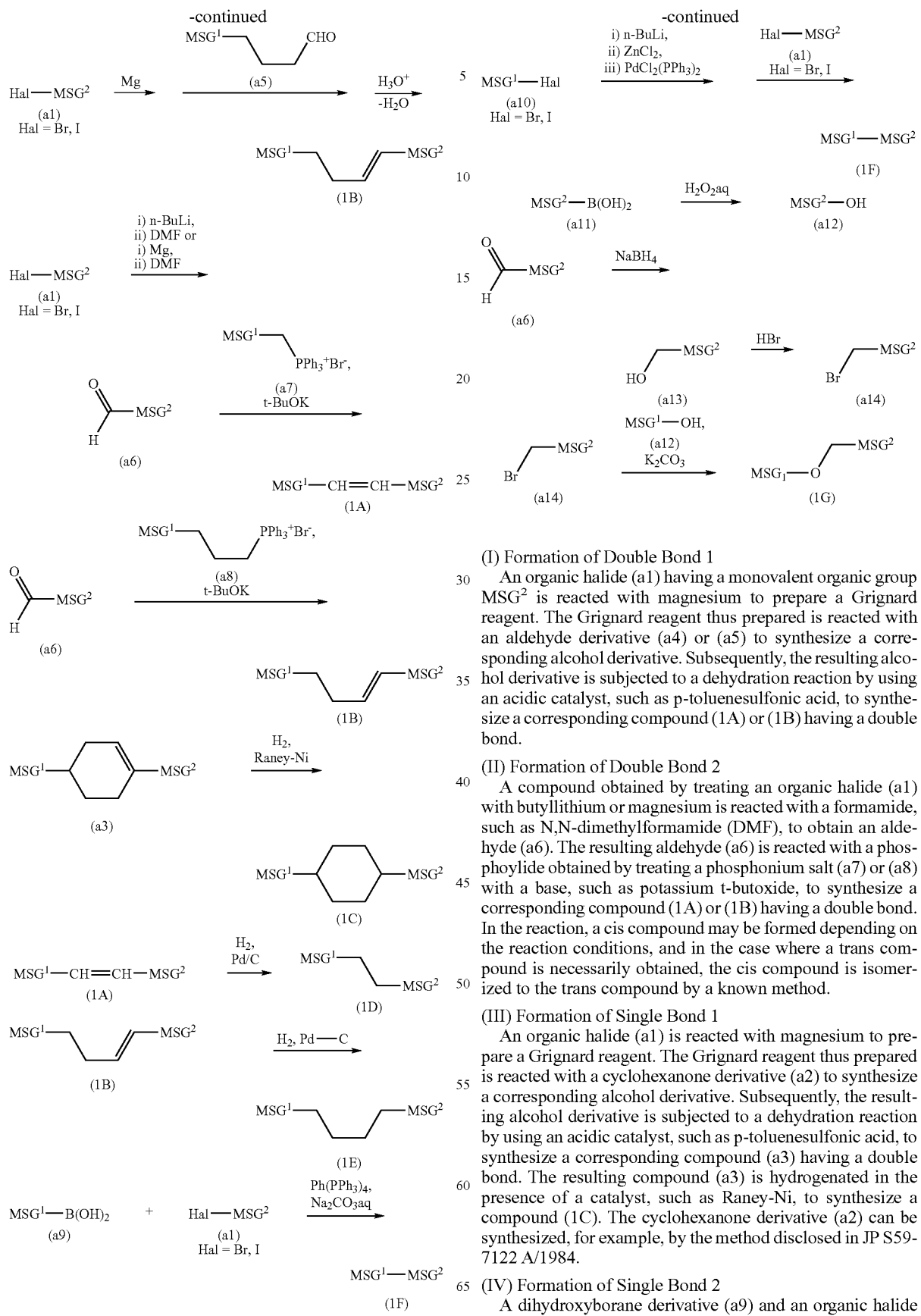

(I) Formation of Double Bond 1

An organic halide (a1) having a monovalent organic group $MSG^2$ is reacted with magnesium to prepare a Grignard reagent. The Grignard reagent thus prepared is reacted with an aldehyde derivative (a4) or (a5) to synthesize a corresponding alcohol derivative. Subsequently, the resulting alcohol derivative is subjected to a dehydration reaction by using an acidic catalyst, such as p-toluenesulfonic acid, to synthesize a corresponding compound (1A) or (1B) having a double bond.

(II) Formation of Double Bond 2

A compound obtained by treating an organic halide (a1) with butyllithium or magnesium is reacted with a formamide, such as N,N-dimethylformamide (DMF), to obtain an aldehyde (a6). The resulting aldehyde (a6) is reacted with a phosphoylide obtained by treating a phosphonium salt (a7) or (a8) with a base, such as potassium t-butoxide, to synthesize a corresponding compound (1A) or (1B) having a double bond. In the reaction, a cis compound may be formed depending on the reaction conditions, and in the case where a trans compound is necessarily obtained, the cis compound is isomerized to the trans compound by a known method.

(III) Formation of Single Bond 1

An organic halide (a1) is reacted with magnesium to prepare a Grignard reagent. The Grignard reagent thus prepared is reacted with a cyclohexanone derivative (a2) to synthesize a corresponding alcohol derivative. Subsequently, the resulting alcohol derivative is subjected to a dehydration reaction by using an acidic catalyst, such as p-toluenesulfonic acid, to synthesize a corresponding compound (a3) having a double bond. The resulting compound (a3) is hydrogenated in the presence of a catalyst, such as Raney-Ni, to synthesize a compound (1C). The cyclohexanone derivative (a2) can be synthesized, for example, by the method disclosed in JP S59-7122 A/1984.

(IV) Formation of Single Bond 2

A dihydroxyborane derivative (a9) and an organic halide (a1) are reacted in the presence, for example, of a catalyst containing a carbonate aqueous solution and tetrakis(triphenylphosphine)palladium (Pd(PPh$_3$)$_4$) to synthesize a compound (1F).

In alternative, an organic halide (a10) having a monovalent organic group MSG$^1$ is reacted with butyllithium and then reacted with zinc chloride, and thereafter, the resulting compound is reacted with a compound (a1) in the presence, for example, of bistriphenylphosphinedichloropalladium (Pd(PPh$_3$)$_2$Cl$_2$) to synthesize a compound (1F).

(V) Formation of —(CH$_2$)$_2$—
A compound (1A) is hydrogenated in the presence of a catalyst, such as carbon-supported palladium (Pd/C) to synthesize a compound (1D).

(VI) Formation of —(CH$_2$)$_4$—
A compound (1B) is hydrogenated in the presence of a catalyst, such as carbon-supported palladium (Pd/C) to synthesize a compound (1E).

(VII) Formation of —CH$_2$O— or —OCH$_2$—
A dihydroxyborane derivative (a11) is oxidized with an oxidizing agent, such as hydrogen peroxide, to obtain an alcohol derivative (a12). Separately, an aldehyde derivative (a6) is reduced with a reducing agent, such as sodium borohydride, to obtain a compound (a13). The resulting compound (a13) is halogenated, for example, with hydrobromic acid to obtain an organic halide (a14). The compound (a12) and the compound (a14) thus obtained are reacted in the presence, for example, of potassium carbonate to synthesize a compound (1G).

(Production Method of Compounds (I) and (II))

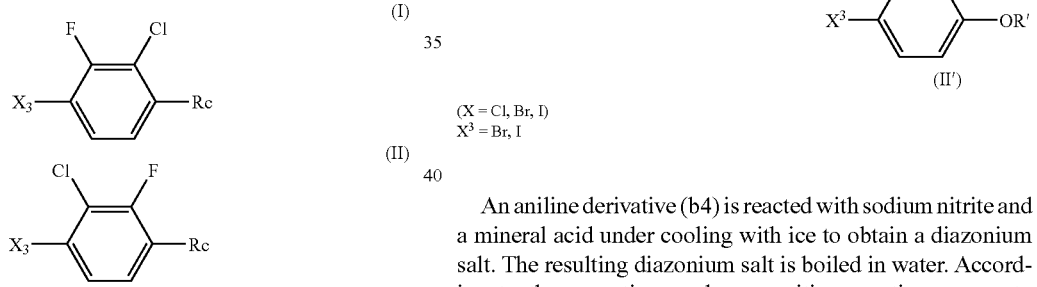

An example of the production method of compounds (I) and (II), which may be a starting material of the liquid crystal compound (1), will be described.

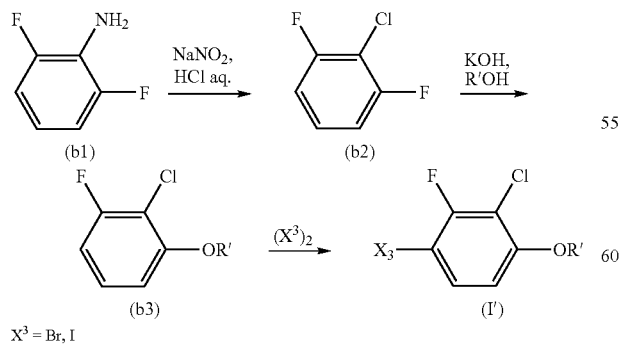

An aniline derivative (b1) is reacted with sodium nitrite and a mineral acid under cooling with ice to obtain a diazonium salt. The resulting diazonium salt is reacted with hydrochloric acid and cuprous chloride and then subjected to steam distillation to obtain a compound (b2). The resulting compound (b2) is etherified by reacting with an alcohol derivative (R'OH) in the presence of a base, such as potassium hydroxide, to obtain a compound (b3). The resulting compound (b3) is reacted with a halogen molecule, such as bromine and iodine, to produce a compound (I') as an example of the compound (I) of the invention.

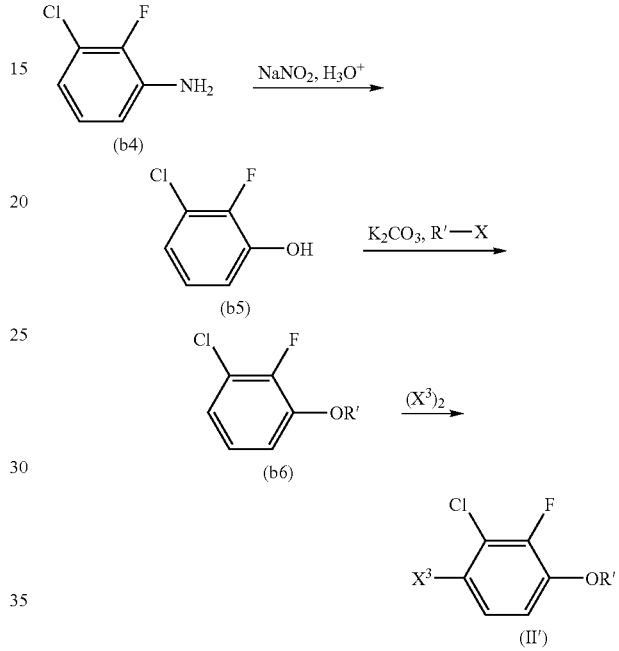

An aniline derivative (b4) is reacted with sodium nitrite and a mineral acid under cooling with ice to obtain a diazonium salt. The resulting diazonium salt is boiled in water. According to the operation, a decomposition reaction occurs to obtain a phenol derivative (b5), in which the amino group in (b4) converted into hydroxyl group. The resulting compound (b5) is etherified by reacting with a corresponding organic halide (R'—X) in the presence of a base, such as potassium hydroxide, to obtain a compound (b6). The resulting compound (b6) is reacted with a halogen molecule, such as bromine and iodine, to produce a compound (II') as an example of the compound (II) of the invention.

(Production Method of Liquid Crystal Compound (1))

Examples of the production method of the liquid crystal compound (1), i.e., the liquid crystal compound represented by formulas (a) to (d), will be described.

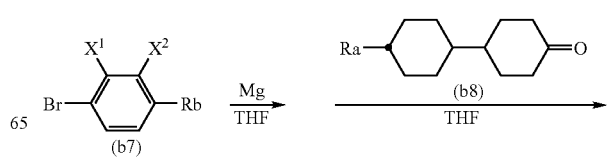

-continued

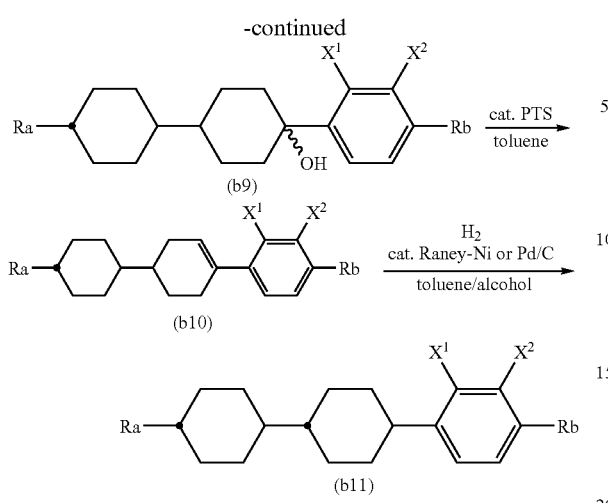

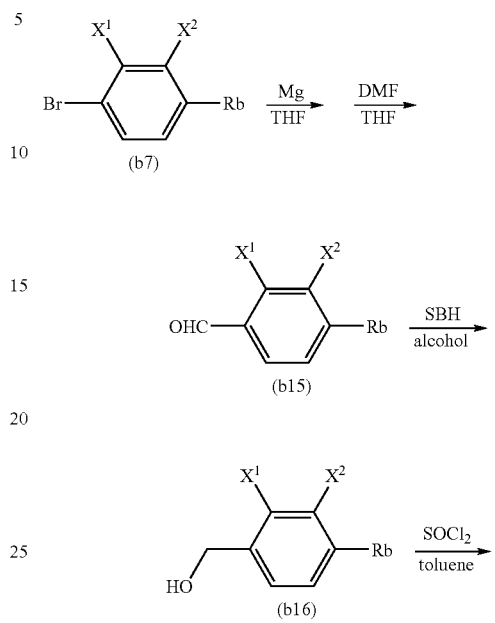

A compound (b7) is reacted with magnesium to prepare a Grignard reagent. The Grignard reagent is reacted with a carbonyl derivative (b8) to obtain an alcohol derivative (b9). The resulting alcohol derivative (b9) is subjected to a dehydration reaction in the presence of an acidic catalyst, such as p-toluenesulfonic acid (PTS), to obtain a compound (b10). The compound (b10) is then subjected to a hydrogenation reaction in the presence of a catalyst, such as Pd/C or Raney-Ni, to obtain a compound (b11) as an example of the liquid crystal compound (1) of the invention.

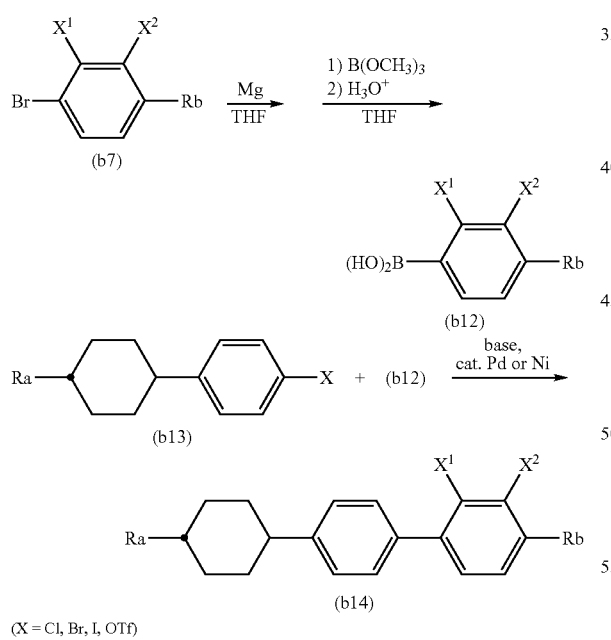

(X = Cl, Br, I, OTf)

A compound (b7) is reacted with magnesium to prepare a Grignard reagent. The Grignard reagent is reacted with a boronic acid ester and hydrolyzed in an acidic atmosphere to obtain a dihydroxyborane derivative (b12). The dehydroxyboran derivative (b12) and a compound (b13) are reacted in the presence of a base, such as potassium carbonate or sodium hydroxide, and a catalyst, such as Pd/C, Pd(PPh$_3$)$_4$ or Pd(PPh$_3$)$_2$Cl$_2$, to obtain a compound (b14) as an example of the liquid crystal compound (1) of the invention.

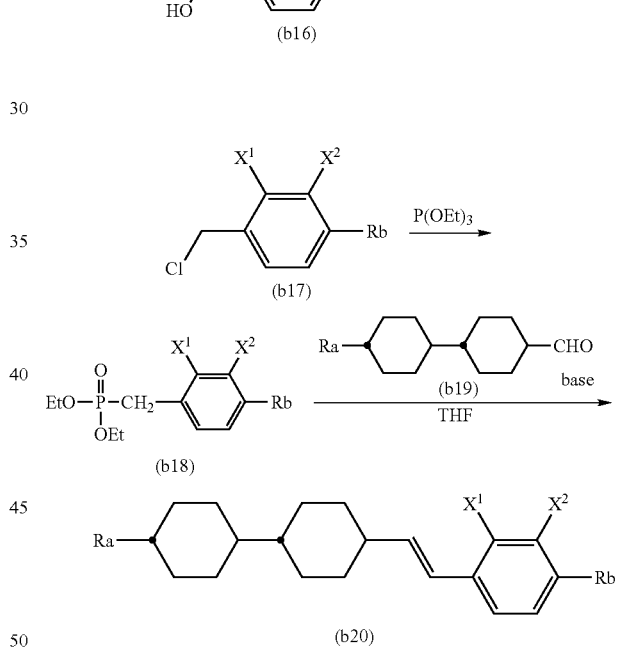

A compound (b7) is reacted with magnesium to prepare a Grignard reagent. The Grignard reagent is reacted with N,N-dimethylformamide and hydrolyzed in an acidic atmosphere to obtain an aldehyde derivative (b15). The resulting aldehyde derivative (b15) is reduced, for example, with sodium borohydride and then chlorinated, for example, with thionyl chloride, and is then further subjected to an Arbusov reaction with triethyl phosphite to obtain a compound (b18). The compound (b18) and an aldehyde derivative (b19) are reacted in the presence of a base, such as sodium ethoxide. Depending on necessity, isomers thus formed (E compound or Z compound) are isomerized, for example, with benzenesulfinic acid to produce a compound (b20) as an example of the liquid crystal compound (1) of the invention.

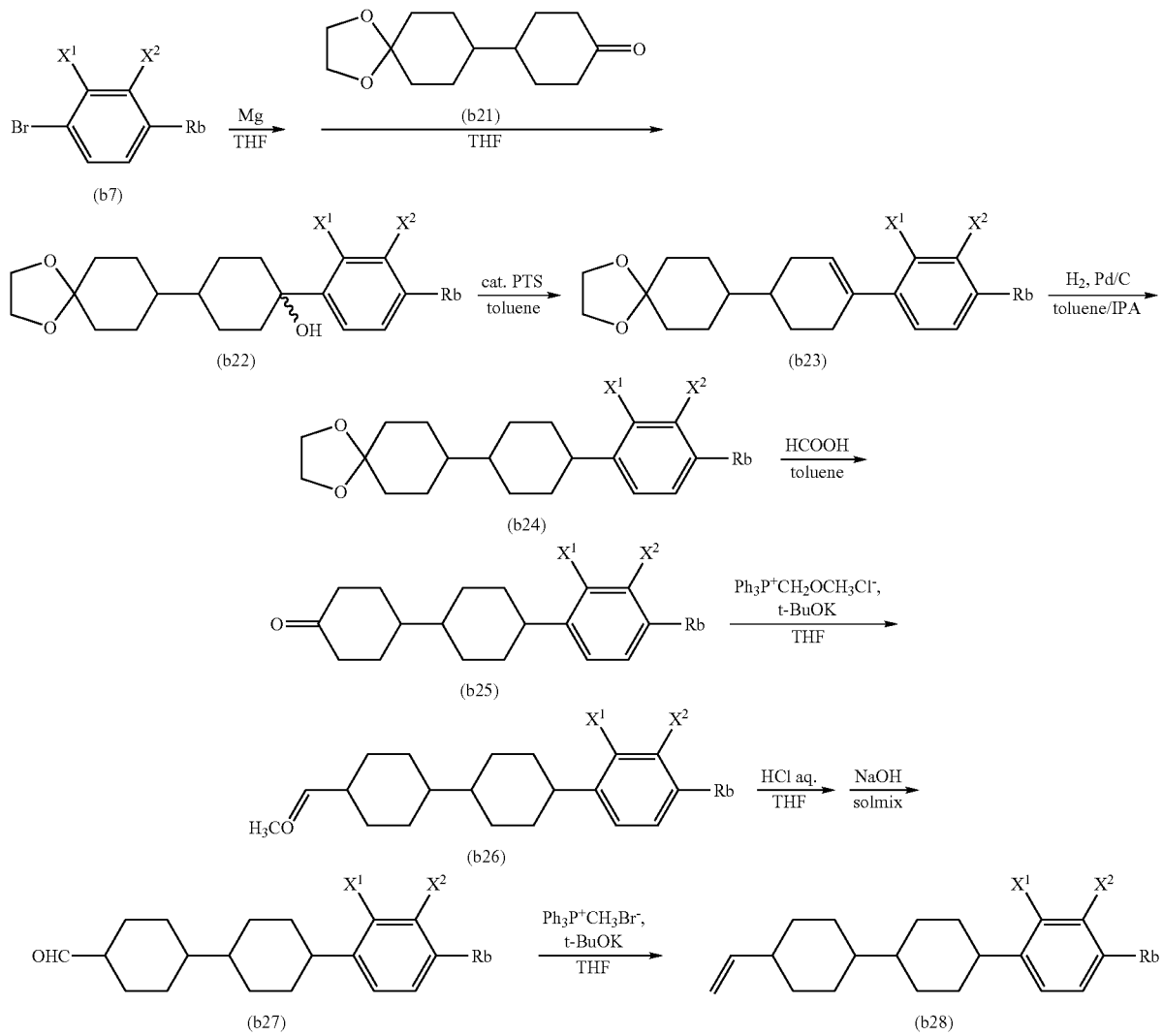

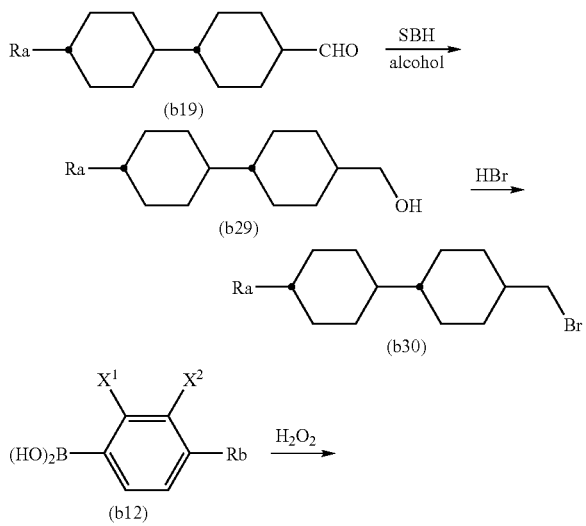

A compound (b7) is reacted with magnesium to prepare a Grignard reagent. The Grignard reagent is reacted with a carbonyl derivative (b21) to obtain an alcohol derivative (b22). The resulting alcohol derivative (b22) is subjected to dehydration reaction in the presence of an acidic catalyst, such as p-toluenesulfonic acid, to obtain a compound (b23). The compound (b23) is subjected to a hydrogenation reaction in the presence of a catalyst, such as Pd/C, to obtain a compound (b24). The compound (b24) is hydrolyzed in an acidic atmosphere, such as formic acid, to obtain a carbonyl derivative (b25). The resulting carbonyl derivative (b25) is subjected to Wittig reaction with a phosphoylide prepared from methoxymethyltriphenylphosphonium chloride and a base, such as potassium t-butoxide (t-BuOK), to obtain an enol ether derivative (b26). The resulting enol ether derivative (b26) is hydrolyzed in an acidic atmosphere, and then is isomerized in a basic atmosphere depending on necessity, to obtain an aldehyde derivative (b27). The aldehyde derivative (b27) is reacted with a phosphoylide prepared from methyl-triphenylphosphonium bromide and a base, such as t-BuOK, to obtain a compound (b28) as an example of the liquid crystal compound (1) of the invention.

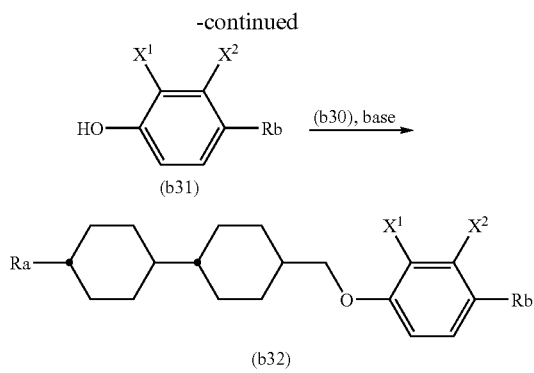

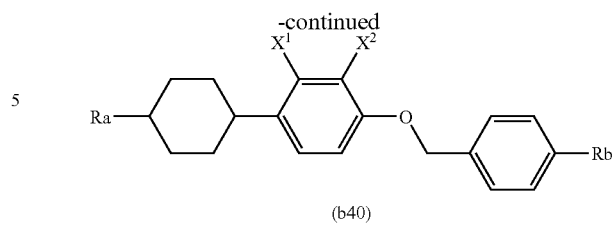

A compound (b19) is reduced, for example, with sodium borohydride to obtain a compound (b29). Subsequently, the compound (b29) is brominated, for example, with hydrobromic acid to obtain a compound (b30). Separately, a dihydroxyborane derivative (b12) is subjected to an oxidation reaction with an oxidizing agent, such as hydrogen peroxide, to obtain a phenol derivative (b31). The compound (b30) and the phenol derivative (b31) obtained by the aforementioned operations are subjected to an etherification reaction in the presence of a base, such as potassium carbonate, to obtain a compound (b32) as an example of the liquid crystal compound (1) of the invention.

A compound (b33) is reacted with magnesium to prepare a Grignard reagent. The Grignard reagent is reacted with a carbonyl derivative (b34) to obtain an alcohol derivative (b35). The resulting alcohol derivative (b35) is subjected to a dehydration reaction in the presence of an acidic catalyst, such as p-toluenesulfonic acid, to obtain a compound (b36). The compound (b36) is subjected to a hydrogenation reaction in the presence of a catalyst, such as Raney-Ni, to obtain a compound (b37). The compound (b37) is then subjected to a demethylation reaction with a Lewis acid, such as boron tribromide, to obtain a phenol derivative (b38). The resulting phenol derivative (b38) is subjected to an etherification reaction with a compound (b39) in the presence of a base, such as potassium carbonate, to obtain a compound (b40) as an example of the liquid crystal compound (1) of the invention.

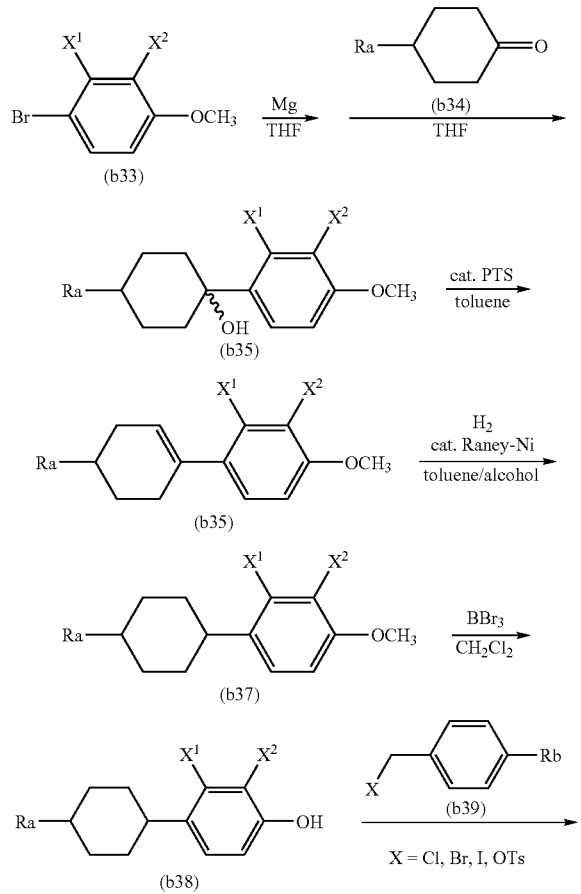

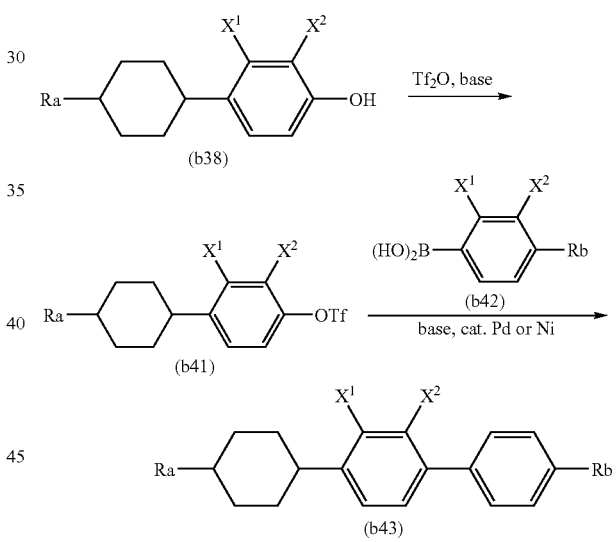

A compound (b38) is reacted with trifluoromethanesulfonic anhydride in the presence of a base, such as pyridine, to obtain a compound (b41). Subsequently, the compound (b41) is reacted with a dihydroxyborane derivative (b42) in the presence of a base, such as potassium carbonate, with Pd(PPh$_3$)$_4$ or Pd/C as a catalyst to obtain a compound (b43) as an example of the liquid crystal compound (1) of the invention.

(Liquid Crystal Composition)

The liquid crystal composition of the invention will be described. The components of the liquid crystal composition contain at least one of the liquid crystal compound (1), and may contain two or more liquid crystal compounds (1) or may be constituted only by the liquid crystal compound (1). The content of the liquid crystal compound (1) in the liquid crystal composition of the invention is not particularly limited, and it is preferred that approximately 1 to approximately 99% by weight of the liquid crystal compound (1) is contained based on the total weight of the liquid crystal composition. Upon preparing the liquid crystal composition of the invention, the components may be selected in consideration, for example, of the dielectric anisotropy of the liquid crystal compound (1)

(Liquid Crystal Display Device)

The liquid crystal composition of the invention can be applied to a liquid crystal display device having such an operation mode as a PC mode, a TN mode, a STN mode, a BTN mode, an ECB mode, an OCB mode, an IPS mode, a VA mode and so forth, and in particular, can be favorably applied to a liquid crystal display device having an IPS mode or a VA mode utilizing vertical orientation. The driving mode of the liquid crystal display device may be a passive packing (PM) or an active packing (AM).

The liquid crystal display device of the invention can be used as a nematic curvilinear aligned phase (NCAP) device prepared by microcapsulating the liquid crystal composition, and a polymer dispersed (PD) device having a three dimensional net-work polymer formed in the liquid crystal composition, for example, a polymer network (PN) device.

EXAMPLE

The invention will be described in more detail with reference to examples, but the invention is not construed as being limited to the examples. All "%" means "% by weight" unless otherwise indicated.

The resulting compounds are identified by a nuclear magnetic resonance spectrum obtained by $^1$H-NMR analysis, a gas chromatogram obtained by gas chromatography (GC), and so forth, and the analysis methods are described below.

$^1$H-NMR Analysis

DRX-500 (produced by Bruker Biospin Co. Ltd.) was used as a measuring equipment. The measurement was carried out by dissolving a sample produced in the example in a deuterated solvent, such as $CDCl_3$, under conditions of room temperature, 500 MHz and an accumulation number of 24. In the description of the resulting nuclear magnetic resonance spectrum, "s" means a singlet, "d" means a doublet, "t" means a triplet, "q" means a quartet, and "m" means a multiplet. Tetramethylsilane (TMS) was used as a standard substance for the zero point of chemical shift δ.

GC Analysis

Gas chromatograph Model GC-14B, produced by Shimadzu Corp. was used as a measuring equipment. A capillary column CBP1-M25-025 (length: 25 m, bore: 0.22 mm, film thickness: 0.25 μm, fixed liquid phase: dimethylpolysiloxane, non-polar), produced by Shimadzu Corp. was used as a column. Helium was used as a carrier gas with a flow rate adjusted to 1 mL/min. The temperature of the sample vaporizing chamber was adjusted to 280° C., and the temperature of the detector (FID) was adjusted to 300° C.

The sample was dissolved in toluene to prepare a solution having a concentration of 1% by weight, and 1 μL of the resulting solution was injected to the sample vaporizing chamber.

The recorder used was Chromatopac Model C-R6A, produced by Shimadzu Corp. or its equivalent. A gas chromatogram obtained showed a retention time of a peak and a peak area corresponding to the component compound.

Solvents for diluting the sample may also be chloroform, hexane, and so forth. The following capillary columns may also be used: DB-1 made by Agilent Technologies Inc. (length 30 m, bore 0.32 mm, film thickness 0.25 μm), HP-1 made by Agilent Technologies Inc. (length 30 m, bore 0.32 mm, film thickness 0.25 μm), Rtx-1 made by Restek Corp. (length 30 m, bore 0.32 mm, film thickness 0.25 μm), and BP-1 made by SGE International Pty. Ltd. (length 30 m, bore 0.32 mm, film thickness 0.25 μm).

An area ratio of each peak in the gas chromatogram corresponds to a ratio of the component compound. Percentage by weight of the component compound is not completely identical to an area ratio of each peak. In the case where the aforementioned columns are used in the invention, however, the percentage by weight of the component compound substantially corresponds to the percentage of the area of each peak of the sample analyzed because the correction coefficient is substantially 1. This is because there is no significant difference in correction efficient of component compounds. In order to obtain more precisely the compositional ratio of the liquid crystal compounds in the liquid crystal composition by gas chromatogram, an internal reference method is applied to gas chromatogram. The liquid crystal compound components (components to be measured) having been precisely weighed and a standard liquid crystal compound (standard substance) are simultaneously measured by gas chromatography, and the relative intensity of the area ratio of peaks of the components to be measured and a peak of the standard substance is calculated in advance. The compositional ratio of the liquid crystal compounds in the liquid crystal composition can be precisely obtained by gas chromatography analysis by correcting using the relative intensity of the peak areas of the components with respect to the standard substance.

(Measurement Sample of Characteristics of Liquid Crystal Compounds and so Forth)

A sample to be measured for characteristics of the liquid crystal compound includes two cases, i.e., a compound itself is used as a sample, and a compound is mixed with base mixture to prepare a sample.

In the later case where a sample obtained by mixing a compound with base mixture is used, the measurement is carried out in the following manner. A sample for measurement was prepared by mixing 15% by weight of the resulting liquid crystal compound and 85% by weight of base mixture. Characteristics of the compound were calculated by extrapolating from a value obtained by the measurement according to the following equation.

extrapolated value=(100×(measured value of sample)−(weight % of base mixture)×(measured value of mother crystals))/(weight % of liquid crystal compound)

When a smectic phase or crystals are separated out at this ratio at 25° C., a ratio of the compound and base mixture was changed step by step in the order of (10% by weight/90% by weight), (5% by weight/95% by weight), (1% by weight/99% by weight), respectively. A sample having no smectic phase or crystal separated out at 25° C. was measured for characteristics, and an extrapolated value was obtained according to the aforementioned equation, which is designated as characteristics of the liquid crystal compound.

While there were various kinds of base mixture used in the measurement, the base mixture A, for example, has the following composition.

Base Mixture A:

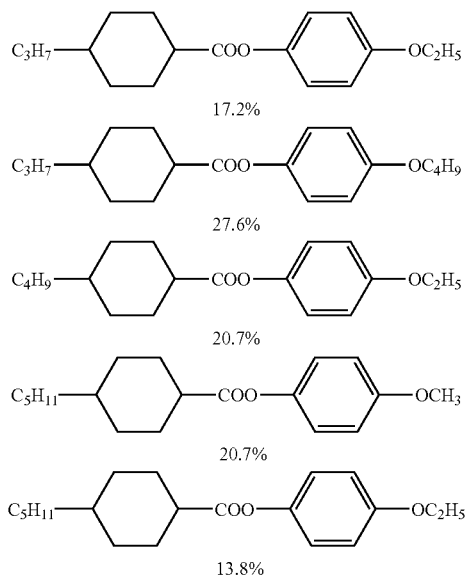

As a sample for measuring characteristics of a liquid crystal composition, a liquid crystal composition itself was used.

(Measuring Method of Characteristics of Liquid Crystal Compounds and so Forth)

Measurement of the characteristics was carried out according to the following methods. Most methods are described in the Standard of Electric Industries Association of Japan, EIAJ ED-2521A or those with some modifications. A TFT was not attached to a TN device used for measurement.

Among the measured values, values obtained with the liquid crystal compound itself as a sample and values obtained with the liquid crystal composition itself as a sample are indicated as experimental data as they are. In the case of values obtained with samples obtained by mixing a compound with base mixture, values obtained by the extrapolating method is indicated as extrapolated values.

Phase Structure and Phase Transition Temperature (° C.)

The measurement was carried out by the following methods (1) and (2).

(1) A compound was placed on a hot plate (Hot Stage Model FP-52, produced by Mettler Co., Ltd.) of a melting point measuring apparatus equipped with a polarizing microscope, and while the compound was heated at a rate of 3° C. per minute, the phase state and changes thereof were observed with the polarizing microscope to determine the kind of phase.

(2) A compound was increased and decreased in temperature at a rate of 3° C. per minute by using a scanning calorimeter DSC-7 System or Diamond DSC System, produced by Perkin-Elmer, Inc., and starting points of an endothermic peak and an exothermic peak associated with phase change of the sample were obtained by extrapolation (on set) to determine the phase change temperature.

In the following, crystals are shown by "C". In the case where crystals are distinguished, they are shown by "$C_1$" or "$C_2$". A smectic phase is shown by "S", and a nematic phase is shown by "N". A liquid (isotropic) is shown by "Iso". In the case where a smectic B phase and a smectic A phase are distinguished from each other in the smectic phase, they are shown by "$S_B$" and "$S_A$", respectively. The transition temperatures are shown, for example, by "C 50.0 N 100.0 Iso", which means that the transition temperature from crystals to a nematic phase (CN) is 50.0° C., and the transition temperature from a nematic phase to a liquid (NI) is 100.0° C. This rule is applied to the other expressions.

Maximum Temperature of Nematic Phase ($T_{NI}$; ° C.)

A sample was placed on a hot plate (Hot Stage Model FP-52, produced by Mettler Co., Ltd.) in a melting point measuring apparatus equipped with a polarizing microscope, and while the compound was heated at a rate of 1° C. per minute, the phase state and changes thereof were observed with the polarizing microscope. A temperature was measured when a part of the sample began to change from a nematic phase into an isotropic liquid. A higher limit of a temperature range of a nematic phase may be abbreviated to "a maximum temperature".

Low Temperature Compatibility

Samples were prepared by mixing base mixture and a liquid crystal compound to provide an amount of the liquid crystal compound of 20% by weight, 15% by weight, 10% by weight, 5% by weight, 3% by weight and 1% by weight, and the samples were placed in glass bottles. The glass bottles were stored in a freezer at −10° C. or −20° C. for a prescribed period of time, and then they were observed as to whether or not crystals or a smectic phase was deposited.

Viscosity (η; mPa·s, Measured at 20° C.)

A viscosity was measured by means of an E-type viscometer.

Rotation Viscosity (γ1; mPa·s, Measured at 25° C.)

A rotation viscosity was measured according to the method disclosed in M. Imai, et al., Molecular Crystals and Liquid Crystals, vol. 259, p. 37 (1995). A sample was placed in a VA device having a distance between two glass plates (cell gap) of 20 μm. The device was applied with a voltage in a range of from 30 V to 50 V stepwise by 1 V. After a period of 0.2 second with no application of voltage, voltage application was repeated with only one rectangular wave (rectangular pulse of 0.2 second) and application of no voltage (2 seconds). A peak current and a peak time of a transient current that was generated by the application of voltage were measured. A value of rotation viscosity was obtained from the measured values and the calculating formula (8) in the literature by M. Imai, et al. The value of dielectric anisotropy, which was necessary for the calculation, was obtained according to the following measuring method of dielectric anisotropy.

Optical Anisotropy (Δn; Measured at 25° C.)

Measurement was carried out with an Abbe refractometer mounting a polarizing plate on an ocular using a light at a wavelength of 589 nm at a temperature of 25° C. The surface of a main prism was rubbed in one direction, and then a sample (a liquid crystal composition or a mixture of a liquid crystal compound and base mixture) was dropped on the main prism. Refractive index (n∥) was measured when the direction of a polarized light was parallel to that of the rubbing. Refractive index (n⊥) was measured when the direction of a polarized light was perpendicular to that of the rubbing. A value of optical anisotropy was calculated from the equation;

$\Delta n = n\| - n\perp.$

Dielectric Anisotropy (Δ∈; Measured at 25° C.)

Dielectric anisotropy was measured in the following manner.

An ethanol solution (20 mL) of octadecyltriethoxysilane (0.16 mL) was coated on a glass plate having been well washed. The glass plate was rotated with a spinner and then heated to 150° C. for 1 hour. A VA device having a distance (cell gap) of 20 μm was fabricated with two glass plates.

A polyimide alignment film was prepared on a glass plate in the same manner. After rubbing the alignment film formed on the glass plate, a TN device having a distance between two glass plates of 9 μm and a twisted angle of 80° was fabricated.

A sample (a liquid crystal composition or a mixture of a liquid crystal compound and base mixture) was poured into the resulting VA device, and a voltage of 0.5 V (1 kHz, sine waves) was applied thereto to measure a dielectric constant (∈∥) in parallel to a major axis of liquid crystal molecules.

A sample (a liquid crystal composition or a mixture of a liquid crystal compound and base mixture) was poured into the resulting TN device, and a voltage of 0.5 V (1 kHz, sine waves) was applied thereto to measure a dielectric constant (∈⊥) in parallel to a major axis of liquid crystal molecules.

A value of dielectric anisotropy was calculated from the equation; $\Delta\in=\in_\parallel-\in_\perp$.

Voltage Holding Ratio (VHR; Measured at 25° C.; %)

A TN device used for measurement has a polyimide alignment film, and the cell gap between two glass plates is 6 μm. A sample (a liquid crystal composition or a mixture of a liquid crystal compound and base mixture) was poured into the device, and then the device was sealed by an adhesive which polymerized by the irradiation of ultraviolet light. The TN device was impressed and charged with pulse voltage (60 microseconds at 5 V). Decreasing voltage was measured for 16.7 milliseconds with High Speed Voltmeter and the area A between a voltage curve and a horizontal axis in a unit cycle was obtained. The area B was an area without decreasing. Voltage holding ratio is a percentage of the area A to the area B.

Examples of intermediate compounds (I) and (II) useful for producing the liquid crystal compound (1) of the invention will be described.

Example 1

Synthesis of
1-bromo-3-chloro-4-ethoxy-2-fluorobenzene (C2)

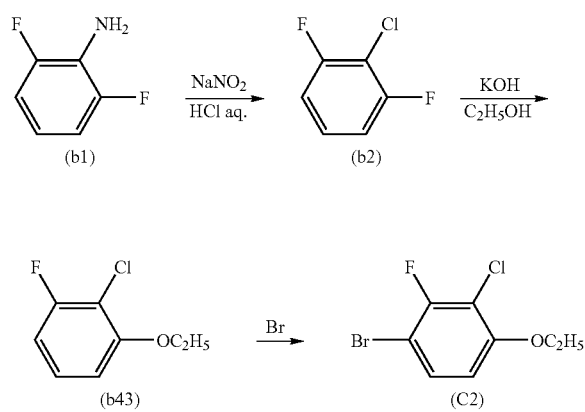

First Step 550 g of hydrochloric acid was added to a reactor having 270 g of water placed therein, and 129 g of 2,6-difluoroanyline (b1) was further added thereto, followed by stirring for 30 minutes at 60° C. Thereafter, the mixture was cooled to −10° C., and 192.5 g of a 37.6% sodium nitrite aqueous solution was added dropwise thereto over 30 minutes in a temperature range of −10 to −5° C., followed by stirring for 30 minutes at −10° C. The resulting reaction mixture was added to another reactor having 122 g of 30% hydrochloric acid and 22 g of cuprous chloride placed therein over 90 minutes in a temperature range of 25 to 30° C., followed by stirring for 30 minutes in that temperature range. A reaction mixture obtained by the reaction was subjected to steam distillation. The resulting organic phase was washed with water in three times and then dried to obtain 124 g of 2-chloro-1,3-difluorobenzene (b2).

Second Step 560 g of potassium hydroxide and 23 g of tetramethylammonium chloride (TMAC) were added to a reactor having 2,000 mL of ethanol placed therein in a temperature range of 50 to 60° C., followed by stirring for 30 minutes in that temperature range. Thereafter, the solution was heated to 80° C., and 594 g of a compound (b2) was added thereto over 1 hour in a temperature range of 80 to 85° C., followed by stirring for 5 hours at 80° C. After cooling the resulting reaction mixture to 25° C., 1,000 mL of toluene and 500 mL of water were added thereto and well mixed, and the mixture was left at rest to separate into an organic layer and an aqueous layer. After collecting the resulting organic layer, 500 mL of toluene was newly added to the aqueous mixture and well mixed, and the mixture was subjected to the same operation to extract again the compound contained in the aqueous layer. The toluene solution was added to the organic layer. After washing the organic layer with water in three times, the resulting organic layer was distilled under reduced pressure to obtain 606 g of 2-chloro-1-ethoxy-3-fluorobenzene (b43). The resulting liquid was colorless and had a boiling point of 98 to 99° C./8 mmHg.

Third Step 606 g of the compound (b43) was added to a reactor in a nitrogen atmosphere, to which 570 g of bromine was added dropwise over 1 hour in a temperature range of 20 to 40° C., followed by stirring for 30 minutes. The resulting reaction mixture was washed with a saturated sodium thiosulfate aqueous solution, a 10% sodium hydroxide aqueous solution, and water. The resulting reaction mixture having been washed was subjected to fractional distillation under reduced pressure to obtain 760 g of 1-bromo-3-chloro-4-ethoxy-2-fluorobenzene (C2). The resulting compound (C2) was white solid and had a melting point of 65.4 to 66.1° C. and a boiling point of 125 to 127° C./8 mmHg.

The resulting compound exhibited the following chemical shift δ (ppm) of $^1$H-NMR analysis, and thus the compound was identified as 1-bromo-3-chloro-4-ethoxy-2-fluorobenzene. The measuring solvent was CDCl$_3$.

Chemical shift δ (ppm): 7.35 (t, 1H), 6.62 (dd, 1H), 4.09 (q, 2H), 1.48 (t, 3H)

Example 2

Synthesis of
1-bromo-2-chloro-4-ethoxy-3-fluorobenzene (C12)

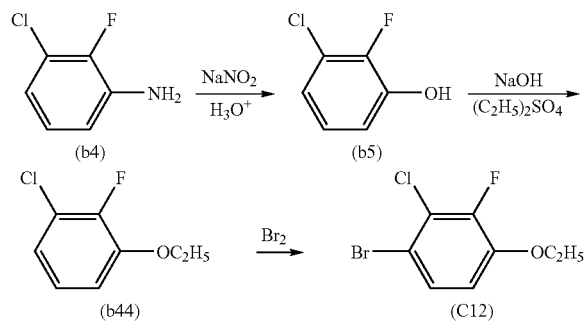

First Step 728 g of 3-chloro-2-fluoroaniline was added to a reactor having 6,860 g of 30.6% sulfuric acid placed therein, followed by stirring for 30 minutes at 80° C. Thereafter, the mixture was cooled to −10° C., and 952 g of a 37.0% sodium nitrite aqueous solution was added dropwise thereto over 90 minutes in a temperature range of −10 to −5° C., followed by stirring for 30 minutes in that temperature range. The resulting reaction mixture was added to another reactor having 4,100 g of 51.2% sulfuric acid, 1,500 g of copper sulfate and 3,000 mL of toluene placed therein over 6 hours in a temperature range of 80 to 85° C., followed by stirring for 30 minutes in that temperature range. The resulting reaction mixture was cooled to a temperature range of 70 to 75° C. and left at rest to separate into two layers, i.e., an organic layer and an aqueous layer, and the organic layer was collected. The aqueous layer was cooled to 20° C., and copper sulfate was filtered off, followed by extracting with 1,200 mL toluene twice. The organic layer obtained by extraction was washed with 700 mL of water and subjected to fractional distillation to obtain 300 g of 3-chloro-2-fluorophenol (b5). The compound had a boiling point of 60 to 62° C./1 mmHg.

Second Step

The compound (b5) was added dropwise to a reactor having 1,200 g of a 10% sodium hydroxide aqueous solution placed therein over 30 minutes in a temperature range of 20 to 40° C. Thereafter, 462 g of diethyl sulfate was added dropwise thereto over 1 hour in a temperature range of 25 to 35° C., followed by stirring for 5 hours in that temperature range. The resulting organic layer was collected and washed with 200 mL of water in three times, followed by drying, to obtain 505 g of 1-chloro-3-ethoxy-2-fluorobenzene (b44). The resulting liquid was colorless.

Third Step 504 g of the compound (b44) was added to a reactor in a nitrogen atmosphere, to which 434 g of bromine was added dropwise over 1 hour in a temperature range of 20 to 40° C., followed by stirring for 30 minutes. The resulting reaction mixture was washed with a saturated sodium thiosulfate aqueous solution, a 10% sodium hydroxide aqueous solution, and water. The residue was subjected to fractional distillation under reduced pressure to obtain 605 g of 1-bromo-2-chloro-4-ethoxy-3-fluorobenzene (C12). The resulting compound (C12) was white solid and had a melting point of 48.0 to 48.5° C. and a boiling point of 88 to 90° C./1 mmHg.

The resulting compound exhibited the following chemical shift δ (ppm) of $^1$H-NMR analysis, and thus the compound was identified as 1-bromo-2-chloro-4-ethoxy-3-fluorobenzene. The measuring solvent was $CDCl_3$.

Chemical shift δ (ppm): 7.31 (dd, 1H), 6.77 (t, 1H), 4.09 (q, 2H), 1.45 (t, 3H)

Example 3

The following compounds (C1), (C3) to (C11) and (C13) to (C20) were synthesized in the same method as the synthesis methods described in Examples 1 and 2. The compounds (C2) and (C12) obtained in Examples 1 and 2 are also described in the following. The values shown with the compounds are values measured in the aforementioned methods, in which "m.p." shows a melting point, and "b.p." shows a boiling point.

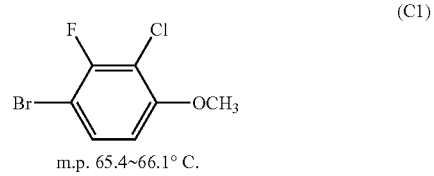

m.p. 65.4~66.1° C.

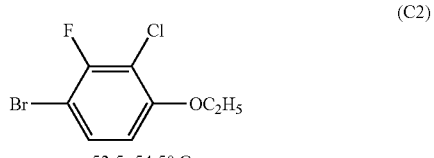

m.p. 53.5~54.5° C.

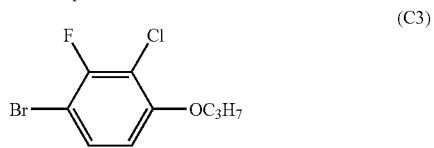

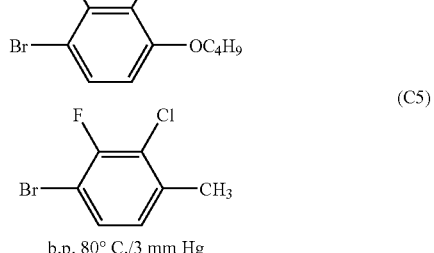

b.p. 80° C./3 mm Hg

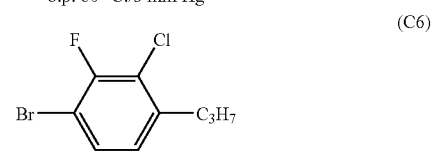

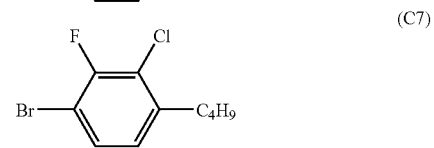

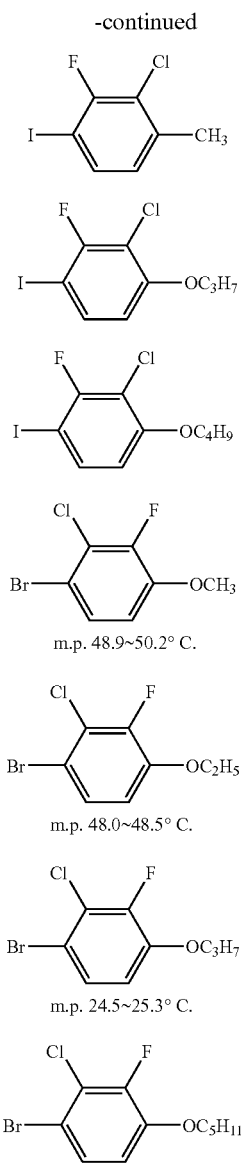
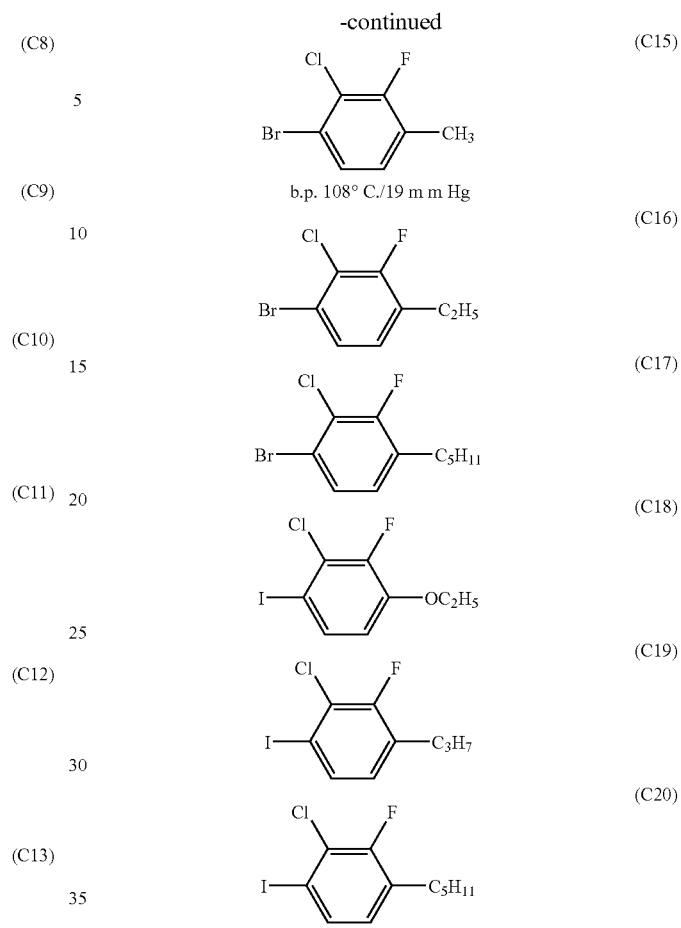
Examples of the liquid crystal compound (1) of the invention produced by using the compounds (C1) to (C20) synthesized in Examples 1, 2 and 3 will be described.
Example 4
Synthesis of trans-4'-(3-chloro-4-ethoxy-2-fluorophenyl)-trans-4-propyl-bicyclohexyl (C28)
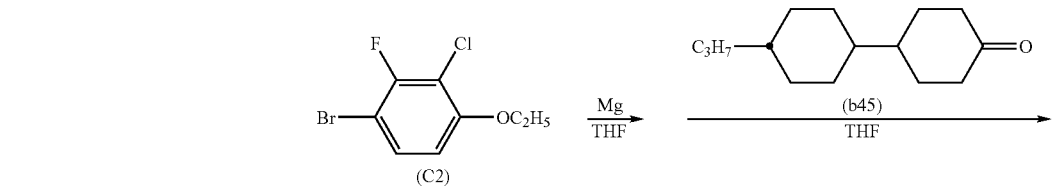
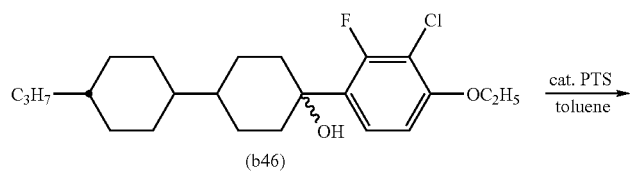

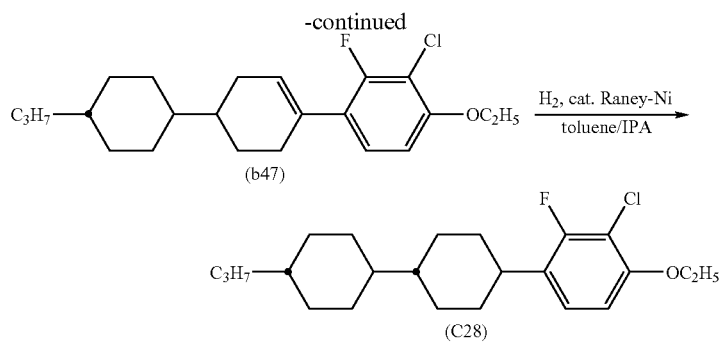

(b47)

(C28)

First Step 2.6 g of well dried magnesium and 20 mL of THF were added to a reactor in a nitrogen atmosphere and heated to 40° C. 26.6 g of the compound (C2) dissolved in 80 mL of THF was added dropwise thereto slowly in a temperature range of 30 to 45° C., followed by stirring for 30 minutes. Thereafter, 22.2 g of 4'-propyl-bicyclohexyl-4-one (b45) dissolved in 40 mL of THF was added dropwise thereto slowly in a temperature range of 30 to 50° C., followed by stirring for 60 minutes. The resulting reaction mixture was cooled to 25° C. and then poured into 100 mL of 3N hydrochloric acid and 100 mL of toluene, followed by mixing. The mixture was then left to rest to separate into an organic layer and an aqueous layer, followed by extracting. The resulting organic layer was collected and washed with water, a 2N sodium hydroxide aqueous solution, a saturated sodium hydrogen carbonate aqueous solution and water, followed by drying over anhydrous magnesium sulfate. Thereafter, the solvent was distilled off under reduced pressure to obtain 45.8 g of 4-(3-chloro-4-ethoxy-2-fluorophenyl)-trans-4'-propyl-bicyclohexyl-4-ol (b46). The resulting compound (b46) was a yellow oily substance.

Second Step 45.8 g of the compound (b46), 0.5 g of p-toluenesulfonic acid and 150 mL of toluene were mixed, and the mixture was refluxed under heating for 1 hour while removing distilled water. After cooling the reaction mixture to 25° C., 200 mL of water and 100 mL of toluene was added to the resulting liquid, and the mixture was left at rest to separate into an organic layer and an aqueous layer, followed by extracting to the organic layer. The resulting organic layer was collected and washed with a 2N sodium hydroxide aqueous solution, a saturated sodium hydrogen carbonate aqueous solution and water, followed by drying over anhydrous magnesium sulfate. Thereafter, the solvent was distilled off under reduced pressure to obtain a residue. The residue was purified by preparative column chromatography using a mixed solvent of heptane and toluene (heptane/toluene=2/1 by volume) as a developing solvent and silica gel as a mediator, and further purified by recrystallization from a mixed solvent of heptane and ethanol (heptane/ethanol=2/1 by volume) to obtain 28.5 g of 4-(3-chloro-4-ethoxy-2-fluorophenyl)-trans-4'-propyl-bicyclohexyl-3-ene (b47). The yield was 68.4% based on the compound (b45).

The transition temperatures of the resulting compound (b47) were as follows.

Transition temperature: $C_1$ 65.4 $C_2$ 81.1 $C_3$ 88.9 $S_A$ 121.5 N 160.2 Iso The resulting compound exhibited the following chemical shift δ (ppm) of $^1$H-NMR analysis, and thus the compound was identified as 4-(3-chloro-4-ethoxy-2-fluorophenyl)-trans-4'-propyl-bicyclohexyl-3-ene. The measuring solvent was CDCl$_3$.

Chemical shift δ (ppm): 7.04 (t, 1H), 6.64 (dd, 1H), 5.87 (t, 1H), 4.09 (q, 2H), 2.38-0.86 (m, 27H)

Third Step 20.8 g of the compound (b47) was dissolved in a mixed solvent of 80 mL of toluene and 80 mL of isopropyl alcohol, to which 2.0 g of Raney-Ni was added, followed by stirring in a hydrogen atmosphere at room temperature until no hydrogen was absorbed. After completing the reaction, Raney-Ni was removed, the solvent was distilled off, and the residue was purified by a preparative column chromatography using a mixed solvent of heptane and toluene (heptane/toluene=4/1 by volume) as a developing solvent and silica gel as a mediator, and further purified by recrystallization from a mixed solvent of heptane and ethanol (heptane/ethanol=2/1 by volume) to obtain 13.8 g of trans-4'-(3-chloro-4-ethoxy-2-fluorophenyl)-trans-4-propyl-bicyclohexyl (C28). The resulting compound (C28) was colorless crystals, and the yield was 65.8% based on the compound (b47).

The transition temperatures of the resulting compound (C28) were as follows.

Transition temperature: C 105.5 $S_B$ 16.0 N 168.9 Iso

The resulting compound exhibited the following chemical shift δ (ppm) of $^1$H-NMR analysis, and thus the compound was identified as trans-4'-(3-chloro-4-ethoxy-2-fluorophenyl)-trans-4-propyl-bicyclohexyl. The measuring solvent was CDCl$_3$.

Chemical shift δ (ppm): 7.01 (t, 1H), 6.65 (dd, 1H), 4.08 (q, 2H), 2.72 (tt, 1H), 1.88-0.82 (m, 29H)

Example 5

Synthesis of trans-4'-(2-chloro-4-ethoxy-3-fluorophenyl)-trans-4-propyl-bicyclohexyl (C44)

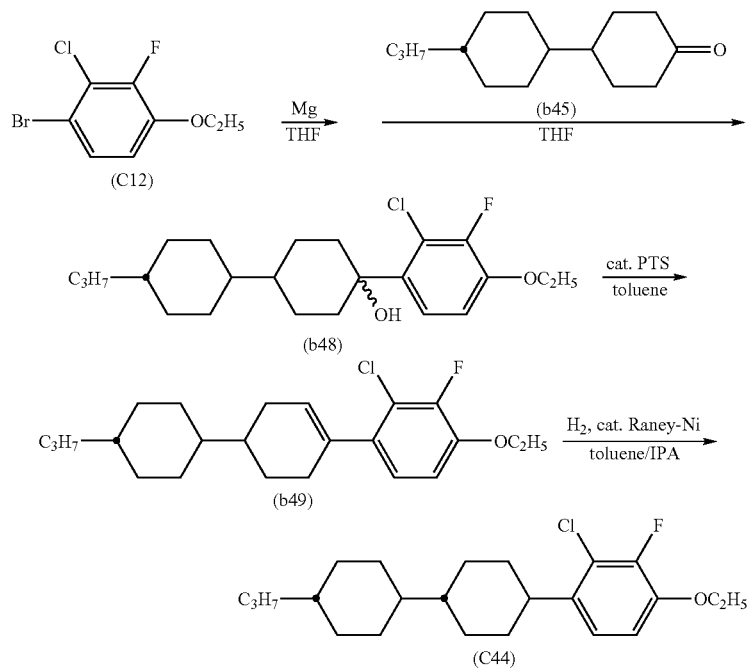

First Step 2.6 g of well dried magnesium and 20 mL of THF were added to a reactor in a nitrogen atmosphere and heated to 40° C. 26.6 g of the compound (C12) dissolved in 80 mL of THF was added dropwise thereto slowly in a temperature range of 30 to 45° C., followed by stirring for 20 minutes. Thereafter, 21.2 g of a compound (b45) dissolved in 20 mL of THF was added dropwise thereto slowly in a temperature range of 30 to 35° C., followed by stirring for 60 minutes. The resulting reaction mixture was cooled to 25° C. and then poured into 100 mL of 3N hydrochloric acid and 100 mL of toluene, followed by mixing. The mixture was then left to rest to separate into an organic layer and an aqueous layer, followed by extracting to the organic layer. The resulting organic layer was collected and washed with water, a 2N sodium hydroxide aqueous solution, a saturated sodium hydrogen carbonate aqueous solution and water, followed by drying over anhydrous magnesium sulfate. Thereafter, the solvent was distilled off under reduced pressure to obtain 47.0 g of 4-(2-chloro-4-ethoxy-3-fluorophenyl)-trans-4'-propyl-bicyclohexyl-4-ol (b48). The resulting compound (b48) was a yellow oily substance.

Second Step 47.0 g of the compound (b48), 1.0 g of p-toluenesulfonic acid and 200 mL of toluene were mixed, and the mixture was refluxed under heating for 1 hour while removing distilled water. After cooling the reaction mixture to 25° C., 200 mL of water and 200 mL of toluene was added to the resulting liquid, and the mixture was left at rest to separate into an organic layer and an aqueous layer, followed by extracting to the organic layer. The resulting organic layer was collected and washed with a 2N sodium hydroxide aqueous solution, a saturated sodium hydrogen carbonate aqueous solution and water, followed by drying over anhydrous magnesium sulfate. Thereafter, the solvent was distilled off under reduced pressure to obtain a residue. The residue was purified by a preparative column chromatography using a mixed solvent of heptane and toluene (heptane/toluene=4/1 by volume) as a developing solvent and silica gel as a mediator, and further purified by recrystallization from a mixed solvent of heptane and ethanol (heptane/ethanol=2/1 by volume) to obtain 19.4 g of 4-(2-chloro-4-ethoxy-3-fluorophenyl)-trans-4'-propyl-bicyclohexyl-3-ene (b49). The yield was 53.6% based on the compound (b45)

The transition temperatures of the resulting compound (b49) were as follows.

Transition temperature: C 71.1 N 130.3 Iso

The resulting compound exhibited the following chemical shift δ (ppm) of $^1$H-NMR analysis, and thus the compound was identified as 4-(2-chloro-4-ethoxy-3-fluorophenyl)-trans-4'-propyl-bicyclohexyl-3-ene. The measuring solvent was $CDCl_3$.

Chemical shift δ (ppm): 6.85-6.77 (m, 2H), 5.65 (t, 1H), 4.09 (q, 2H), 2.36-0.86 (m, 27H)

Third Step 17.0 g of the compound (b49) was dissolved in a mixed solvent of 50 mL of toluene and 100 mL of isopropyl alcohol, to which 1.7 g of Raney-Ni was added, followed by stirring in a hydrogen atmosphere at room temperature until no hydrogen was absorbed. After completing the reaction, Raney-Ni was removed, the solvent was distilled off, and the residue was purified by a preparative column chromatography using a mixed solvent of heptane and toluene (heptane/toluene=4/1 by volume) as a developing solvent and silica gel as a mediator, and further purified by recrystallization from a mixed solvent of heptane and ethanol (heptane/ethanol=2/1 by volume) to obtain 6.8 g of trans-4'-(2-chloro-4-ethoxy-3-fluorophenyl)-trans-4-propyl-bicyclohexyl (C40). The resulting compound (C40) was colorless crystals, and the yield was 39.6% based on the compound (b49).

The transition temperatures of the resulting compound (C44) were as follows.

Transition temperature: C 89.9 N 152.9 Iso

The resulting compound exhibited the following chemical shift δ (ppm) of $^1$H-NMR analysis, and thus the compound was identified as trans-4'-(2-chloro-4-ethoxy-3-fluorophenyl)-trans-4-propyl-bicyclohexyl. The measuring solvent was $CDCl_3$.

Chemical shift δ (ppm): 6.92 (dd, 1H), 6.83 (t, 1H), 4.08 (q, 2H), 2.84 (tt, 1H), 1.90-0.83 (m, 29H)

Example 6

Synthesis of trans-4'-(2-(3-chloro-4-ethoxy-2-fluorophenyl)-vinyl)-trans-4-propyl-bicyclohexyl (C58)

fluorophenyl)-2-(trans-4'-propyl-bicyclohexyl-trans-4-yl)-ethanol (b51). The resulting compound (b51) was a yellow oily substance.

Second Step 33.0 g of the compound (b51), 1.0 g of p-toluenesulfonic acid and 150 mL of toluene were mixed, and the mixture was refluxed under heating for 1 hour while removing distilled water. After cooling the reaction mixture to 30° C., 200 mL of water and 100 mL of toluene was added to the resulting liquid, and the mixture was left at rest to separate into an organic layer and an aqueous layer, followed by extracting to the organic layer. The resulting organic layer was collected and washed with a 2N sodium hydroxide aqueous solution, a saturated sodium hydrogen carbonate aqueous solution and water, followed by drying over anhydrous magnesium sulfate. Thereafter, the solvent was distilled off under reduced

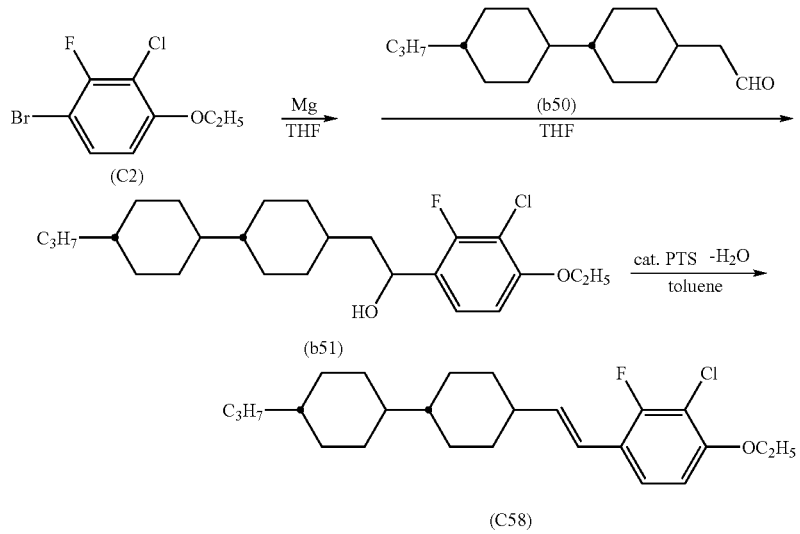

First Step 1.92 g of well dried magnesium and 20 mL of THF were added to a reactor in a nitrogen atmosphere and heated to 45° C. 20.0 g of the compound (C2) dissolved in 80 mL of THF was added dropwise thereto over 60 minutes in a temperature range of 45 to 55° C., followed by stirring for 10 minutes. Thereafter, 18.0 g of (trans-4'-bicyclohexyl-trans-4-yl)-aldehyde (b50) dissolved in 20 mL of THF was added dropwise thereto over 60 minutes in a temperature range of 50 to 55° C., followed by stirring for 60 minutes. The resulting reaction mixture was cooled to 25° C. and then poured into 100 mL of 3N hydrochloric acid and 100 mL of toluene, followed by mixing. The mixture was then left to rest to separate into an organic layer and an aqueous layer, followed by extracting to the organic layer. The resulting organic layer was collected and washed with water, a 2N sodium hydroxide aqueous solution, a saturated sodium hydrogen carbonate aqueous solution and water, followed by drying over anhydrous magnesium sulfate. Thereafter, the solvent was distilled off under reduced pressure to obtain 33.0 g of 1-(3-chloro-4-ethoxy-2- pressure to obtain a residue. The resulting residue was purified by a preparative column chromatography using a mixed solvent of heptane and toluene (heptane/toluene=4/1 by volume) as a developing solvent and silica gel as a mediator, and further purified by recrystallization from a mixed solvent of heptane and ethanol (heptane/ethanol=2/1 by volume) to obtain 22.3 g of trans-4'-(2-(3-chloro-4-ethoxy-2-fluorophenyl)-vinyl)-trans-4-propyl-bicyclohexyl (C58). The resulting compound (C58) was colorless crystals, and the yield was 76.4% based on the compound (b50).

The transition temperatures of the resulting compound (C58) were as follows.

Transition temperature: $C_1$ 83.6 $C_2$ 88.9 $S_A$ 125.6 N 224.8 Iso

The resulting compound exhibited the following chemical shift δ (ppm) of $^1$H-NMR analysis, and thus the compound was identified as trans-4'-(2-(3-chloro-4-ethoxy-2-fluorophenyl)-vinyl)-trans-4-propyl-bicyclohexyl. The measuring solvent was $CDCl_3$.

Chemical shift δ (ppm): 7.24 (t, 1H), 6.65 (dd, 1H), 6.39 (d, 1H), 6.11 (q, 1H), 4.10 (q, 2H), 2.08-0.81 (m, 30H)

Example 7

Synthesis of trans-4'-(2-(2-chloro-4-ethoxy-3-fluorophenyl)-ethyl)-trans-4-propyl-bicyclohexyl (C96)

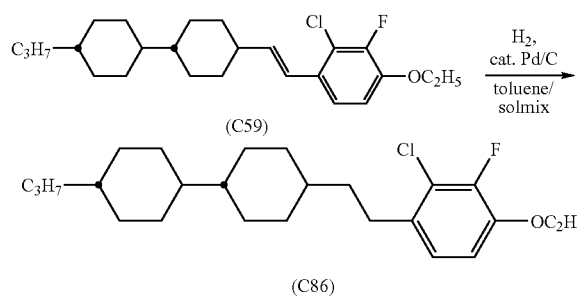

18.0 g of trans-4'-(2-(2-chloro-4-ethoxy-3-fluorophenyl)-vinyl)-trans-4-propyl-bicyclohexyl (C67) was dissolved in a mixed solvent of 80 mL of toluene and 40 mL of Solmix A-11 (available from Nippon Alcohol Hanbai K.K.), to which 0.5 g of Pd/C was further added, and the mixture was stirred in a hydrogen atmosphere at room temperature until no hydrogen was absorbed. After completing the reaction, Pd/C was removed, the solvent was distilled off, and the residue was purified by a preparative column chromatography using a mixed solvent of heptane and toluene (heptane/toluene=4/1 by volume) as a developing solvent and silica gel as a mediator, and further purified by recrystallization from a mixed solvent of heptane and ethanol (heptane/ethanol=2/1 by volume) to obtain 9.1 g of trans-4'-(2-(2-chloro-4-ethoxy-3-fluorophenyl)-ethyl)-trans-4-propyl-bicyclohexyl (C96). The resulting compound (C96) was colorless crystal, and the yield was 49.3% based on the compound (C67).

The transition temperatures of the resulting compound (C96) were as follows.

Transition temperature: C 63.5 N 153.1 Iso

The resulting compound exhibited the following chemical shift δ (ppm) of $^1$H-NMR analysis, and thus the compound was identified as trans-4'-(2-(2-chloro-4-ethoxy-3-fluorophenyl)-ethyl)-trans-4-propyl-bicyclohexyl. The measuring solvent was CDCl$_3$.

Chemical shift δ (ppm): 6.88 (dd, 1H), 6.79 (t, 1H), 4.08 (q, 2H), 2.65 (t, 2H), 1.83-0.80 (m, 32H)

Example 8

Synthesis of trans-4'-(3-chloro-4-ethoxy-2-fluorophenyl)-trans-4-vinyl-bicyclohexyl (C115)

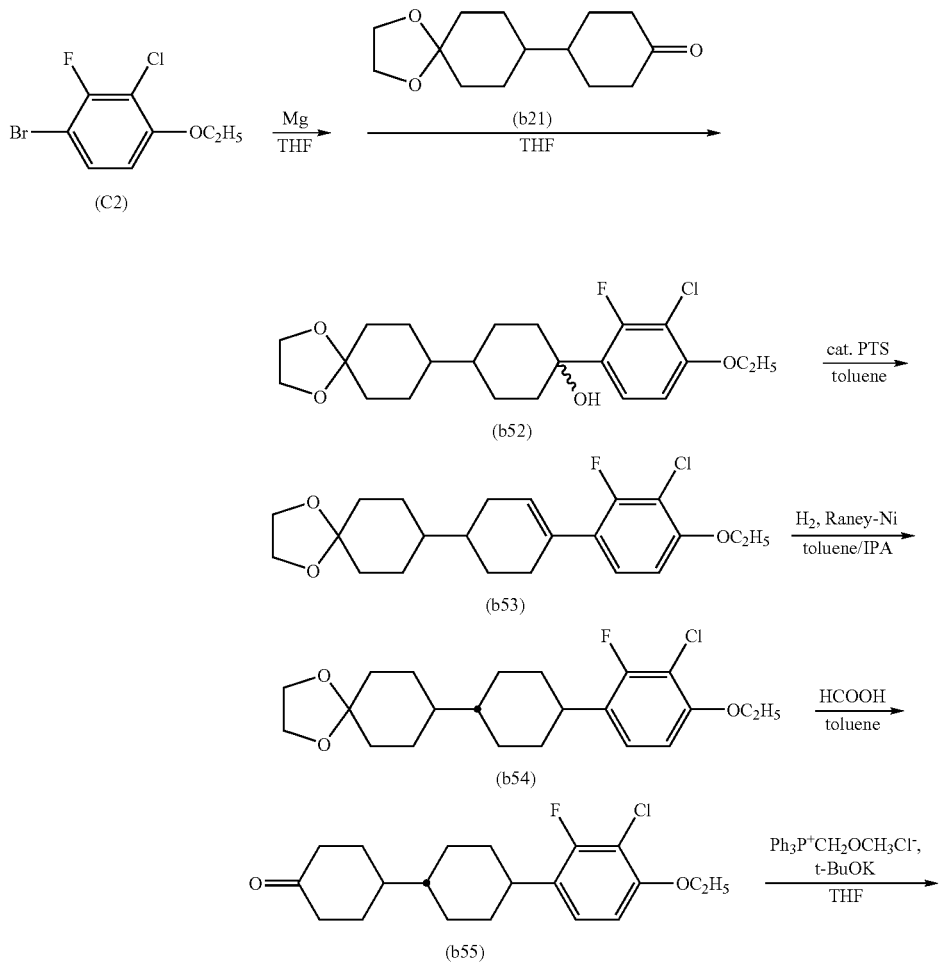

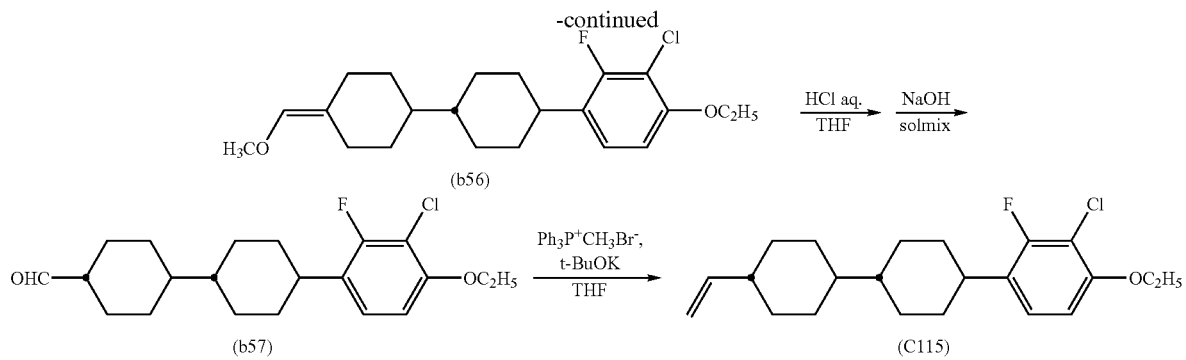
(b56)
(b57)
(C115)

First Step 4.8 g of well dried magnesium and 150 mL of THF were added to a reactor in a nitrogen atmosphere and heated to 47° C. 50.0 g of the compound (C2) dissolved in 50 mL of THF was added dropwise thereto slowly in a temperature range of 50 to 57° C., followed by stirring for 60 minutes. Thereafter, 39.2 g of a compound (b21) dissolved in 80 mL of THF was added dropwise thereto slowly in a temperature range of 47 to 58° C., followed by stirring for 60 minutes. The resulting reaction mixture was cooled to 25° C. and then poured into 200 mL of a 13% ammonium chloride aqueous solution and 500 mL of toluene. The resulting mixture was then left to rest to separate into an organic layer and an aqueous layer, followed by extracting to the organic layer. The resulting organic layer was collected and washed with water, a 2N sodium hydroxide aqueous solution, a saturated sodium hydrogen carbonate aqueous solution and water, followed by drying over anhydrous magnesium sulfate. Thereafter, the solvent was distilled off under reduced pressure to obtain 84.7 g of 1-(3-chloro-4-ethoxy-2-fluorophenyl)-4-(1,4-dioxa-spiro[4.5]dec-8-yl)cyclohexanol (b52).

Second Step 84.7 g of the compound (b52), 1.0 g of p-toluenesulfonic acid, 1.3 g of ethylene glycol and 320 mL of toluene were mixed, and the mixture was refluxed under heating for 2 hours while removing distilled water. After cooling the reaction mixture to 25° C., 300 mL of 3% sodium hydrogen carbonate aqueous solution and 200 mL of toluene was added to the resulting liquid, and the mixture was left at rest to separate into an organic layer and an aqueous layer, followed by extracting to the organic layer. The resulting organic layer was collected and washed with a 2N sodium hydroxide aqueous solution, a saturated sodium hydrogen carbonate aqueous solution and water, followed by drying over anhydrous magnesium sulfate. Thereafter, the solvent was distilled off under reduced pressure to obtain a residue. The resulting residue was purified by a preparative column chromatography using toluene as a developing solvent and silica gel as a mediator, and further purified by recrystallization from a mixed solvent of heptane and toluene (heptane/toluene=2/1 by volume) to obtain 50.2 g of 8-(4-(3-chloro-4-ethoxy-2-fluorophenyl)-cyclohexa-3-enyl)-1,4-dioxa-spiro[4.5]decane (b53). The yield was 77.3% based on the compound (b21).

Third Step 50.2 g of the compound (b53) was dissolved in a mixed solvent of 250 mL of toluene and 250 mL of isopropyl alcohol, to which 5.0 g of Raney-Ni was added, followed by stirring in a hydrogen atmosphere at room temperature until no hydrogen was absorbed. After completing the reaction, Raney-Ni was removed, and the solvent was distilled off to obtain 52.5 g of 8-(4-(3-chloro-4-ethoxy-2-fluorophenyl)-cyclohexyl)-1,4-dioxa-spiro[4.5]decane (b54) as a crude material.

Fourth Step 52.5 g of the compound (b54) was dissolved in 250 mL of toluene, to which 20.7 g of an 88% formic acid aqueous solution was added. The mixture was refluxed under heating for 6 hours. The reaction mixture was cooled to 25° C. and poured into a mixed solution of 300 mL of water and 200 mL of toluene. They were mixed and then left at rest to separate into an organic layer and an aqueous layer, followed by extracting to the organic layer. The resulting organic layer was collected and washed with a saturated sodium hydrogen carbonate aqueous solution and water, followed by drying over anhydrous magnesium sulfate. Thereafter, the solvent was distilled off under reduced pressure to obtain a residue. The resulting residue was purified by recrystallization from a mixed solvent of heptane and toluene (heptane/toluene=1/1 by volume) to obtain 19.9 g of trans-4'-(3-chloro-4-ethoxy-2-fluorophenyl)-bicyclohexyl-4-one (b55). The yield was 44.4% based on the compound (b53).

Fifth Step 22.2 g of methoxymethyltriphenylphosphonium chloride was added to 60 mL of THF and cooled to −20° C. 7.0 g of potassium t-butoxide (t-BuOK) was added to the resulting mixed solution in a temperature range of −20 to −10° C., followed by stirring for 30 minutes. Thereafter, 19.0 g of the compound (b55) dissolved in 40 mL of toluene was added dropwise thereto over 60 minutes in a temperature range of −15 to −5° C., followed by stirring for 30 minutes. After restoring the temperature of the reaction mixture to 0° C., a mixed solution of 100 mL of water and 200 mL of toluene was poured thereto. They were mixed and then left at rest to separate into an organic layer and an aqueous layer, followed by extracting to the organic layer. The resulting organic layer was collected and washed with water, followed by drying over anhydrous magnesium sulfate. Thereafter, the solvent was distilled off under reduced pressure to obtain a residue. The resulting residue was purified by a preparative column chromatography using a mixed solvent of heptane and toluene (heptane/toluene=1/1 by volume) as a developing solvent and silica gel as a mediator to obtain 20.1 g of trans-4'-(3-chloro-4-ethoxy-2-fluorophenyl)-4-methoxymethylene-bicyclohexyl (b56). The yield was 98.0% based on the compound (b55).

Sixth Step 20.1 g of the compound (b56) was dissolved in 160 mL of THF, and the mixture was stirred at 30° C. 40 mL of 3N hydrochloric acid was added to the mixture, which was further stirred for 120 minutes. The resulting reaction mixture was poured into a mixed solution of 200 mL of water and 300 mL of toluene. It was mixed and then left at rest to separate into an organic layer and an aqueous layer, followed by extracting to the organic layer. The resulting organic layer was collected and washed with a saturated sodium hydrogen carbonate aqueous solution and water, followed by drying over anhydrous magnesium sulfate. Thereafter, the solvent was distilled off under reduced pressure to obtain 22.0 g of a residue. 22.0 g of the resulting residue was dissolved in 60 mL of toluene, and the resulting solution was poured into 240 mL of methanol having 0.2 g of sodium hydroxide dissolved therein, followed by stirring for 3 hours at 5° C. The resulting reaction mixture was extracted with 400 mL of toluene, and the resulting organic layer was washed with water, followed by drying over anhydrous magnesium sulfate. Thereafter, the solvent was distilled off under reduced pressure to obtain 20.1 of a residue. The residue was purified by recrystallization from a mixed solvent of heptane and toluene (heptane/toluene=1/1 by volume) to obtain 13.9 g of trans-4'-(3-chloro-4-ethoxy-2-fluorophenyl)-bicyclohexyl-trans-4-carbaldehyde (b57). The yield was 71.9% based on the compound (b56).

Seventh Step 4.7 g of methyltriphenylphosphonium bromide was added to 20 mL of THF and cooled to 5° C. 1.4 g of potassium t-butoxide (t-BuOK) was added to the resulting mixed solution in a temperature range of 5 to 10° C., followed by stirring for 30 minutes. Thereafter, 4.0 g of the compound (b57) dissolved in 20 mL of toluene was added dropwise thereto over 30 minutes in a temperature range of 5 to 10° C., followed by stirring for 30 minutes. The reaction mixture was poured into a mixed solution of 50 mL of water and 40 mL of toluene. They were mixed and then left at rest to separate into an organic layer and an aqueous layer, followed by extracting to the organic layer. The resulting organic layer was collected and washed with water, followed by drying over anhydrous magnesium sulfate. Thereafter, the solvent was distilled off under reduced pressure to obtain a residue. The resulting residue was purified by a preparative column chromatography using a mixed solvent of heptane and toluene (heptane/toluene=2/1 by volume) as a developing solvent and silica gel as a mediator, and further purified by recrystallization from a mixed solvent of heptane and ethanol (heptane/ethanol=2/1 by volume) to obtain 3.2 g of trans-4'-(3-chloro-4-ethoxy-2-fluorophenyl)-trans-4-vinyl-bicyclohexyl (C115). The yield was 79.4% based on the compound (b57)

The transition temperatures of the resulting compound (C115) were as follows.

Transition temperature: C 113.4 N 151.9 Iso

The resulting compound exhibited the following chemical shift δ (ppm) of $^1$H-NMR analysis, and thus the compound was identified as trans-4'-(3-chloro-4-ethoxy-2-fluorophenyl)-trans-4-vinyl-bicyclohexyl. The measuring solvent was CDCl$_3$.

Chemical shift δ (ppm): 7.03 (t, 1H), 6.66 (dd, 1H), 5.78 (m, 1H), 4.95 (dt, 1H), 4.89 (dt, 1H), 4.08 (q, 2H), 2.73 (tt, 1H), 1.82 (m, 9H), 1.47-1.37 (m, 5H), 1.21-1.10 (m, 8H)

Example 9

Synthesis of 3-choloro-4-ethoxy-2-fluoro-4'-(trans-4-propyl-cyclohexyl)biphenyl (C154)

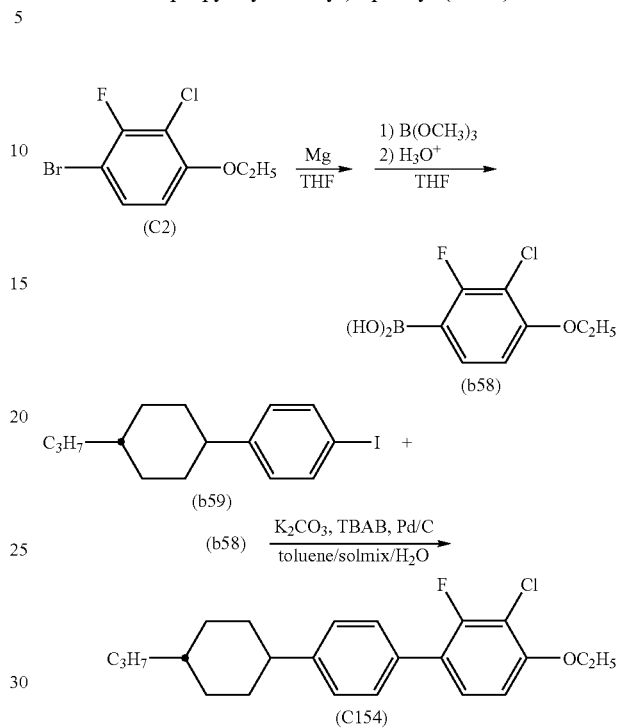

First Step 4.79 g of well dried magnesium and 50 mL of THF were added to a reactor in a nitrogen atmosphere and heated to 50° C. 50.0 g of the compound (C2) dissolved in 200 mL of THF was added dropwise thereto over 60 minutes in a temperature range of 43 to 48° C., followed by stirring for 60 minutes. The resulting reaction mixture was cooled to 25° C. Thereafter, the reaction mixture was added dropwise to a solution of 24.6 g of trimethyl borate and 100 mL of THF cooled to −50° C. over 60 minutes in a nitrogen atmosphere in a temperature range of −60 to −40° C. The reaction mixture was warmed to 0° C. and then poured into 400 mL of 3N hydrochloric acid at 0° C. 700 mL of acetic acid was added to the solution, followed by mixing, and the mixture was then left to rest to separate into an organic layer and an aqueous layer, followed by extracting. The resulting organic layer was collected and washed with a saturated sodium hydrogen carbonate aqueous solution and water, followed by drying over anhydrous magnesium sulfate. Thereafter, the solvent was distilled off under reduced pressure to obtain a residue. The residue was recrystallized from heptane. The recrystallization operation was repeated to obtain 35.9 g of 3-chloro-4-ethoxy-2-fluorophenylboronic acid (b58). The resulting compound (b58) was a yellowish solid.

Second Step 15.0 g of the compound (b58), 15 g of 1-iodo-4-(trans-4-propylcyclohexyl)-benzene (b59), 19.0 g of potassium carbonate, 7.37 g of tetrabutylammonium bromide (TBAB) and 0.39 g of Pd/C were added to a reactor having 50 mL of toluene, 50 mL of Solmix A-11 and 2.5 mL of water placed therein. The mixture was refluxed under heating and stirring for 4 hours. After cooling the reaction mixture to 25° C., potassium carbonate and Pd/C were filtered off. 100 mL of toluene was added to the resulting solution, which was washed with a 2N sodium hydroxide aqueous solution, a saturated sodium thiosulfate aqueous solution and water. Thereafter, the solvent was distilled off under reduced pressure to obtain a residue. The residue was dissolved in a mixed solvent of ethyl acetate and Solmix A-11 (ethyl acetate/Solmix A-11=2/1 by volume) and recrystallized therefrom. The recrystallization operation was repeated to obtain 17.1 g of a yellowish solid. The solid was dissolved in a mixed solvent of 80 mL of toluene and 20 mL of Solmix A-11, to which 0.5 g of Pd/C was added, followed by stirring for 15 hours in a hydrogen atmosphere at 20° C. After removing Pd/C from the reaction mixture by filtration, the reaction mixture was washed with a 2N sodium hydroxide aqueous solution, a saturated sodium thiosulfate aqueous solution and water, followed by drying over anhydrous magnesium sulfate. Thereafter, the solvent was distilled off under reduced pressure to obtain a residue. The resulting residue was purified by a preparative column chromatography using a mixed solvent of heptane and toluene (heptane/toluene=2/1 by volume) as a developing solvent and silica gel as a mediator, and further purified by recrystallization from a mixed solvent of ethyl acetate and ethanol (ethyl acetate/ethanol=2/1 by volume), followed by drying, to obtain 14.9 g of 3-choloro-4-ethoxy-2-fluoro-4'-(trans-4-propyl-cyclohexyl)biphenyl (C154). The resulting compound (C154) was colorless crystals, and the yield was 86.9% based on the compound (b59).

The transition temperatures of the resulting compound (C154) were as follows.

Transition temperature: C 114.8 N 157.7 Iso

The resulting compound exhibited the following chemical shift δ (ppm) of $^1$H-NMR analysis, and thus the compound was identified as 3-choloro-4-ethoxy-2-fluoro-4'-(trans-4-propyl-cyclohexyl)biphenyl. The measuring solvent was $CDCl_3$.

Chemical shift δ (ppm): 7.42 (d, 2H), 7.28-7.23 (m, 3H) 6.77 (dd, 1H), 4.14 (q, 2H), 2.50 (tt, 1H), 1.94-0.89 (m, 19H)

Example 10

Synthesis of 3-chloro-4-ethoxy-2-fluoro-4"-propyl-[1,1';4',1"]terphenyl (C195)

heating and stirring for 9 hours. After cooling the reaction mixture to 25° C., potassium carbonate and $Pd(PPh_3)_2Cl$ were filtered off. 100 mL of toluene was added to the resulting solution, which was washed with a 2N sodium hydroxide aqueous solution, a saturated sodium thiosulfate aqueous solution and water. Thereafter, the solvent was distilled off under reduced pressure to obtain a residue. The residue was recrystallized from ethyl acetate to obtain 5.5 g of a yellowish solid. The solid was dissolved in a mixed solvent of 150 mL of toluene and 30 mL of Solmix A-11, to which 0.1 g of Pd/C was added, followed by stirring for 15 hours in a hydrogen atmosphere at 25° C. After removing Pd/C from the reaction mixture by filtration, the filtrate was washed with a 2N sodium hydroxide aqueous solution, a saturated sodium thiosulfate aqueous solution and water, followed by drying over anhydrous magnesium sulfate. Thereafter, the solvent was distilled off under reduced pressure to obtain a residue. The resulting residue was purified by a preparative column chromatography using a mixed solvent of heptane and ethyl acetate (heptane/ethyl acetate=1/1 by volume) as a developing solvent and silica gel as a mediator, and further purified by recrystallization from a mixed solvent of toluene and ethanol (toluene/ethanol=1/1 by volume) to obtain 1.69 g of 3-chloro-4-ethoxy-2-fluoro-4"-propyl-[1,1';4',1"]terphenyl (C195). The resulting compound (C195) was colorless crystals, and the yield was 11.2% based on the compound (b60).

The transition temperatures of the resulting compound (C195) were as follows.

Transition temperature: C (129.2 $S_A$) 136.8 N 183.2 Iso

The resulting compound exhibited the following chemical shift δ (ppm) of $^1$H-NMR analysis, and thus the compound was identified as 3-chloro-4-ethoxy-2-fluoro-4"-propyl-[1,1';4',1"]terphenyl. The measuring solvent was $CDCl_3$.

Chemical shift δ (ppm): 7.66-7.54 (m, 6H), 7.28-7.25 (m, 3H), 6.80 (dd, 1H), 4.16 (q, 2H), 2.64 (t, 2H), 1.72-1.63 (m, 2H), 1.50 (t, 3H), 0.98 (t, 3H)

Example 11

Synthesis of trans-4'-(3-chloro-4-ethoxy-2-fluorophenoxymetyl)-trans-4-propyl-bicyclohexyl (C232)

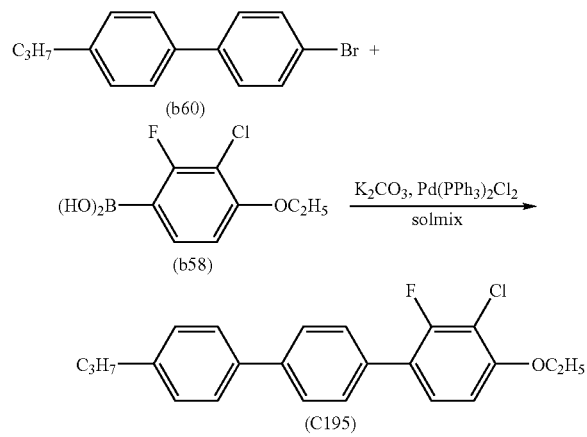

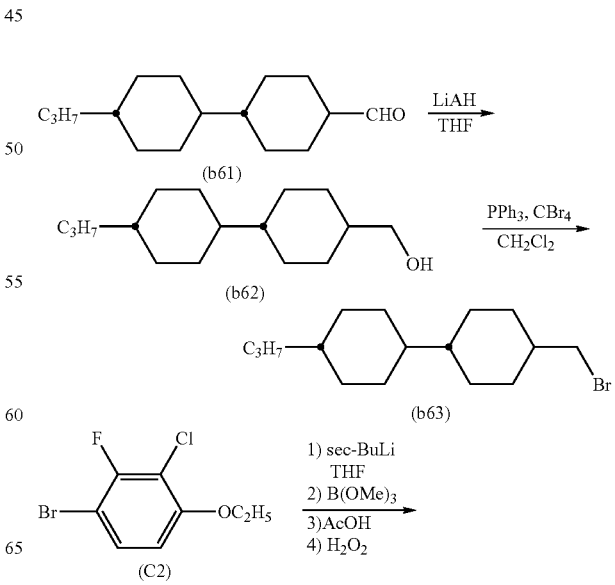

11.6 g of the compound (b58), 11.2 g of 4'-bromo-4-propyl-biphenyl (b60), 11.3 g of potassium carbonate and 0.29 g of $Pd(PPh_3)_2Cl$ were added to a reactor having 110 mL of Solmix A-11 placed therein. The mixture was refluxed under -continued

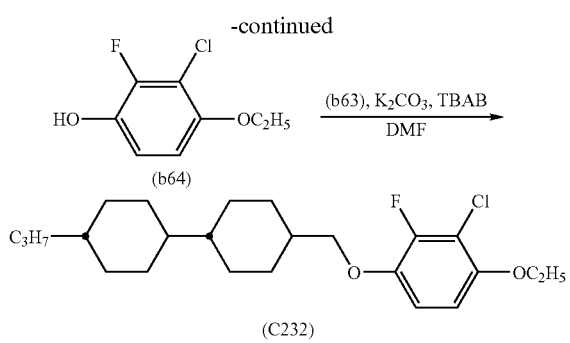

First Step 1.90 g of lithium aluminum hydride was suspended in 100 mL of THF. 60 mL of a THF solution having 20.01 g of trans-4-(trans-4-propylcyclohexyl)cyclohexylaldehyde (b61) dissolved therein was added dropwise to the suspension liquid in a temperature range of 10 to 15° C., followed by stirring for 2 hours in that temperature range. After completing the reaction, ethyl acetate and a saturated aqueous ammonium chloride were sequentially added to the reaction mixture under cooling with ice, and a deposit was removed by filtering with Celite. The filtrate was extracted with ethyl acetate. The resulting organic layer was washed sequentially with water and a saturated sodium chloride aqueous solution, followed by drying over anhydrous magnesium sulfate. The solution was concentrated under reduced pressure to obtain 18.48 g of a crude compound containing trans-4'-hydroxymethyl-trans-4-propyl-bicyclohexyl (b62). The resulting crude compound was a colorless solid.

Second Step 18.48 g of the crude compound containing the compound (b62) and 26.68 g of triphenylphosphine were dissolved in 200 mL of methylene chloride. 42.54 g of carbon tetrabromide was added dropwise to the solution slowly at room temperature, followed by stirring for 5.5 hours at room temperature. A saturated sodium thiosulfate aqueous solution and ethyl acetate were added to the crude compound, followed by mixing, and the mixture was left at rest to separate into an organic layer and an aqueous layer, followed by extracting to the organic layer. The resulting organic layer was washed sequentially with water and a saturated sodium chloride aqueous solution, dried over anhydrous magnesium sulfate, and concentrated under reduced pressure to obtain a residue. The residue was a yellowish solid. 74.77 g of the residue was suspended in 300 mL of heptane, and after removing insoluble matters by filtration, the filtrate was concentrated under reduced pressure to obtain 39.07 g of a residue in yellowish oily form. The residue was purified by a preparative column chromatography using heptane as a developing solvent and silica gel as a mediator to obtain 24.36 g of trans-4'-bromomethyl-trans-4-propyl-bicyclohexyl (b63). The resulting compound (b63) was a colorless solid.

Third Step 30.02 g of the compound (C2) was dissolved in 300 mL of THF. sec-BuLi (1.01 M solution, 124 mL) was added dropwise to the resulting solution in a temperature range of −70 to −75° C., and after completing the dropwise addition, the mixture was stirred for 1 hour in that temperature range. 40 mL of a THF solution having 18.71 g triisopropyl borate dissolved therein was added dropwise to the resulting solution in a temperature range of −70 to −75° C., and after completing the dropwise addition, the mixture was stirred for 1 hour in that temperature range. Thereafter, the temperature of the solution was gradually increased to room temperature, followed by stirring over night. After adding 11.92 g of acetic acid to the reaction mixture, followed by stirring for 30 minutes, 29.95 g of hydrogen peroxide was added dropwise thereto slowly at room temperature, and after completing the dropwise addition, the mixture was stirred for 4.5 hours at room temperature. A sodium nitrite aqueous solution and ethyl acetate were added to the reaction mixture, followed by mixing, and the mixture was left at rest to separate into an organic layer and an aqueous layer, followed by extracting to the organic layer. The resulting organic layer was washed sequentially with water and a saturated sodium chloride aqueous solution, dried over anhydrous magnesium sulfate, and concentrated under reduced pressure to obtain a residue. The residue was a yellowish solid. 30.97 g of the residue was purified by a preparative column chromatography using a mixed solvent of heptane and ethyl acetate (heptane/ethyl acetate=5/1 by volume) as a developing solvent and silica gel as a mediator to obtain 13.29 g of 3-chloro-4-ethoxy-2-fluorophenol (b64). The resulting compound (b64) was a yellowish solid.

Fourth Step 1.51 g of the compound (b64) obtained in the third step was dissolved in 40 mL of N,N,-dimethylformamide. After suspending 1.99 g of potassium carbonate in the solution, 3.08 g of the compound (b63) obtained in the second step and 0.26 g of tetrabutylammonium bromide (TBAB) were added thereto, followed by stirring for 17.5 hours at 80° C. After completing the reaction, water and ethyl acetate were added to the reaction mixture, followed by mixing, and the mixture was left at rest to separate into an organic layer and an aqueous layer, followed by extracting to the organic layer. The resulting organic layer was washed sequentially with water, a 5% sodium thiosulfate aqueous solution, water and a saturated sodium chloride aqueous solution, dried over anhydrous magnesium sulfate, and concentrated under reduced pressure to obtain a residue. The residue was a colorless solid. 3.56 g of the residue was purified by a preparative column chromatography using a mixed solvent of heptane and ethyl acetate (heptane/ethyl acetate=50/1 by volume) as a developing solvent and silica gel as a mediator, and further purified by repeating recrystallization from a mixed solvent of heptane and ethanol (heptane/ethanol=1/1 by volume) to obtain purified trans-4'-(3-chloro-4-ethoxy-2-fluorophenoxymetyl)-trans-4-propyl-bicyclohexyl (C232).

The transition temperatures of the resulting compound (C232) were as follows.

Transition temperature: C 80.1 N 139.9 Iso

The resulting compound exhibited the following chemical shift δ (ppm) of $^1$H-NMR analysis, and thus the compound was identified as trans-4'-(3-chloro-4-ethoxy-2-fluorophenoxymetyl)-trans-4-propyl-bicyclohexyl. The measuring solvent was $CDCl_3$.

Chemical shift δ (ppm): 6.58-6.66 (m, 2H), 4.06 (q, 2H) 3.76 (d, 2H), 1.94-0.85 (m, 30H)

Example 12

Synthesis of 3-chloro-2-fluoro-4-(trans-4-pentyl-cyclohexylmethoxy)-4'-propylbiphenyl (C264)

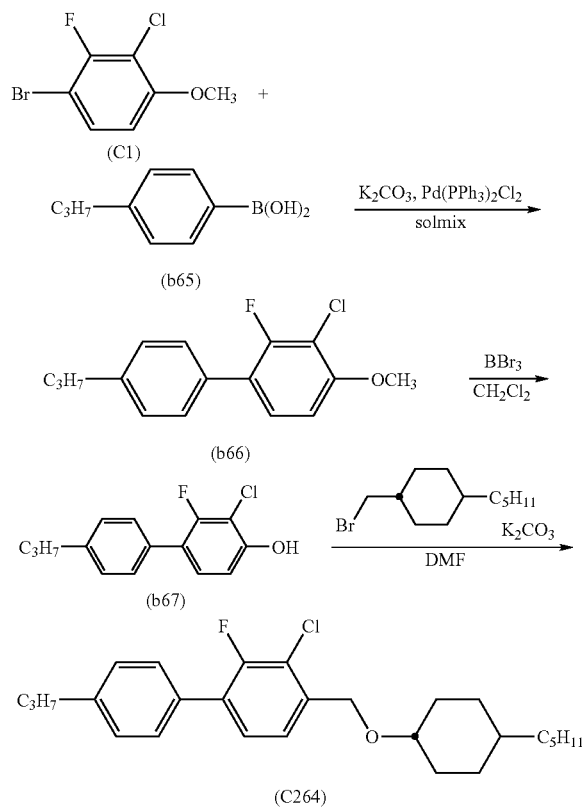

First Step 24.7 g of the compound (b65), 30.0 g of 1-boromo-3-chloro-2-fluoro-4-methoxybenzene (C1), 34.6 g of potassium carbonate and 0.88 g of Pd(PPh$_3$)$_2$Cl were added to a reactor having 120 mL of Solmix A-11 placed therein. The mixture was refluxed under heating and stirring for 2 hours. After cooling the reaction mixture to 30° C., 200 mL of toluene and 300 mL of water were added to the reaction mixture, followed by mixing. Thereafter, the mixture was left at rest to separate into an organic layer and an aqueous layer, followed by extracting to the organic layer. The resulting organic layer was washed sequentially with a 2N sodium hydroxide aqueous solution, a saturated sodium hydrogen carbonate aqueous solution and water. Thereafter, the solvent was distilled off under reduced pressure to obtain a residue. The residue was recrystallized from Solmix A-11 to obtain 28.4 g of a yellowish solid. The solid was dissolved in a mixed solvent of 100 mL of toluene and 30 mL of Solmix A-11, to which 0.5 g of Pd/C was added, followed by stirring for 20 hours in a hydrogen atmosphere at 25° C. After removing Pd/C from the reaction mixture by filtration, the solvent was distilled off under reduced pressure to obtain a residue. The resulting residue was purified by a preparative column chromatography using a heptane as a developing solvent and silica gel as a mediator, and further purified by recrystallization from Solmix A-11 to obtain 24.9 g of 3-chloro-2-fluoro-4-methoxy-4'-propylbiphenyl (b66). The resulting compound (b66) was colorless crystals, and the yield was 71.2% based on the compound (C1).

The transition temperature of the resulting compound (b66) was as follows.

Transition temperature: C 54.1 Iso

Second Step 22.0 g of the compound (b66) was dissolved in 200 mL of methylene chloride. 23.7 g of boron tribromide was added dropwise to the resulting solution in a temperature range of −27 to −20° C., and the temperature of the solution was gradually increased to room temperature, followed by stirring overnight. The resulting reaction mixture was poured slowly to 300 mL of iced water, and the mixture was left at rest to separate into an organic layer and an aqueous layer, followed by extracting to the organic layer. The resulting organic layer was washed with a sodium chloride aqueous solution in three times, dried over anhydrous magnesium sulfate, and concentrated under reduced pressure to obtain a residue. The residue was a yellowish solid. 19.7 g of the residue was purified by recrystallization from a mixed solvent of heptane and toluene (heptane/toluene=2/1 by volume) to obtain 18.0 g of 3-chloro-2-fluoro-4'-propylbiphenyl-4-ol (b67). The resulting compound (b67) was a white solid.

Third Step 4.0 g of the compound (b67) obtained in the second step was dissolved in 20 mL of N,N,-dimethylformamide. After suspending 2.5 g of potassium carbonate in the solution, 5.6 g of the compound (b68) was added thereto, followed by stirring for 6 hours at 70° C. After completing the reaction, water and toluene were added to the reaction mixture, followed by mixing. Thereafter, the mixture was left at rest to separate into an organic layer and an aqueous layer, followed by extracting to the organic layer. The resulting organic layer was washed sequentially with water, a 2N sodium hydroxide aqueous solution, a saturated sodium chloride aqueous solution and water, and then concentrated under reduced pressure to obtain a residue. 7.7 g of the residue was purified by a preparative column chromatography using a mixed solvent of heptane and toluene (heptane/toluene=3/1 by volume) as a developing solvent and silica gel as a mediator, and further purified by repeating recrystallization from a mixed solvent of heptane and Solmix A-11 (heptane/Solmix A-11=2/1 by volume) to obtain 3-chloro-2-fluoro-4-(trans-4-pentyl-cyclohexylmethoxy)-4'-propylbiphenyl (C264) as colorless crystals. The yield was 89.5% based on the compound (b67).

The transition temperatures of the resulting compound (C264) were as follows.

Transition temperature: C 79.9 N 110.6 Iso

The resulting compound exhibited the following chemical shift δ (ppm) of $^1$H-NMR analysis, and thus the compound was identified as 3-chloro-2-fluoro-4-(trans-4-pentyl-cyclohexylmethoxy)-4'-propylbiphenyl (C264). The measuring solvent was CDCl$_3$.

Chemical shift δ (ppm): 7.41-7.39 (m, 2H), 7.25-7.22 (m, 3H), 6.77-6.75 (dd, 1H), 3.85 (d, 2H), 2.63 (t, 2H), 1.94 (m, 2H), 1.85-1.81 (m, 3H), 1.68 (m, 2H), 1.31-1.06 (m, 11H), 1.10-0.85 (m, 8H)

Example 13

Synthesis of 3'-chloro-4"-ethyl-2'-fluoro-4-propyl-[1,1';4',1"]terphenyl (C293)

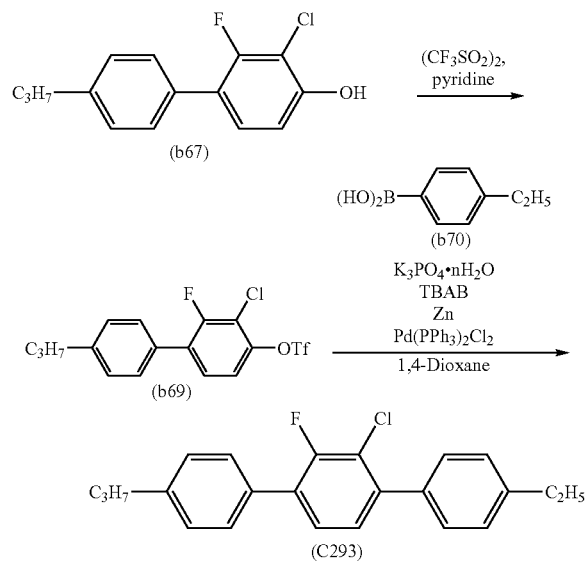

First Step 13.0 g of the compound (b67) was added to a reactor having 50 mL pyridine placed therein in a nitrogen atmosphere, and after dissolving, the solution was cooled to 5° C. 16.6 g of trifluoromethanesulfonic anhydride was added dropwise to the solution over 1 hour in a temperature range of 5 to 10° C., followed by stirring for 3 hour at 20° C. The resulting reaction mixture was poured slowly into a cooled mixed solution of 100 mL of 1N hydrochloric acid and 100 mL of heptane. Thereafter, the mixture was left at rest to separate into an organic layer and an aqueous layer, followed by extracting to the organic layer. The resulting organic layer was washed sequentially with water, a saturated sodium hydrogen carbonate aqueous solution and water. The resulting organic layer was purified by a preparative column chromatography using heptane as a developing solvent and silica gel as a mediator, and then the solvent was distilled off under reduced pressure to obtain 19.1 g of a colorless transparent compound (b69). The yield was 97.9% based on the compound (b67).

Second Step 6.0 g of the compound (b69) 2.7 g of the compound (b70), 9.6 g of tripotassium phosphate, 2.44 g of TBAB, 0.49 g of zinc powder and 0.11 g of $Pd(PPh_3)_2Cl$ were added to a reactor having 60 mL of 1,4-dioxane in a nitrogen atmosphere. They were stirred for 4 hours under refluxing by heating. 2.0 g of tripotassium phosphate was further added thereto, and the mixture was stirred for 2 hours under refluxing by heating. After cooling the resulting reaction mixture to 30° C., the resulting reaction mixture was poured slowly into a mixed solution of 100 mL of toluene and 200 mL of 1N hydrochloric acid. Thereafter, the mixture was left at rest to separate into an organic layer and an aqueous layer, followed by extracting to the organic layer. The resulting organic layer was washed sequentially with 1N hydrochloric acid, a 2N sodium hydroxide aqueous solution, a saturated sodium hydrogen carbonate aqueous solution and water. Thereafter, the solvent was distilled off to obtain 5.3 g of residue. The residue was purified by a preparative column chromatography using a mixed solvent of heptane and toluene (heptane/toluene=4/1 by volume) as a developing solvent and silica gel as a mediator, and further purified by repeating recrystallization from a mixed solvent of heptane and ethanol (heptane/ethanol=2/1 by volume) to obtain 3.9 g of 3'-chloro-4"-ethyl-2'-fluoro-4-propyl-[1,1';4',1"]terphenyl (C293) as colorless crystals. The yield was 72.3% based on the compound (b69).

The transition temperature of the resulting compound (C293) was as follows.

Transition temperature: C 83.4 Iso

The resulting compound exhibited the following chemical shift δ (ppm) of $^1$H-NMR analysis, and thus the compound was identified as 3'-chloro-4"-ethyl-2'-fluoro-4-propyl-[1,1';4',1"]terphenyl (C293). The measuring solvent was $CDCl_3$.

Chemical shift δ (ppm): 7.50-7.49 m, 2H), 7.42-7.40 (m, 2H), 7.36 (t, 1H), 7.29 (t, 4H), 7.19 (dd, 1H), 2.73 (q, 2H), 2.65 (t, 2H), 1.70 (m, 2H), 1.30 (t, 3H), 0.99 (t, 3H)

Example 14

The following compounds (C21) to (C27), (C29) to (C43), (C45) to (C57), (C59) to (C95), (C97) to (C114), (C116) to (C153), (C155) to (C194), (C196) to (C231), (C233) to (C263), (C265) to (C292), and (C294) to (C300) were synthesized in the similar manner as the synthesis methods described in Examples 4 to 13. The compounds (C28), (C44), (C58), (C96), (C115), (C154), (C195), (C232), (C264) and (C293) are also described in the following. The values shown with the compounds are values measured in the aforementioned methods, in which the maximum temperature ($T_{NI}$), the dielectric anisotropy (Δ∈) and the optical anisotropy (Δn) are extrapolated values obtained by converting measured values of samples obtained by mixing the compound with the base mixture A, by means of the aforementioned extrapolation method.

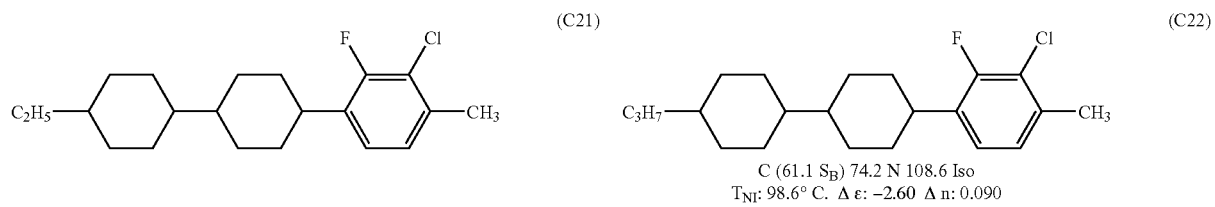

C (61.1 $S_B$) 74.2 N 108.6 Iso
$T_{NI}$: 98.6° C.  Δ ε: −2.60  Δ n: 0.090

-continued

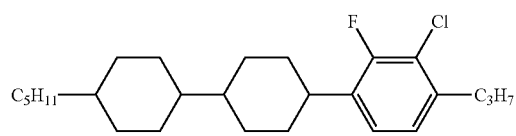
(C23)

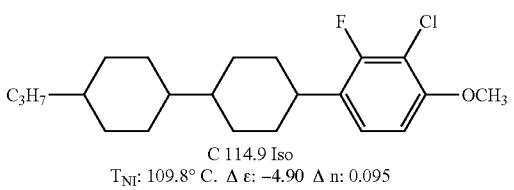
(C24)
C 114.9 Iso
$T_{NI}$: 109.8° C. $\Delta \epsilon$: −4.90 $\Delta n$: 0.095

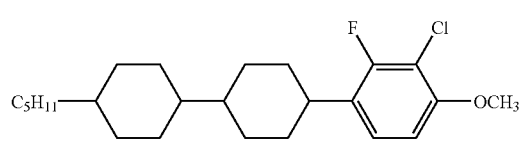
(C25)

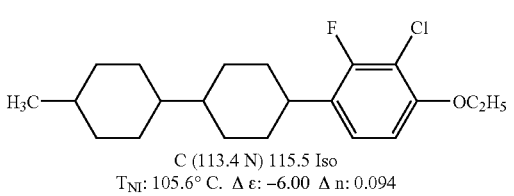
(C26)
C (113.4 N) 115.5 Iso
$T_{NI}$: 105.6° C. $\Delta \epsilon$: −6.00 $\Delta n$: 0.094

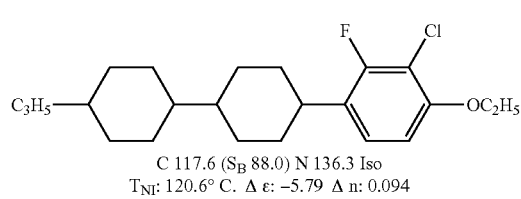
(C27)
C 117.6 ($S_B$ 88.0) N 136.3 Iso
$T_{NI}$: 120.6° C. $\Delta \epsilon$: −5.79 $\Delta n$: 0.094

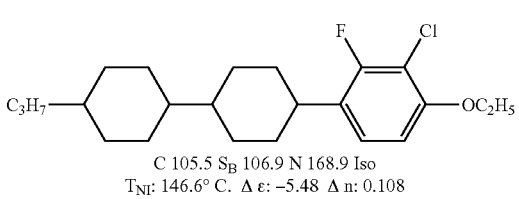
(C28)
C 105.5 $S_B$ 106.9 N 168.9 Iso
$T_{NI}$: 146.6° C. $\Delta \epsilon$: −5.48 $\Delta n$: 0.108

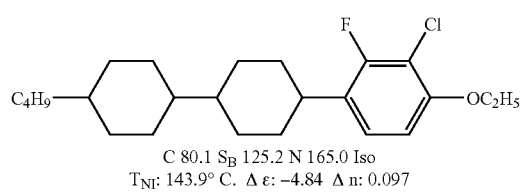
(C29)
C 80.1 $S_B$ 125.2 N 165.0 Iso
$T_{NI}$: 143.9° C. $\Delta \epsilon$: −4.84 $\Delta n$: 0.097

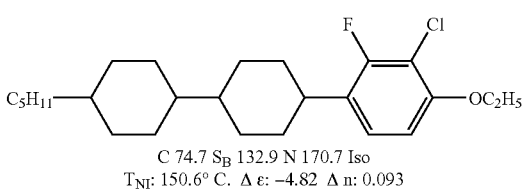
(C30)
C 74.7 $S_B$ 132.9 N 170.7 Iso
$T_{NI}$: 150.6° C. $\Delta \epsilon$: −4.82 $\Delta n$: 0.093

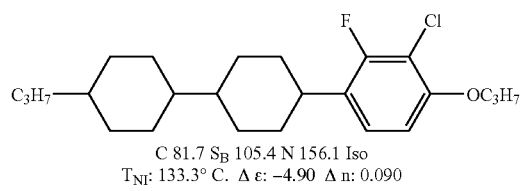
(C31)
C 81.7 $S_B$ 105.4 N 156.1 Iso
$T_{NI}$: 133.3° C. $\Delta \epsilon$: −4.90 $\Delta n$: 0.090

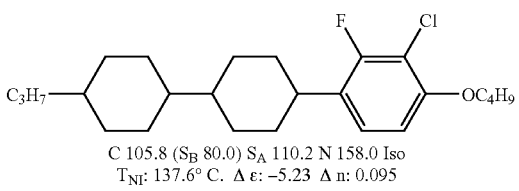
(C32)
C 105.8 ($S_B$ 80.0) $S_A$ 110.2 N 158.0 Iso
$T_{NI}$: 137.6° C. $\Delta \epsilon$: −5.23 $\Delta n$: 0.095

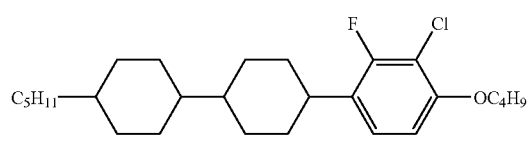
(C33)

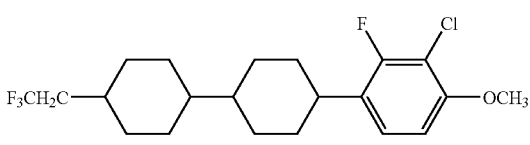
(C34)

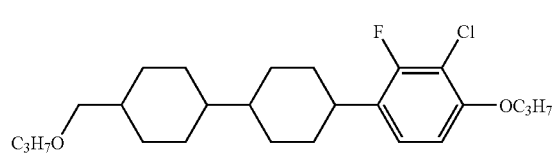
(C35)

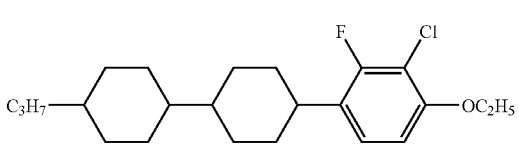
(C36)

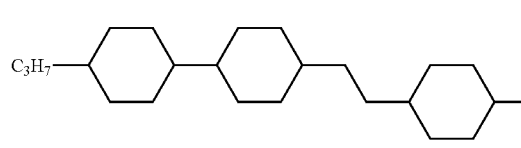
(C37)

(C38)

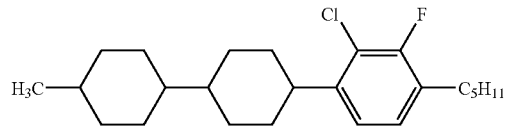
(C38)

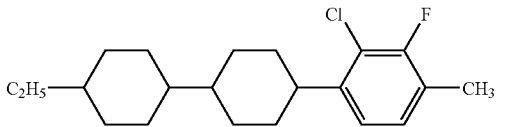
(C39)

-continued
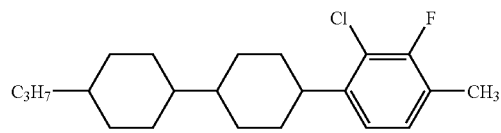 (C40)
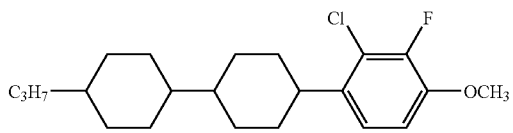 (C41)
C₁ 74.2 C₂ 100.7 N 142.1 Iso
$T_{NI}$: 117.0° C.  Δε: −5.15  Δn: 0.087
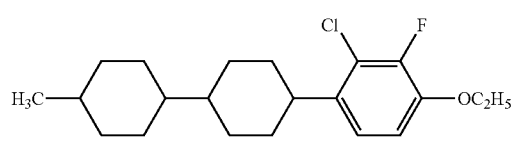 (C42)
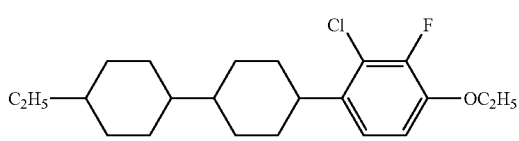 (C43)
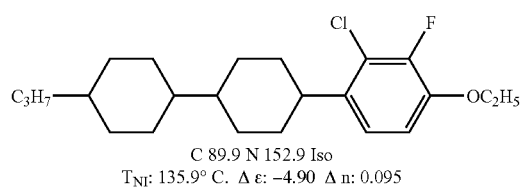 (C44)
C 89.9 N 152.9 Iso
$T_{NI}$: 135.9° C.  Δε: −4.90  Δn: 0.095
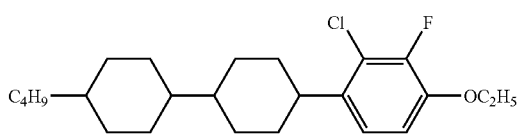 (C45)
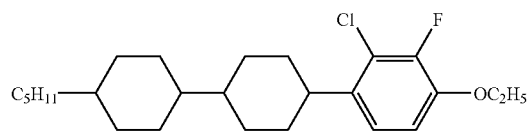 (C46)
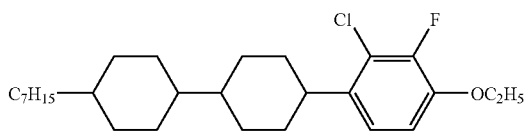 (C47)
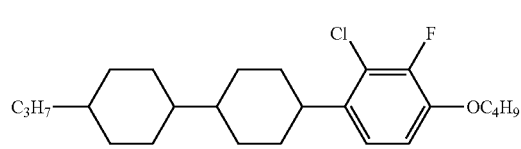 (C48)
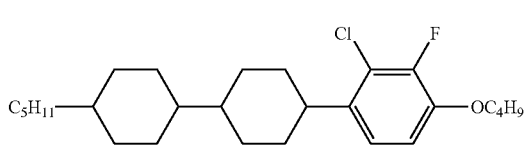 (C49)
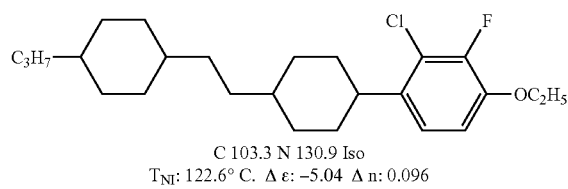 (C50)
C 103.3 N 130.9 Iso
$T_{NI}$: 122.6° C.  Δε: −5.04  Δn: 0.096
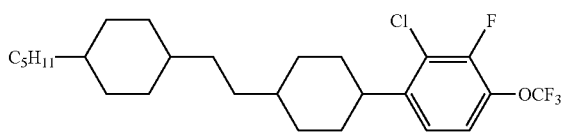 (C51)
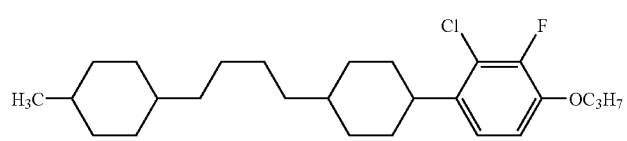 (C52)
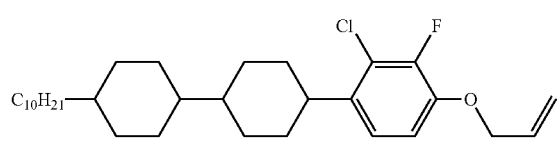 (C53)
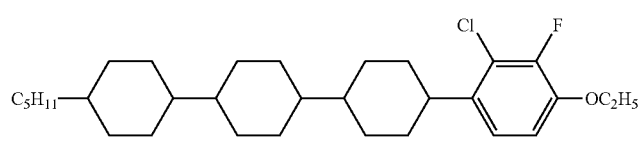 (C54)

(C55)
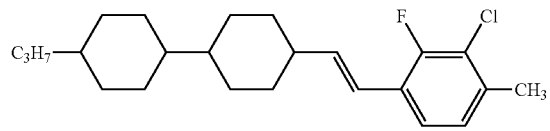
(C56)
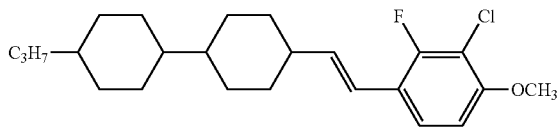
C$_1$ 72.4 C$_2$ 98.9 N 217.4 Iso
T$_{NI}$: 180.6° C.  Δ ε: −5.17  Δ n: 0.150
(C57)
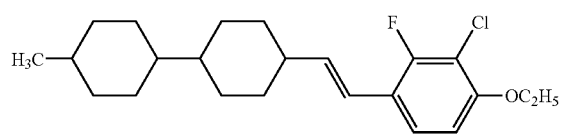
(C58)
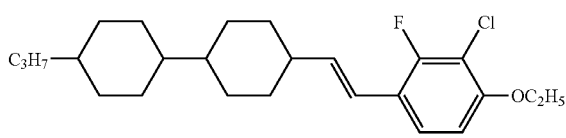
C$_1$ 83.6 C$_2$ 88.9 S$_A$ 125.6 N 224.8 Iso
T$_{NI}$: 197.3° C.  Δ ε: −5.64  Δ n: 0.150
(C59)
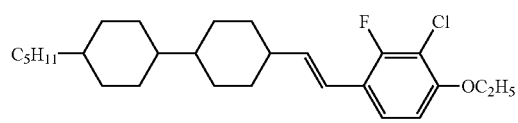
C 83.6 S$_B$ 106.3 S$_A$ 156.5 N 220.9 Iso
T$_{NI}$: 199.9° C.  Δ ε: −5.09  Δ n: 0.148
(C60)
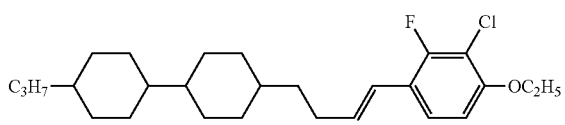
(C61)
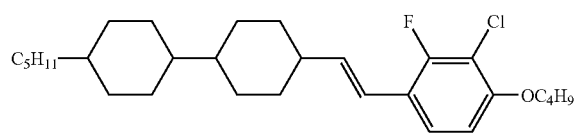
(C62)
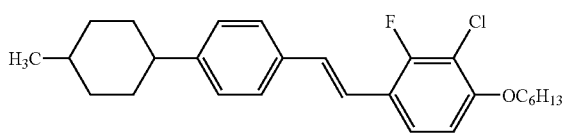
(C63)
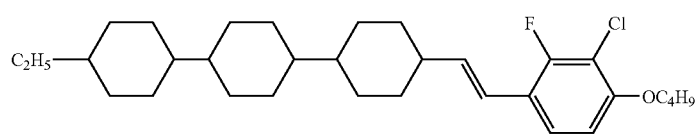
(C64)
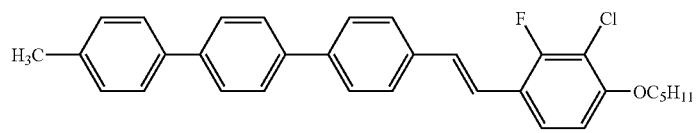
(C65)
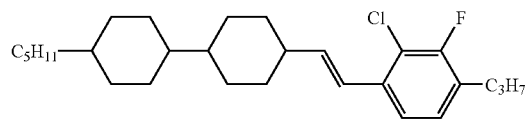
(C66)
(C67)
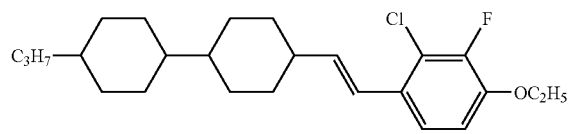
C$_1$ 82.4 C$_2$ 84.8 N 216.3 Iso
T$_{NI}$: 181.9° C.  Δ ε: −5.08  Δ n: 0.142
(C68)
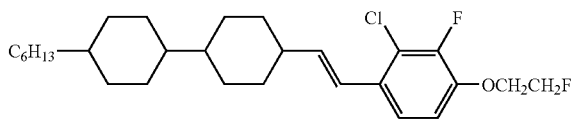
C 58.4 N 206.2 Iso
T$_{NI}$: 177.3° C.  Δ ε: −4.81  Δ n: 0.106
(C69)
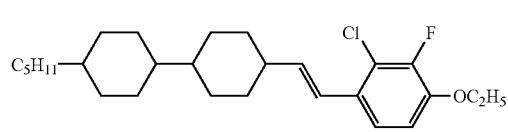
C$_1$ 44.4 C$_2$ 68.4 N 214.32 Iso
T$_{NI}$: 187.3° C.  Δ ε: −4.81  Δ n: 0.138
(C70)
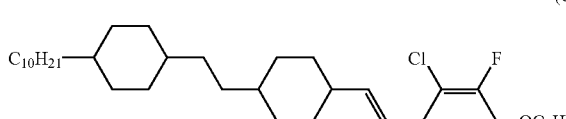

-continued
(C71)
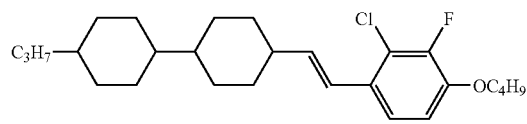
(C72)
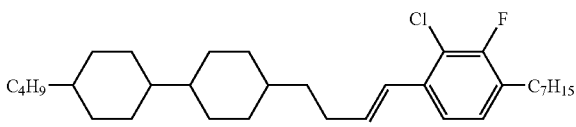
(C73)
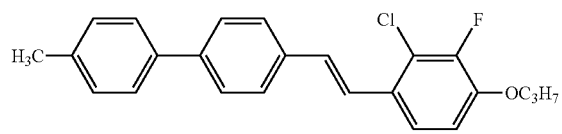
(C74)
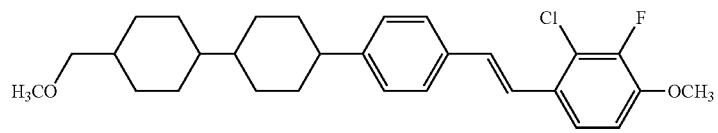
(C75)
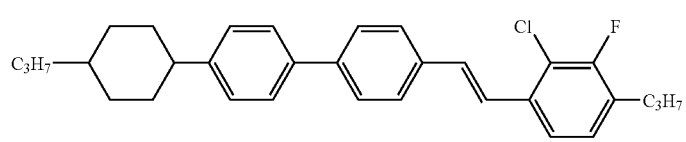
(C76)
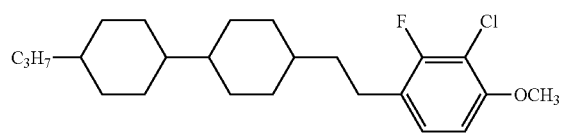
C 92.8 S$_B$ 113.2 N 142.7 Iso
T$_{NI}$: 124.6° C.  Δ ε: −4.51  Δ n: 0.089
(C77)
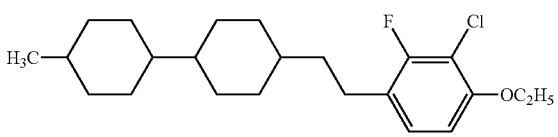
(C78)
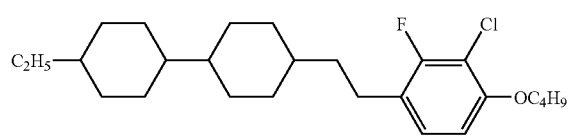
(C79)
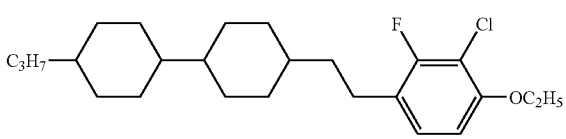
C 62.7 S$_B$110.6 N 150.4 Iso
T$_{NI}$: 140.6° C.  Δ ε: −4.56  Δ n: 0.096
(C80)
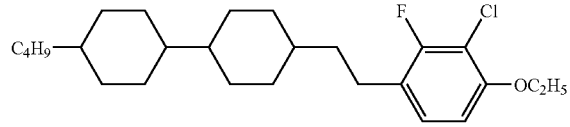
(C81)
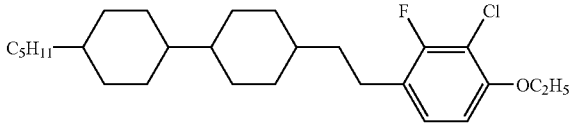
C 52.0 S$_B$134.9 N 151.8 Iso
T$_{NI}$: 145.9° C.  Δ ε: −4.48  Δ n: 0.082
(C82)
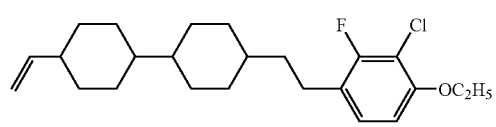
(C83)
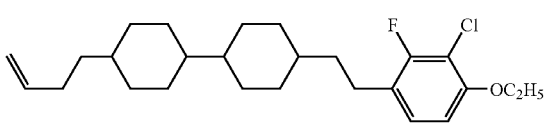
(C84)
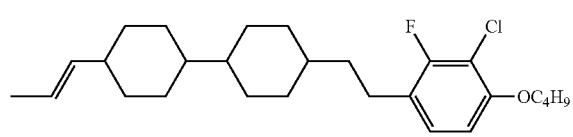
(C85)
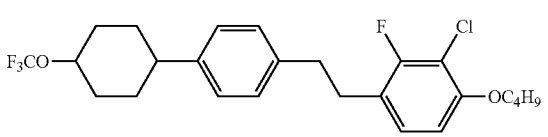

-continued
(C86)
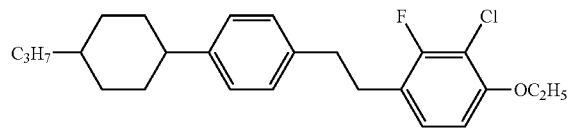
(C87)
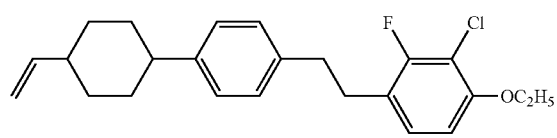
(C88)
(C89)
(C90)
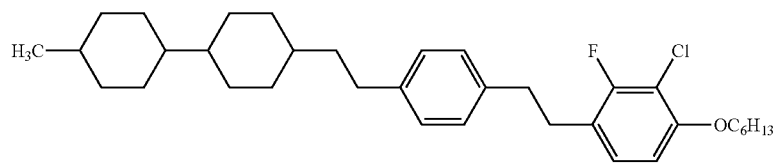
(C91)
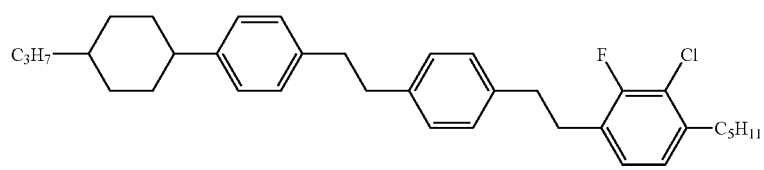
(C92)
(C93)
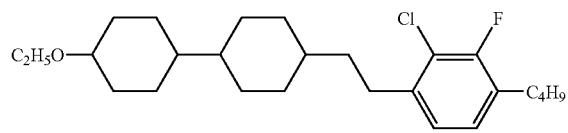
(C94)
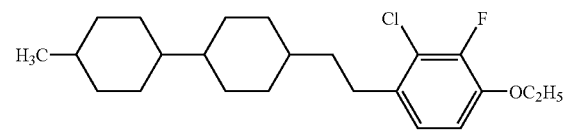
(C95)
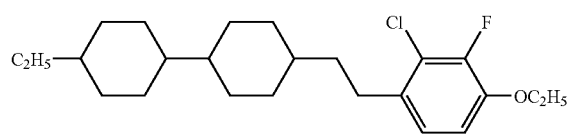
(C96)
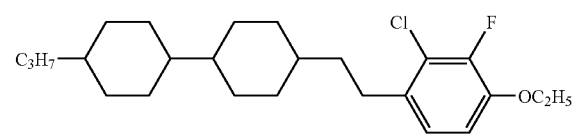
C 63.5 N 153.1 Iso
$T_{NI}$: 144.6° C. Δε: −4.62 Δn: 0.102
(C97)
(C98)
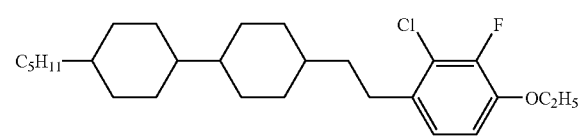
C 69.4 $S_A$ 76.8 N 150.8 Iso
$T_{NI}$: 139.9° C. Δε: −4.30 Δn: 0.095
C 63.0 $S_B$ 92.0 N 154.8 Iso
$T_{NI}$: 148.6° C. Δε: −4.54 Δn: 0.097
(C99)
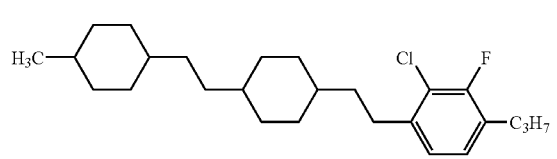
(C100)
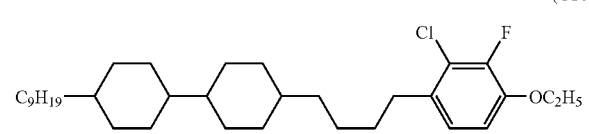

-continued
(C101)
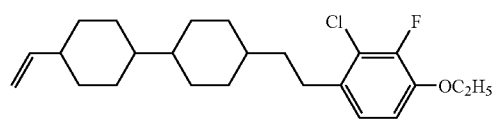
(C102)
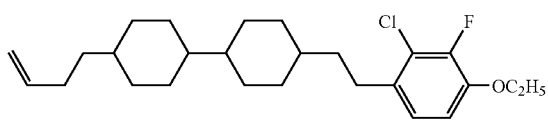
(C103)
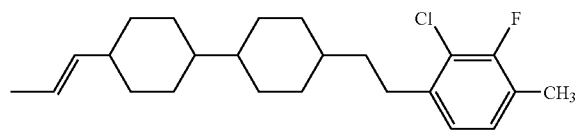
(C104)
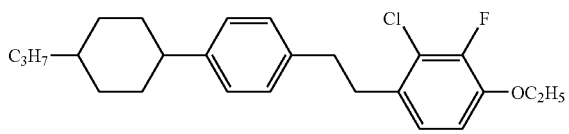
(C105)
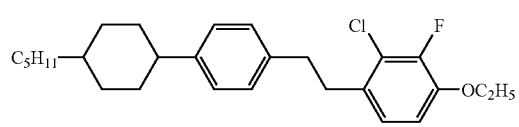
(C106)
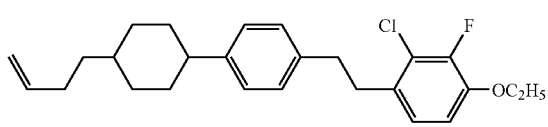
(C107)
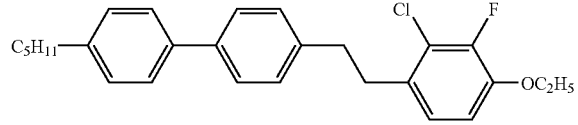
(C108)
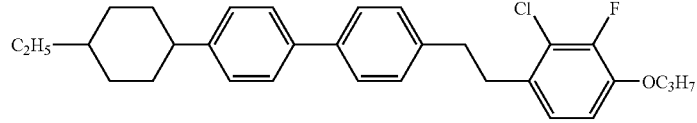
(C109)
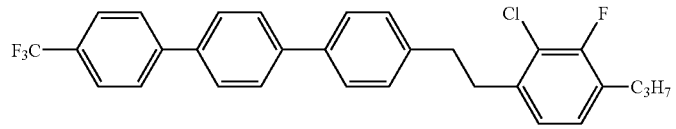
(C110)
(C111)
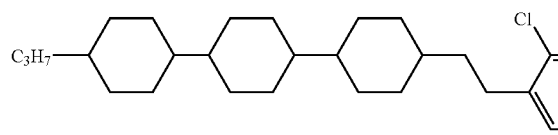
(C112)
(C113)
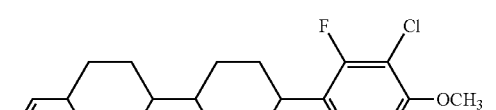
(C114)
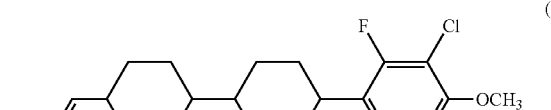
(C115)
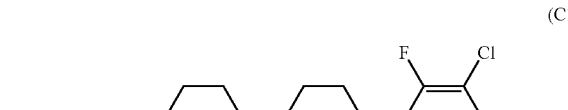
(C116)
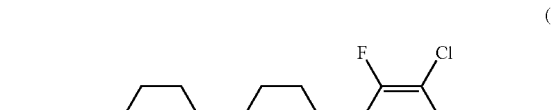
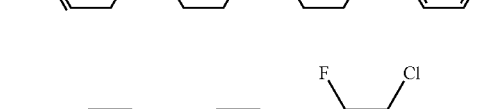
C 113.4 N 151.9 Iso
$T_{NI}$: 131.3° C.  $\Delta \varepsilon$: −6.09  $\Delta$ n: 0.106
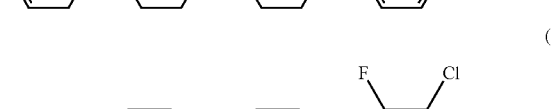
C 118.1 N 199.8 Iso
$T_{NI}$: 161.3° C.  $\Delta \varepsilon$: −5.82  $\Delta$ n: 0.121

-continued
(C117)
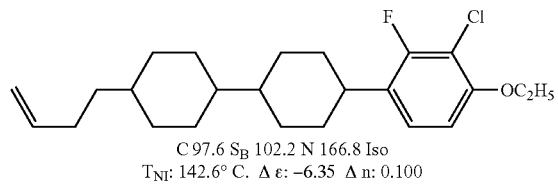
C 97.6 S$_B$ 102.2 N 166.8 Iso
T$_{NI}$: 142.6° C.  Δ ε: −6.35  Δ n: 0.100
(C118)
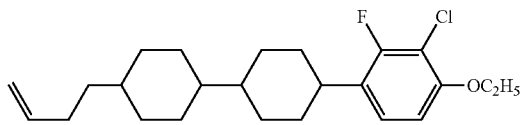
(C119)
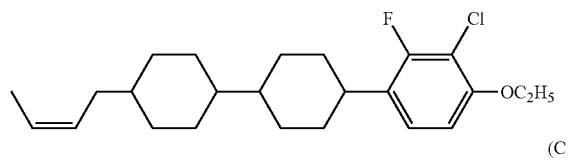
(C120)
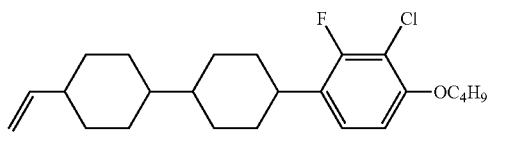
(C121)
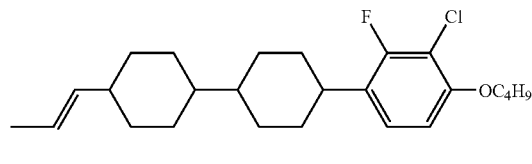
(C122)
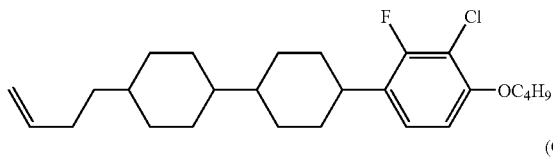
(C123)
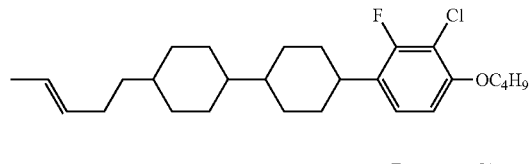
(C124)
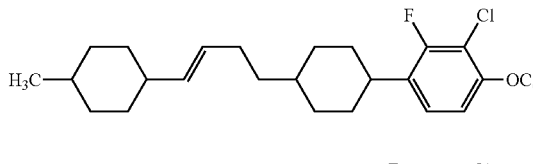
(C125)
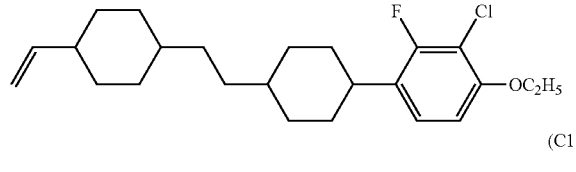
(C126)
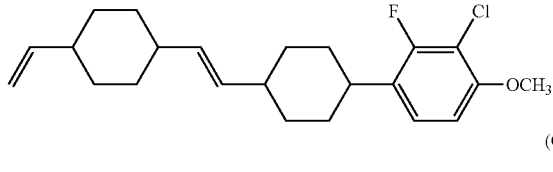
(C127)
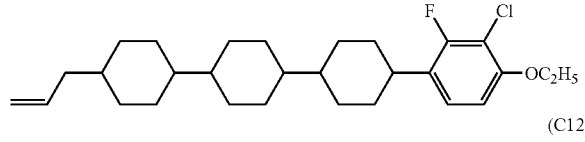
(C128)
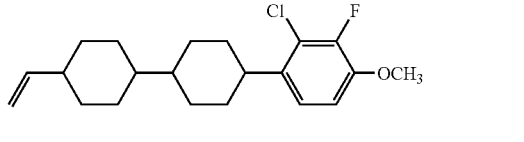
(C129)
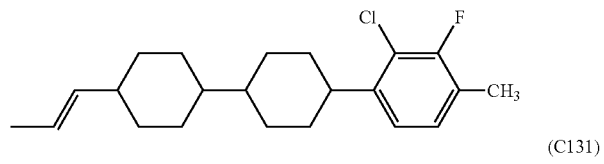
(C130)
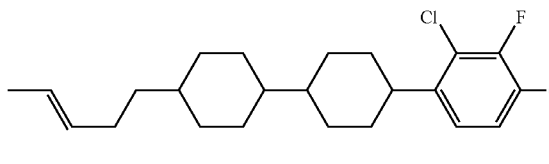
(C131)
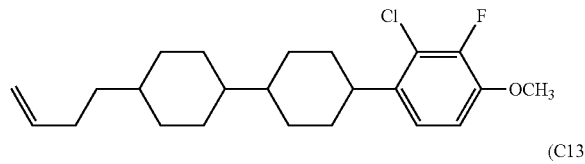
(132)
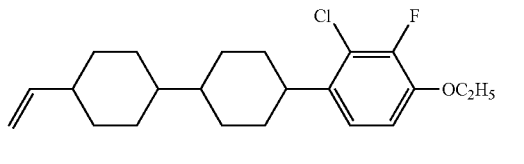
(C133)
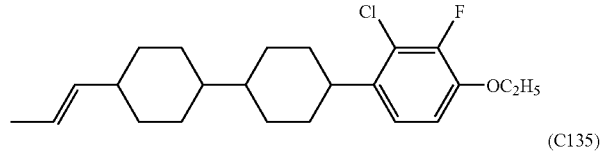
(C134)
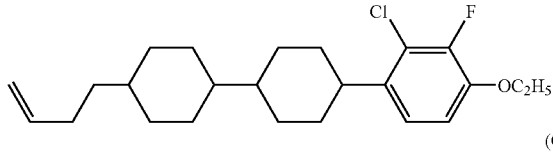
(C135)
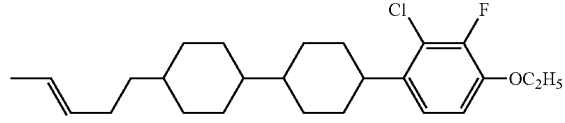
(C136)
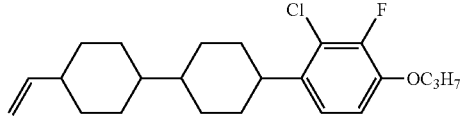

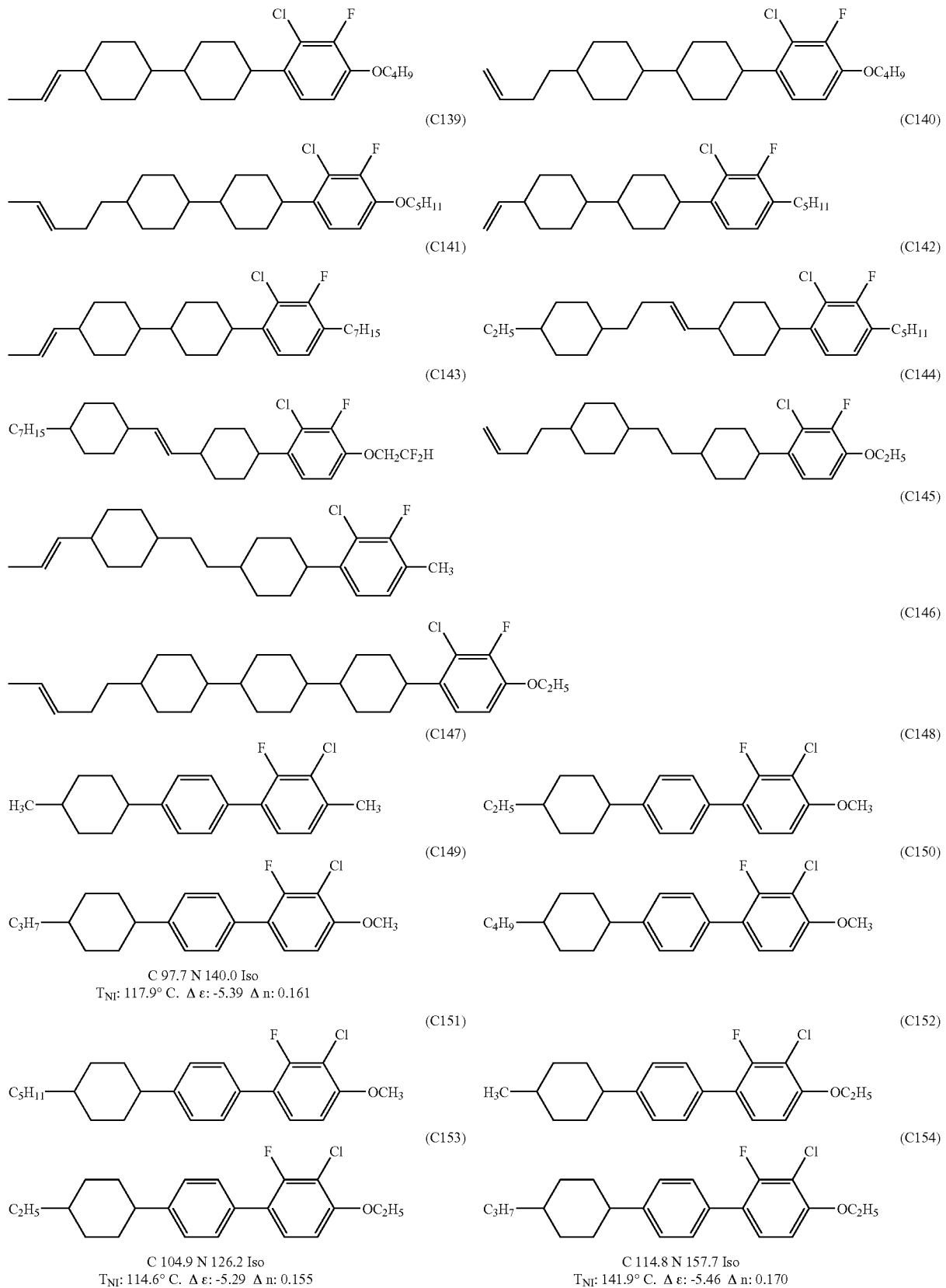

-continued
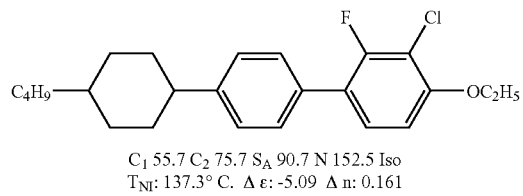
(C155)
C₁ 55.7 C₂ 75.7 S_A 90.7 N 152.5 Iso
T_NI: 137.3° C.  Δ ε: -5.09  Δ n: 0.161
(C156)
C₁ 54.6 C₂ 81.3 (S_B 66.3) S_A 99.3 N 156.3 Iso
T_NI: 145.9° C.  Δ ε: -4.95  Δ n: 0.162
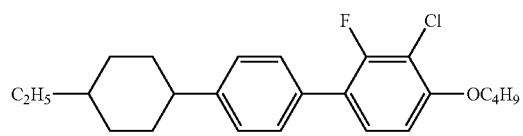
(C157)
(C158)
C 66.5 N 144.6 Iso
T_NI: 132.6° C.  Δ ε: -5.12  Δ n: 0.152
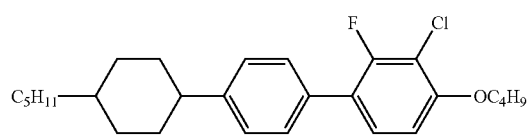
(C159)
(C160)
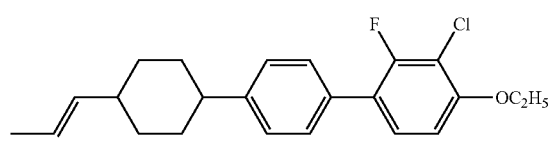
(C161)
(C162)
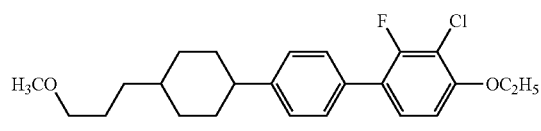
(C163)
(C164)
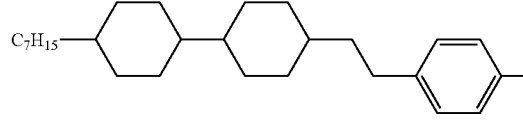
(C165)
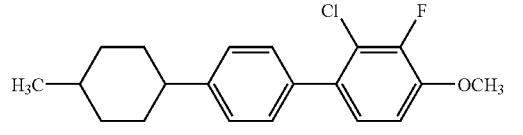
(C166)
(C167)
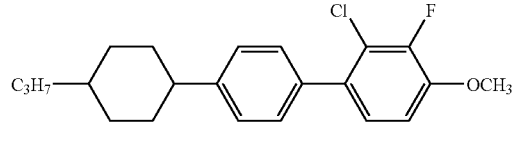
(C168)
(C169)
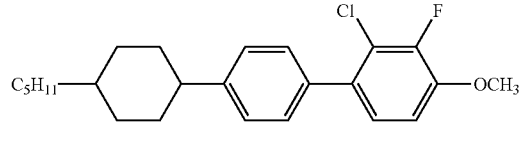
(C170)
(C171)
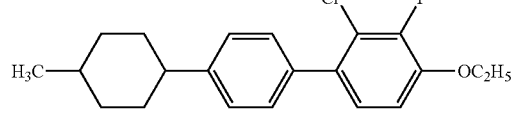
(C172)
(C173)
C 75.8 N 115.3 Iso
T_NI: 110.6° C.  Δ ε: -5.42  Δ n: 0.150

-continued
(C174)
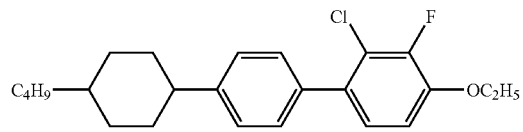
(C175)
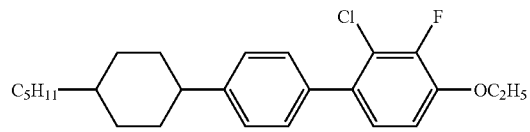
C₁ 39.2 C₂ 69.6 N 124.4 Iso
T_{NI}: 116.6° C. Δε: -4.40 Δn: 0.138
(C176)
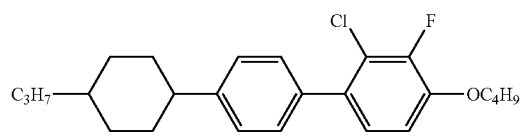
(C177)
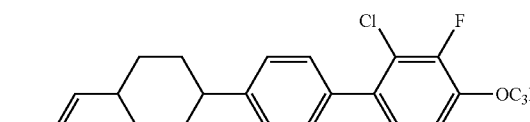
(C178)
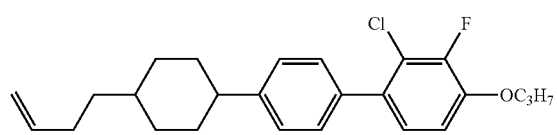
(C179)
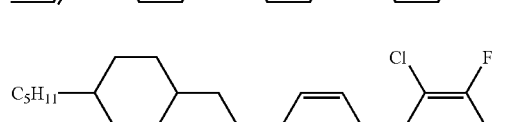
(C180)
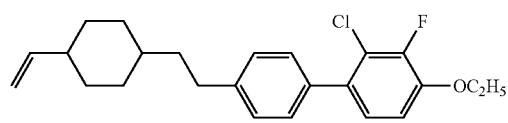
(C181)
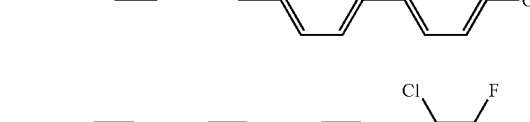
(C182)
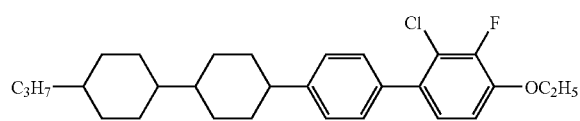
(C183)
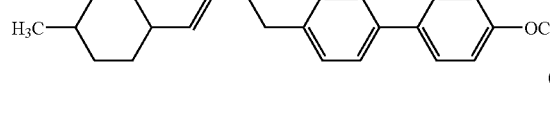
(C184)
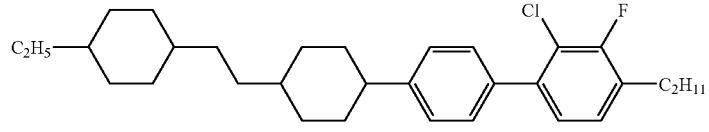
(C185)
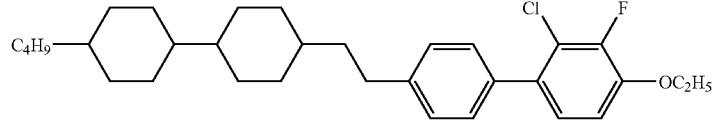
(C186)
(C187)
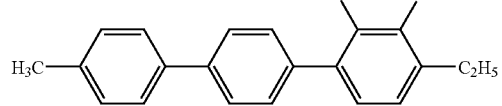
(C188)
(C189)
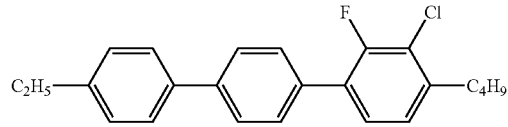
(C190)
(C191)
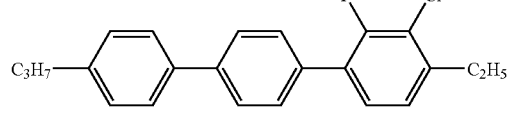
(C192)
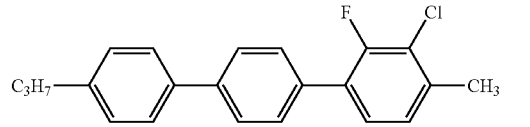
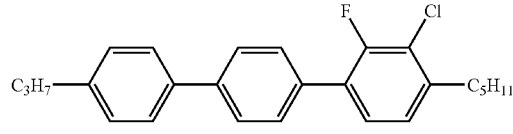
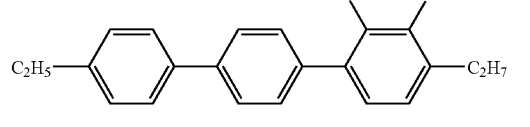
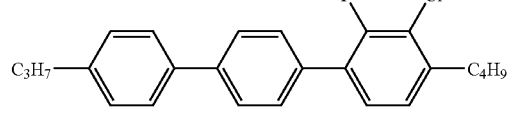
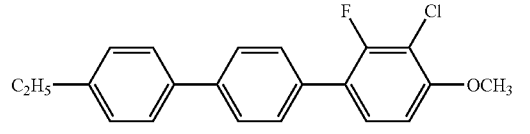

-continued (C193) Structure: C₅H₁₁–[phenyl]–[phenyl]–[2-F,3-Cl,4-OCH₃ phenyl]

(C194) Structure: C₂H₅–[phenyl]–[phenyl]–[2-F,3-Cl,4-OC₂H₅ phenyl]

(C195) Structure: C₃H₇–[phenyl]–[phenyl]–[2-F,3-Cl,4-OC₂H₅ phenyl]
C (129.2 S_A) 136.8 N 183.2 Iso
T_NI: 156.6° C.  Δε: −6.79  Δn: 0.283

(C196) Structure: C₅H₁₁–[phenyl]–[phenyl]–[2-F,3-Cl,4-OC₂H₅ phenyl]

(C197) Structure: C₃H₇–[phenyl]–[phenyl]–[2-F,3-Cl,4-OC₃H₇ phenyl]

(C198) Structure: C₅H₁₁–[phenyl]–[phenyl]–[2-F,3-Cl,4-OC₃H₇ phenyl]

(C199) Structure: C₂H₅–[phenyl]–[phenyl]–[2-F,3-Cl,4-OC₄H₉ phenyl]

(C200) Structure: C₃H₇–[phenyl]–[phenyl]–[2-F,3-Cl,4-OC₄H₉ phenyl]

(C201) Structure: C₅H₁₁–[phenyl]–[phenyl]–[2-F,3-Cl,4-OC₄H₉ phenyl]

(C202) Structure: CH₂=CH-CH₂-CH₂–[phenyl]–[phenyl]–[2-F,3-Cl,4-OC₂H₅ phenyl]

(C203) Structure: CH₂=CH-CH₂-CH₂–[phenyl]–[phenyl]–[2-F,3-Cl,4-OC₄H₉ phenyl]

(C204) Structure: C₅H₁₁–[cyclohexyl]–[phenyl]–[phenyl]–[2-F,3-Cl,4-CH₃ phenyl]

(C205) Structure: C₃H₇–[cyclohexyl]–[phenyl]–[phenyl]–[2-F,3-Cl,4-OC₄H₉ phenyl]

(C206) Structure: C₇H₁₅–[phenyl]–[phenyl]–CH₂CH₂–[phenyl]–[2-F,3-Cl,4-C₃H₇ phenyl]

(C207) Structure: C₃H₇–[phenyl]–[phenyl]–[2-Cl,3-F,4-CH₃ phenyl]

(C208) Structure: C₂H₅–[phenyl]–[phenyl]–[2-Cl,3-F,4-C₃H₇ phenyl]

(C209) Structure: C₂H₅–[phenyl]–[phenyl]–[2-Cl,3-F,4-C₅H₁₁ phenyl]

(C210) Structure: C₃H₇–[phenyl]–[phenyl]–[2-Cl,3-F,4-C₂H₅ phenyl]

(C211) Structure: C₃H₇–[phenyl]–[phenyl]–[2-Cl,3-F,4-C₄H₉ phenyl]

(C212) Structure: C₃H₇–[phenyl]–[phenyl]–[2-Cl,3-F,4-C₅H₁₁ phenyl]

(C213) Structure: C₃H₇–[phenyl]–[phenyl]–[2-Cl,3-F,4-C₇H₁₃ phenyl]

(C214) Structure: C₃H₇–[phenyl]–[phenyl]–[2-Cl,3-F,4-OCH₃ phenyl]

-continued
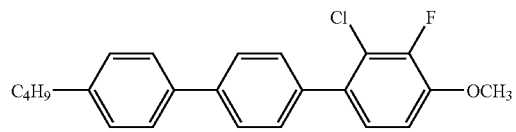
(C215)
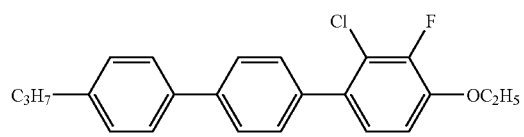
(C216)
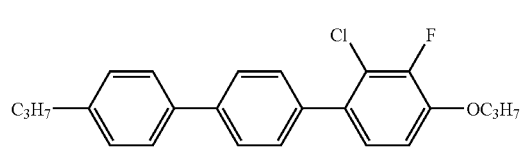
(C217)
C 116.4 N 137.5 Iso
T$_{NI}$: 118.6° C.  Δε: −3.23  Δn: 0.211
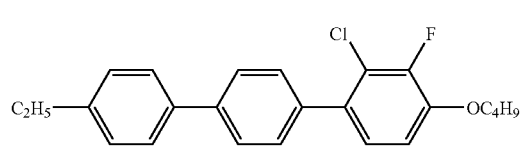
(C218)
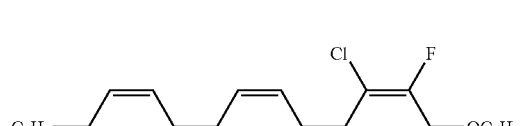
(C219)
(C220)
(C221)
(C222)
(C223)
(C224)
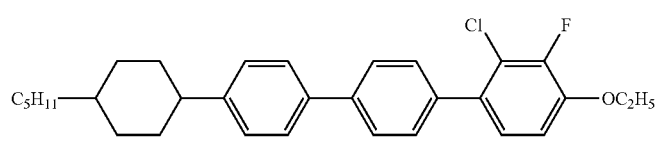
(C225)
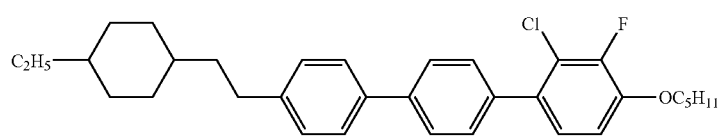
(C226)
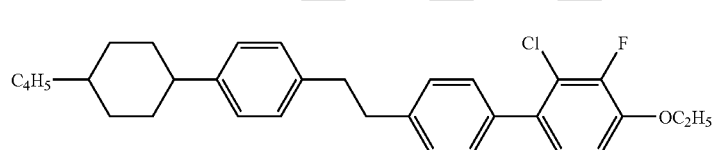
(C227)
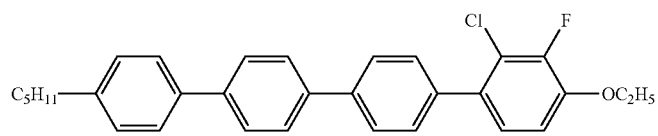
(C228)
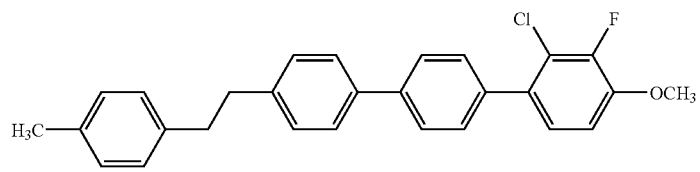
(C229)

-continued
(C230)
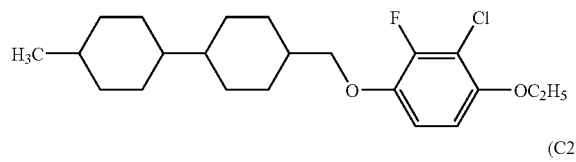
(C231)
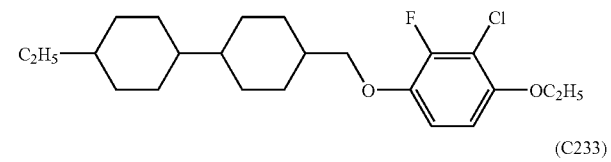
(C232)
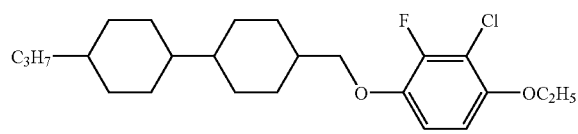
C 80.1 N 139.9 Iso
$T_{NI}$: 131.3° C.  $\Delta \epsilon$: -7.16  $\Delta n$: 0.092
(C233)
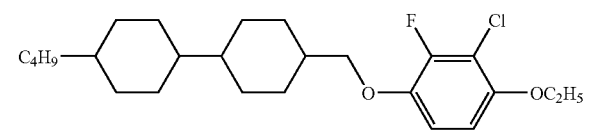
(C234)
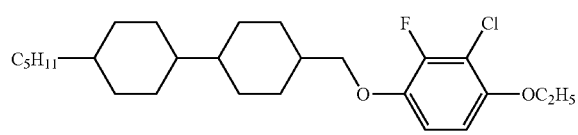
C 73.1 $S_A$ 82.8 N 142.7 Iso
$T_{NI}$: 133.9° C.  $\Delta \epsilon$: -6.14  $\Delta n$: 0.087
(C235)
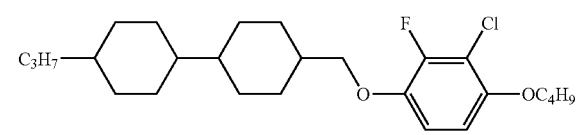
(C236)
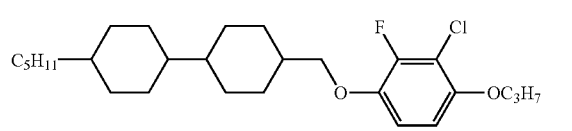
(C237)
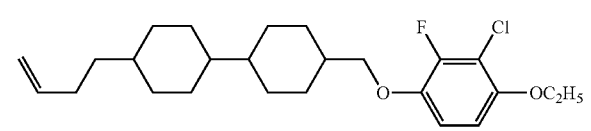
(C238)
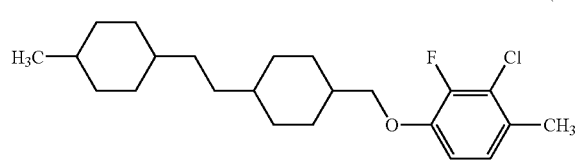
(C239)
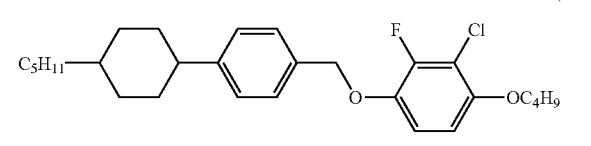
(C240)
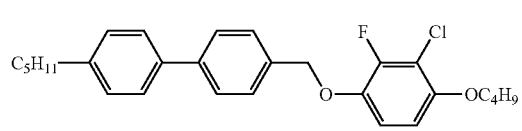
(C241)
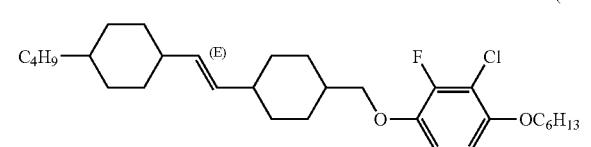
(C242)
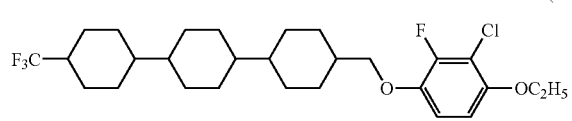
(C243)
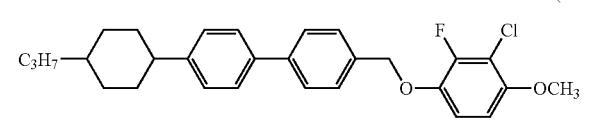
(C244)
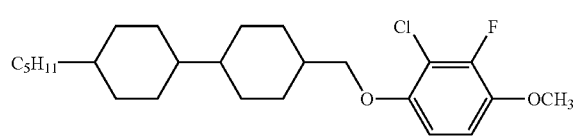
(C245)
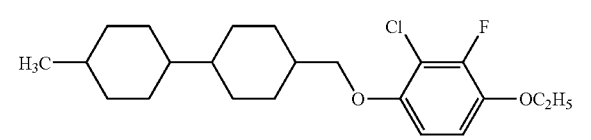
(C246)
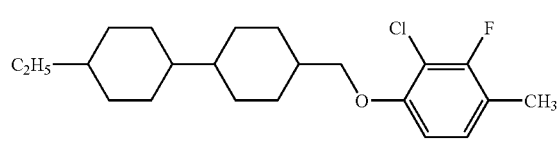
(C247)
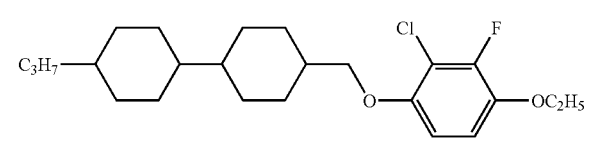
C 84.3 N 151.9 Iso
$T_{NI}$: 137.3° C  $\Delta \epsilon$: -7.54  $\Delta n$: 0.098

-continued
(C248)
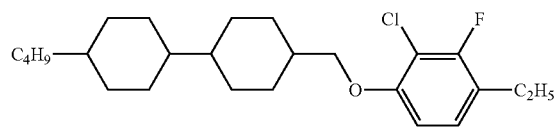
(C249)
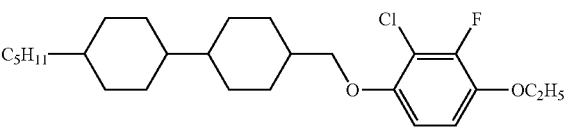
C 77.33 N 152.3 Iso
$T_{NI}$: 142.6° C  Δε: -6.90  Δn: 0.100
(C250)
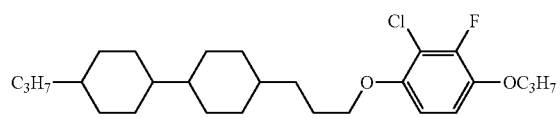
(C251)
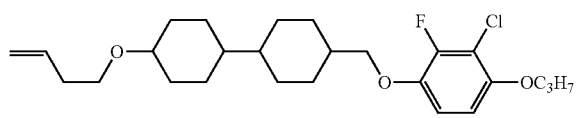
(C252)
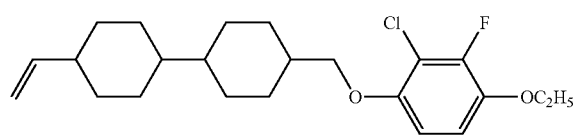
(C253)
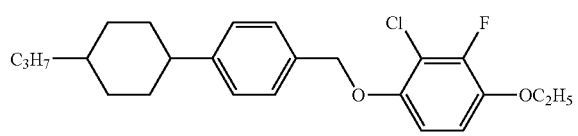
(C254)
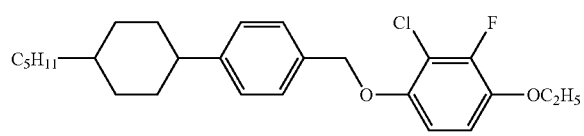
(C255)
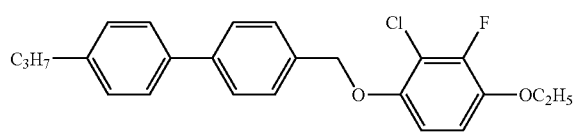
(C256)
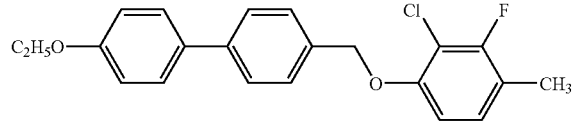
(C257)
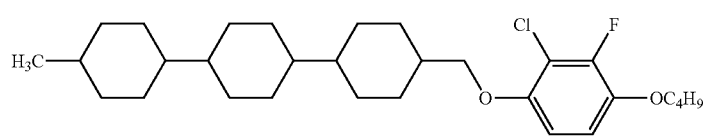
(C258)
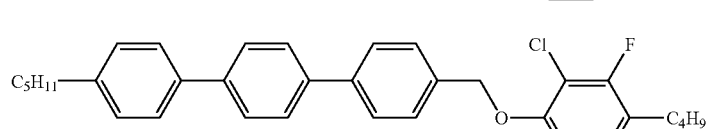
(C259)
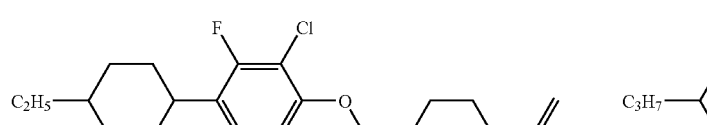
(C260)
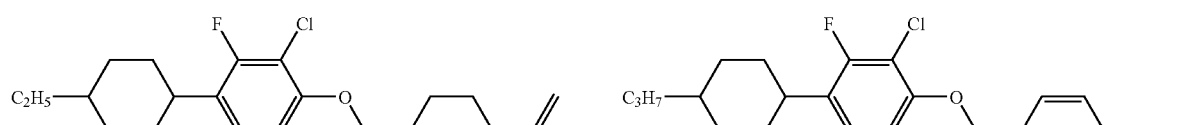
(C261)
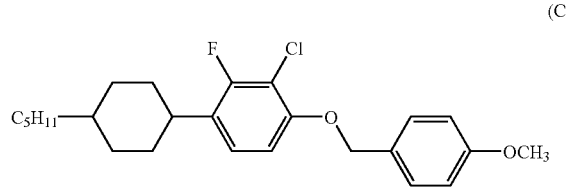
(C262)
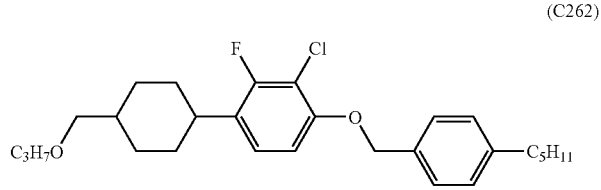

-continued
(C263)
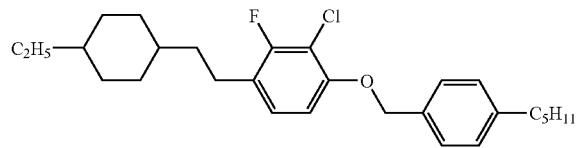
(C264)
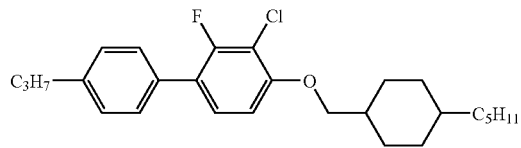
C 79.9 N 110.6 Iso
$T_{NI}$: 108.6° C.  Δ ε: -3.95  Δ n: 0.139
(C265)
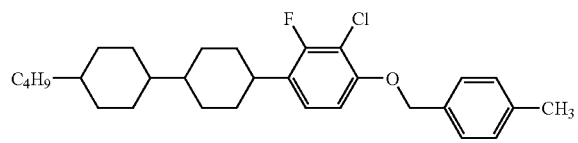
(C266)
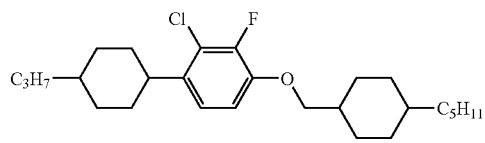
(C267)
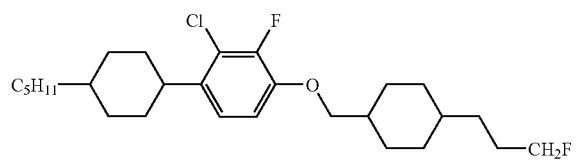
(C268)
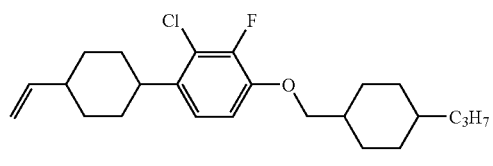
(C269)
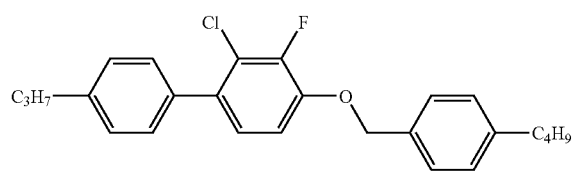
(C270)
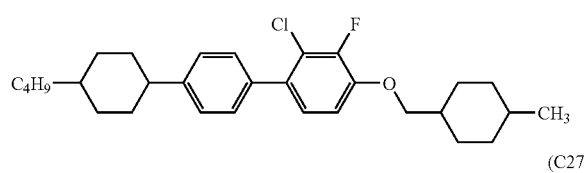
(C271)
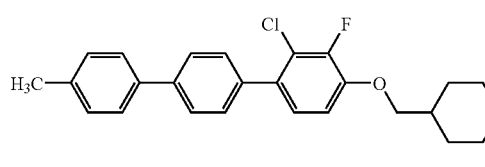
(C273)
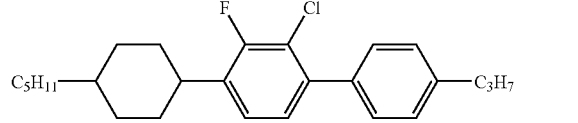
(C274)
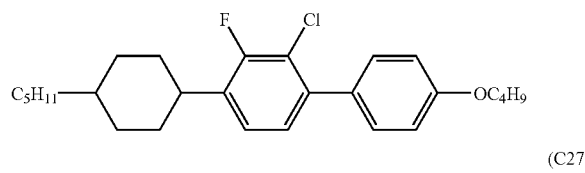
$C_1$ 30.9 $C_2$ 42.1 N 62.3 Iso
$T_{NI}$: 73.3° C.  Δ ε: -1.60  Δ n: 0.12
(C275)
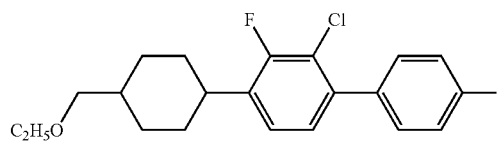
C 98.8 N 124.8 Iso
$T_{NI}$: 113.9° C.  Δ ε: -2..28  Δ n: 0.14
(C276)
(C277)
(C278)
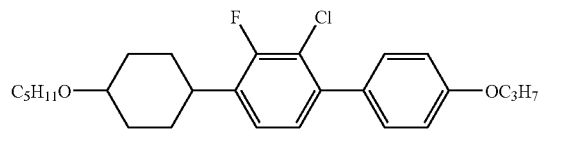
(C279)
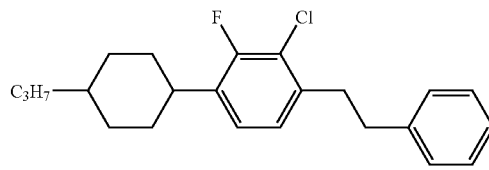

-continued
(C280)
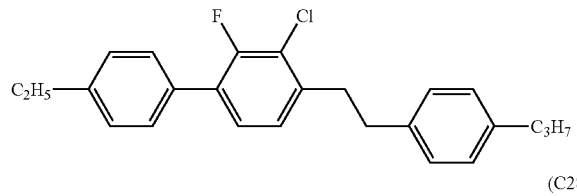
(C281)
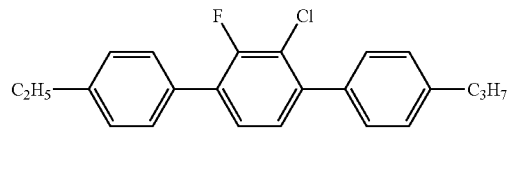
(C282)
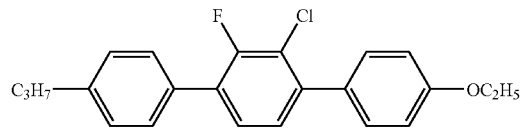
C 116.1 N 130.1 Iso
T$_{NI}$: 108.6° C.  Δ ε: -2.21  Δ n: 0.22
(C283)
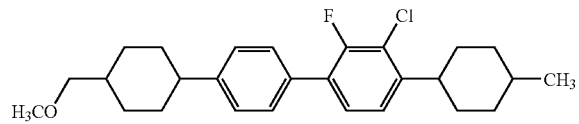
(C284)
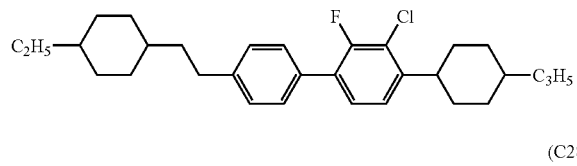
(C285)
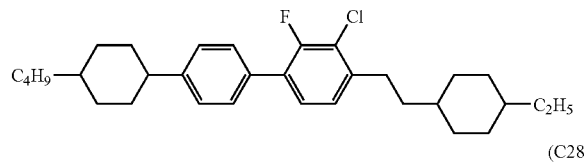
(C286)
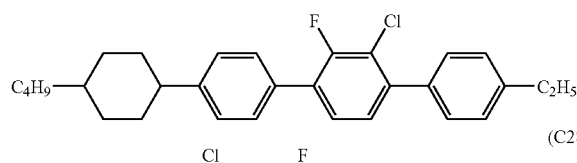
(C287)
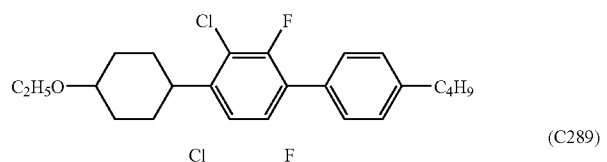
(C288)
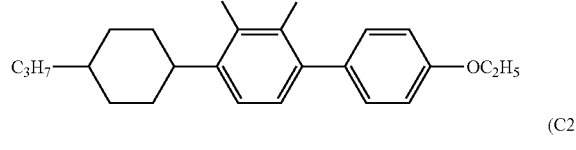
(C289)
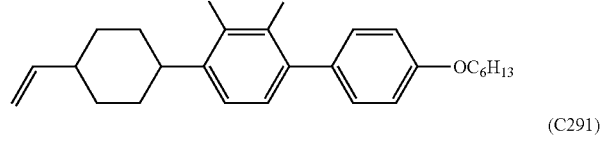
(C290)
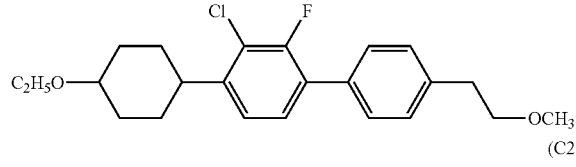
(C291)
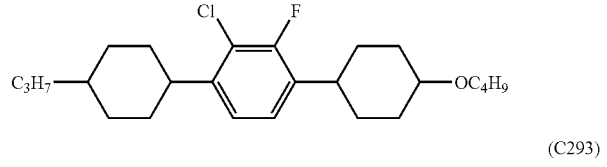
(C292)
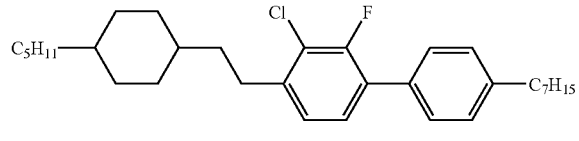
(C293)
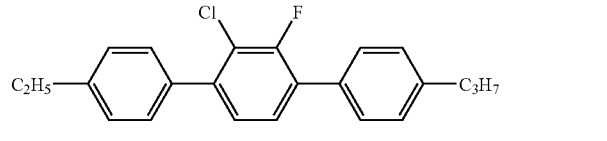
C 83.4 Iso
T$_{NI}$: 47.9° C.  Δ ε: -1.89  Δ n: 0.19
(C294)
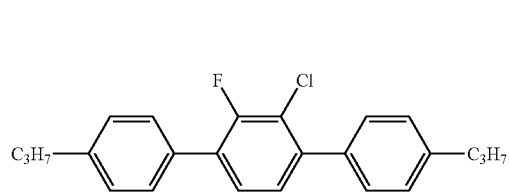
C 69.5 (N 57.9) Iso
T$_{NI}$: 63.9° C.  Δ ε: -1.21  Δ n: 0.20
(C295)
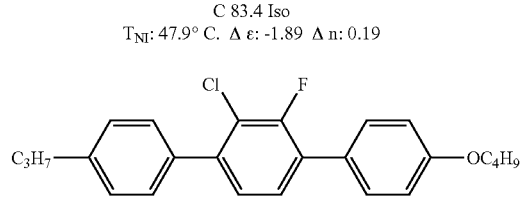
(C296)
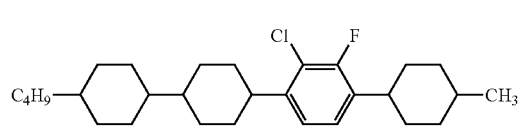
(C297)
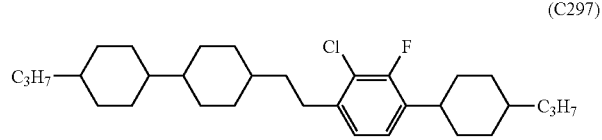

(C298)

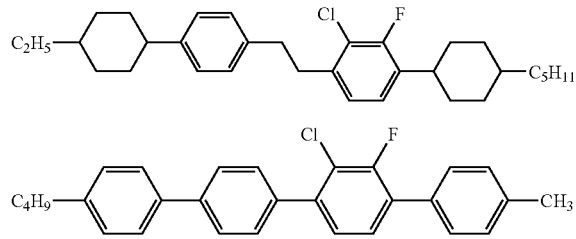

(C299)

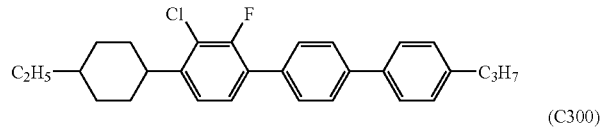

(C300)

Example 15

Characteristics of Liquid Crystal Compound (C28)

The five compounds having been described as the base mixture A were mixed to prepare mother liquid crystal A having a nematic phase. The base mixture A had the following characteristics.

Maximum temperature $(T_{NI})$=74.0° C.; Viscosity $(\eta_{20})$=18.9 mPa·s; Optical anisotropy $(\Delta n)$=0.087; Dielectric anisotropy $(\Delta\varepsilon)$=−1.3

A liquid crystal composition B containing 85% by weight of the base mixture A and 15% by weight of trans-4'-(3-chloro-4-ethoxy-2-fluorophenyl)-trans-4-propyl-bicyclohexyl (C28) obtained in Example 4 was prepared. The characteristics of the liquid crystal composition B were measured, and the characteristics were as follows.

Maximum temperature $(T_{NI})$=85.4° C.; Optical anisotropy $(\Delta n)$=0.090; Dielectric anisotropy $(\Delta\varepsilon)$=−1.97

The liquid crystal composition B was stored at −10° C., and it maintained a nematic phase for 20 days. Since the maximum temperature $(T_{NI})$ was largely increased, and the dielectric anisotropy $(\Delta\varepsilon)$ was negatively increased by adding the liquid crystal compound (C28) to the base mixture A, it was found that the liquid crystal compound (C28) contributed to enhancement of the temperature range of a nematic phase, and a liquid crystal display device having as a constitutional element a liquid crystal composition containing the compound could be driven at a low voltage.

Since the liquid crystal composition B maintained a nematic phase for 20 days even when stored at −10° C., it was found that the liquid crystal compound (C28) was excellent in compatibility at a low temperature.

Example 16

Characteristics of Liquid Crystal Compound (C58)

A liquid crystal composition C containing 85% by weight of the base mixture A described in Example 15 and 15% by weight of trans-4'-(2-(3-chloro-4-ethoxy-2-fluorophenyl)-vinyl)-trans-4-propyl-bicyclohexyl (C58) obtained in Example 6 was prepared. The characteristics of the liquid crystal composition C were measured, and the characteristics were as follows.

Maximum temperature $(T_{NI})$=93.0° C.; Optical anisotropy $(\Delta n)$=0.096; Dielectric anisotropy $(\Delta\varepsilon)$=−2.07

The liquid crystal composition C was stored at −10° C., and it maintained a nematic phase for 30 days. Since the maximum temperature $(T_{NI})$ was largely increased, and the dielectric anisotropy $(\Delta\varepsilon)$ was negatively increased by adding the liquid crystal compound (C58) to the base mixture A, it was found that the liquid crystal compound (C58) contributed to enhancement of the temperature range of a nematic phase, and a liquid crystal display device having as a constitutional element a liquid crystal composition containing the compound could be driven at a low voltage.

Since the liquid crystal composition C maintained a nematic phase for 30 days even when stored at −10° C., it was found that the liquid crystal compound (C58) was excellent in compatibility at a low temperature.

Example 17

Characteristics of Liquid Crystal Compound (C96)

A liquid crystal composition D containing 85% by weight of the base mixture A described in Example 15 and 15% by weight of trans-4'-(2-(2-chloro-4-ethoxy-3-fluorophenyl)-ethyl)-trans-4-propyl-bicyclohexyl (C96) obtained in Example 7 was prepared. The characteristics of the liquid crystal composition D were measured, and the characteristics were as follows.

Maximum temperature $(T_{NI})$=85.1° C.; Optical anisotropy $(\Delta n)$=0.089; Dielectric anisotropy $(\Delta\varepsilon)$=−1.90

The liquid crystal composition D was stored at −10° C., and it maintained a nematic phase for 30 days. Since the maximum temperature $(T_{NI})$ was largely increased, and the dielectric anisotropy $(\Delta\varepsilon)$ was negatively increased by adding the liquid crystal compound (C96) to the base mixture A, it was found that the liquid crystal compound (C96) contributed to enhancement of the temperature range of a nematic phase, and a liquid crystal display device having as a constitutional element a liquid crystal composition containing the compound could be driven at a low voltage.

Since the liquid crystal composition D maintained a nematic phase for 30 days even when stored at −10° C., it was found that the liquid crystal compound (C96) was excellent in compatibility at a low temperature.

Example 18

Characteristics of Liquid Crystal Compound (C116)

A liquid crystal composition E containing 85% by weight of the base mixture A described in Example 15 and 15% by weight of trans-4-(3-chloro-4-ethoxy-2-fluorophenyl)-trans-4'-propenylbicyclohexyl (C116) obtained in Example 14 was prepared. The characteristics of the liquid crystal composition E were measured, and the characteristics were as follows.

Maximum temperature ($T_{NI}$)=87.6° C.; Optical anisotropy ($\Delta n$)=0.092; Dielectric anisotropy ($\Delta \epsilon$)=−2.08

Since the maximum temperature ($T_{NI}$) was largely increased, and the dielectric anisotropy ($\Delta \epsilon$) was negatively increased significantly by adding the liquid crystal compound (C116) to the base mixture A, it was found that the liquid crystal compound (C116) contributed to enhancement of the temperature range of a nematic phase, and a liquid crystal display device having as a constitutional element a liquid crystal composition containing the compound could be driven at a significantly low voltage.

Example 19

Characteristics of liquid crystal compound (C158)

A liquid crystal composition F containing 85% by weight of the base mixture A described in Example 15 and 15% by weight of 4-butoxy-3-chloro-2-fluoro-trans-4'-(trans-4-propylcyclohexyl)biphenyl (C158) obtained in Example 14 was prepared. The characteristics of the liquid crystal composition F were measured, and the characteristics were as follows.

Maximum temperature ($T_{NI}$)=83.3° C.; Optical anisotropy ($\Delta n$)=0.097; Dielectric anisotropy ($\Delta \epsilon$)=−1.95

The liquid crystal composition F was stored at −10° C., and it maintained a nematic phase for 30 days. Since the maximum temperature ($T_{NI}$) was largely increased, and the dielectric anisotropy ($\Delta \epsilon$) was negatively increased by adding the liquid crystal compound (C158) to the base mixture A, it was found that the liquid crystal compound (C158) contributed to enhancement of the temperature range of a nematic phase, and a liquid crystal display device having as a constitutional element a liquid crystal composition containing the compound could be driven at a low voltage.

Since the liquid crystal composition F maintained a nematic phase for 30 days even when stored at −10° C., it was found that the liquid crystal compound (C158) was excellent in compatibility at a low temperature.

Example 20

Characteristics of Liquid Crystal Compound (C247)

A liquid crystal composition G containing 85% by weight of the base mixture A described in Example 15 and 15% by weight of trans-4'-(2-chloro-4-ethoxy-3-fluorophenoxymethyl)-trans-4-propylbicyclohexyl (C247) obtained in Example 14 was prepared. The characteristics of the liquid crystal composition G were measured, and the characteristics were as follows.

Maximum temperature ($T_{NI}$)=84.0° C.; Optical anisotropy ($\Delta n$)=0.089; Dielectric anisotropy ($\Delta \epsilon$)=−2.27

The liquid crystal composition G was stored at −10° C., and it maintained a nematic phase for 30 days. Since the maximum temperature ($T_{NI}$) was largely increased, and the dielectric anisotropy ($\Delta \epsilon$) was negatively increased by adding the liquid crystal compound (C247) to the base mixture A, it was found that the liquid crystal compound (C247) contributed to enhancement of the temperature range of a nematic phase, and a liquid crystal display device having as a constitutional element a liquid crystal composition containing the compound could be driven at a low voltage.

Since the liquid crystal composition G maintained a nematic phase for 30 days even when stored at −10° C., it was found that the liquid crystal compound (C247) was excellent in compatibility at a low temperature.

Comparative Example 1

As a comparative compound 1, trans-4-(2,3-difluoro-4-ethoxyphenyl)-trans-4'-propylbicyclohexyl reported in JP H2-503441 A/1990 (Compound (A) described hereinabove) was synthesized.

A liquid crystal composition H containing 85% by weight of the base mixture A described in Example 15 and 15% by weight of the comparative compound 1 was prepared. The characteristics of the liquid crystal composition H were measured, and the characteristics were as follows.

Maximum temperature ($T_{NI}$)=86.7° C.; Optical anisotropy ($\Delta n$)=0.091; Dielectric anisotropy ($\Delta \epsilon$)=−1.92

The liquid crystal composition H was stored at −10° C., and it was confirmed that crystals were deposited on the seventh day.

Accordingly, it was found from the comparison between the comparative compound 1 and the compound (C28) shown in Example 15 that the compound of the invention is excellent in compatibility at a low temperature although these compounds are equivalent in maximum temperature ($T_{NI}$) and dielectric anisotropy ($\Delta \epsilon$).

Comparative Example 2

As a comparative compound 2, 2-chloro-1-ethoxy-3-fluoro-4-(trans-4-propylcyclohexyl)benzene reported in WO 98/23561 A/1998 was synthesized.

The comparative compound 2 was measured for transition temperature, and it was C 59.4 Iso. It was thus found that the compound did not have a nematic phase as useful characteristics of a compound necessary for a liquid crystal display device.

A liquid crystal composition I containing 85% by weight of the base mixture A described in Example 15 and 15% by weight of the comparative compound 2 was prepared. The characteristics of the liquid crystal composition I were measured, and the characteristics were as follows.

Maximum temperature ($T_{NI}$)=63.5° C.; Optical anisotropy ($\Delta n$)=0.084; Dielectric anisotropy ($\Delta \epsilon$)=−1.98

Since the maximum temperature ($T_{NI}$) was largely decreased by adding the comparative compound 2 to the base mixture A, it was found that the comparative compound 2 did not contribute to enhancement of the temperature range of a nematic phase, and was not a compound capable of deriving characteristics necessary of a liquid crystal display device.

Comparative Example 3

As a comparative compound 3, trans-4-(2,3-dichloro-4-ethoxyphenyl)-trans-4'-propylbicyclohexyl was synthesized.

A liquid crystal composition J containing 85% by weight of the base mixture A described in Example 15 and 15% by weight of the comparative compound 3 was prepared. The characteristics of the liquid crystal composition J were measured, and the characteristics were as follows.

Optical anisotropy ($\Delta n$)=0.088; Dielectric anisotropy ($\Delta \epsilon$)=−1.60

It was found from the comparison between the comparative compound 3 and the compound (C28) shown in Example 15 that the compound of the invention is excellent in dielectric anisotropy.

Comparative Example 4

(Composition K)
The composition K shown below was prepared.

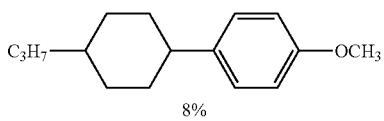
8%

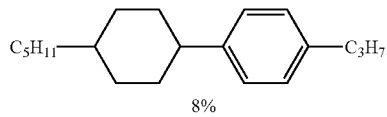
8%

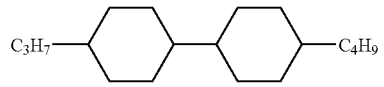
7%

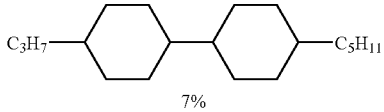
7%

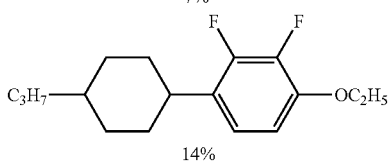
14%

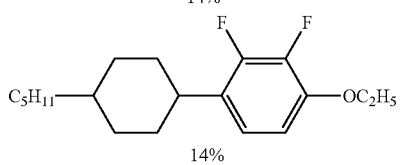
14%

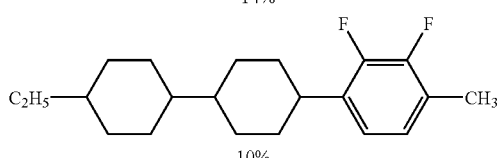
10%

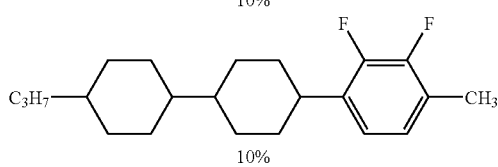
10%

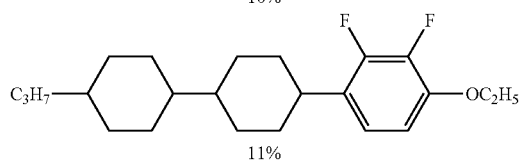
11%

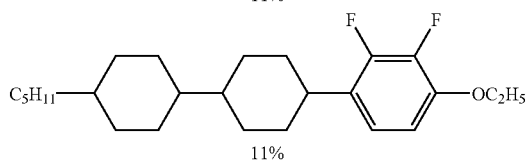
11%

The characteristics of the liquid crystal composition K were measured, and the characteristics were as follows.

Maximum temperature ($T_{NI}$)=68.9° C.; Optical anisotropy ($\Delta n$)=0.081; Dielectric anisotropy ($\Delta\epsilon$)=−3.26

The liquid crystal composition K was stored at temperatures of −10° C. and −20° C. for 30 days, and it was confirmed that crystals were deposited at both temperatures of −10° C. and −20° C.

Example 21

(Composition L)
The composition L shown below was prepared.

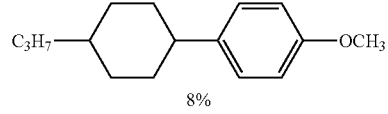
8%

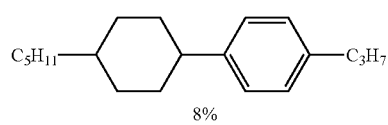
8%

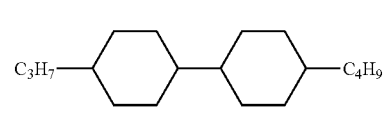
7%

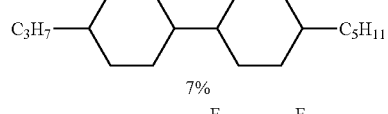
7%

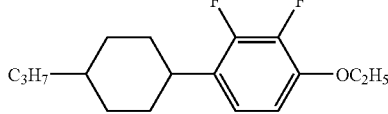
14%

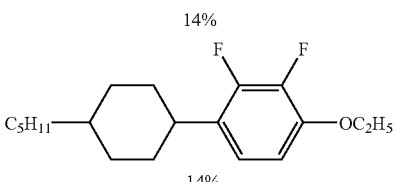
14%

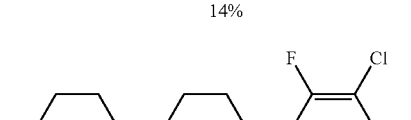 (C21)
10%

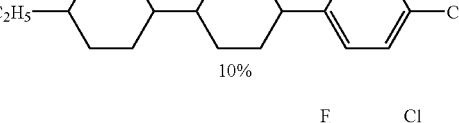 (C22)
10%

-continued

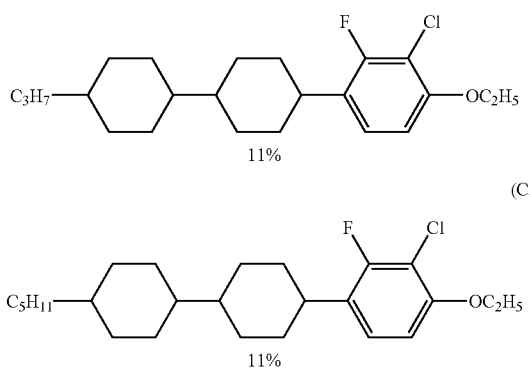

The characteristics of the liquid crystal composition L were measured, and the characteristics were as follows.

Maximum temperature $(T_{NI})$=63.9° C.; Optical anisotropy $(\Delta n)$=0.077; Dielectric anisotropy $(\Delta\varepsilon)$=−3.1

The liquid crystal composition L was stored at temperatures of −10° C. and −20° C. for 30 days, and it was confirmed that crystals were deposited at −20° C., but no crystal was deposited and it maintained a nematic phase at −10° C.

In the liquid crystal composition L, the optical anisotropy ($\Delta n$) could be small, and the minimum temperature of a nematic phase could be enhanced, as compared to the composition K in Comparative Example 4.

Example 22

(Composition M)

The composition M shown below was prepared.

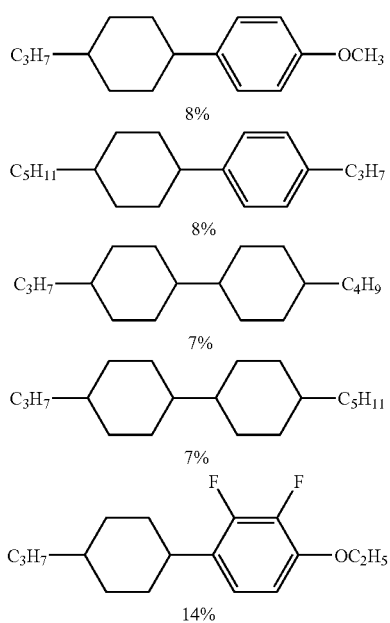

-continued

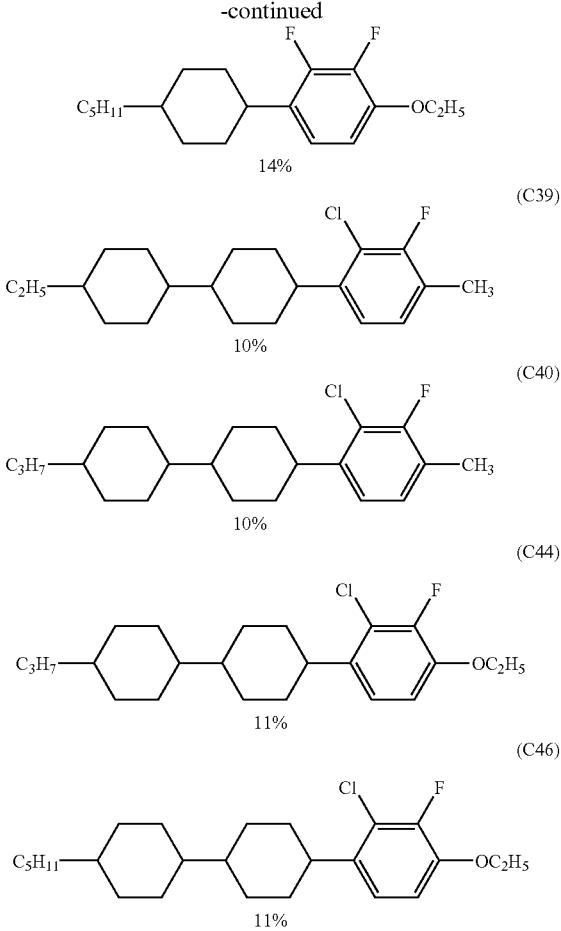

The characteristics of the liquid crystal composition M were measured, and the characteristics were as follows.

Maximum temperature $(T_{NI})$=59.3° C.; Optical anisotropy $(\Delta n)$=0.073; Dielectric anisotropy $(\Delta\varepsilon)$=−3.1

The liquid crystal composition M was stored at temperatures of −10° C. and −20° C. for 30 days, and it was confirmed that no crystal was deposited and it maintained a nematic phase at both temperatures of −20° C. and −10° C.

In the liquid crystal composition L, the optical anisotropy ($\Delta n$) could be small, and the minimum temperature of a nematic phase could be enhanced, as compared to the composition K in Comparative Example 4.

Example 23

(Composition N)

The composition N shown below was prepared.

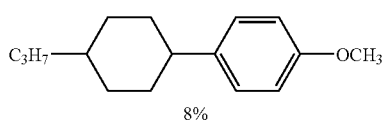

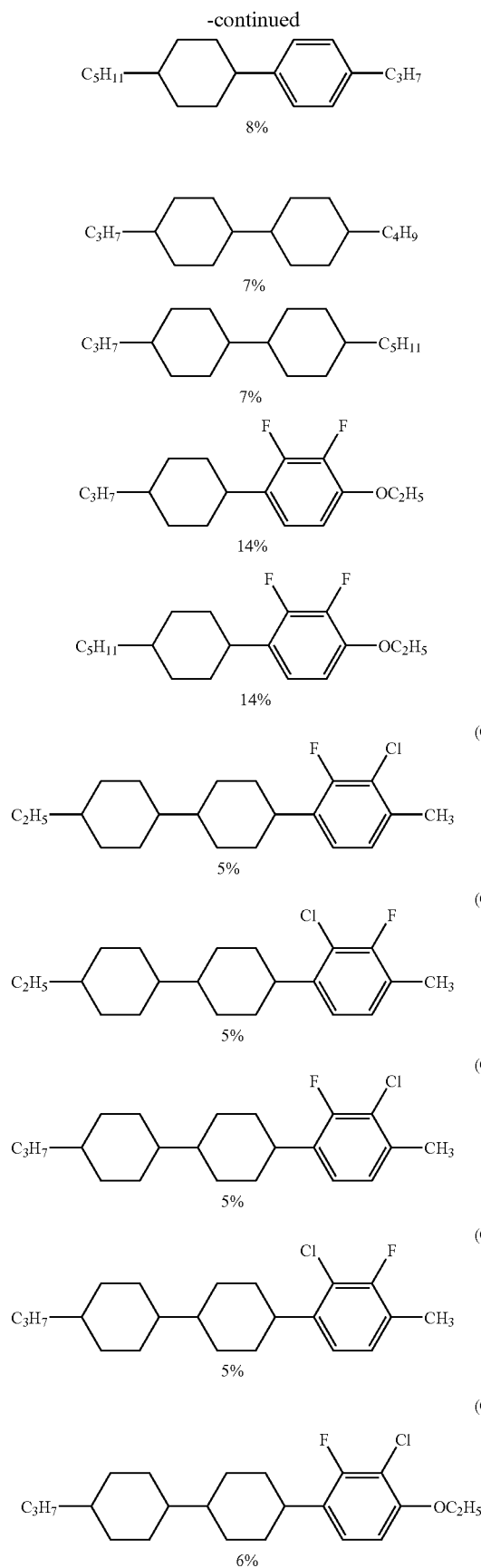

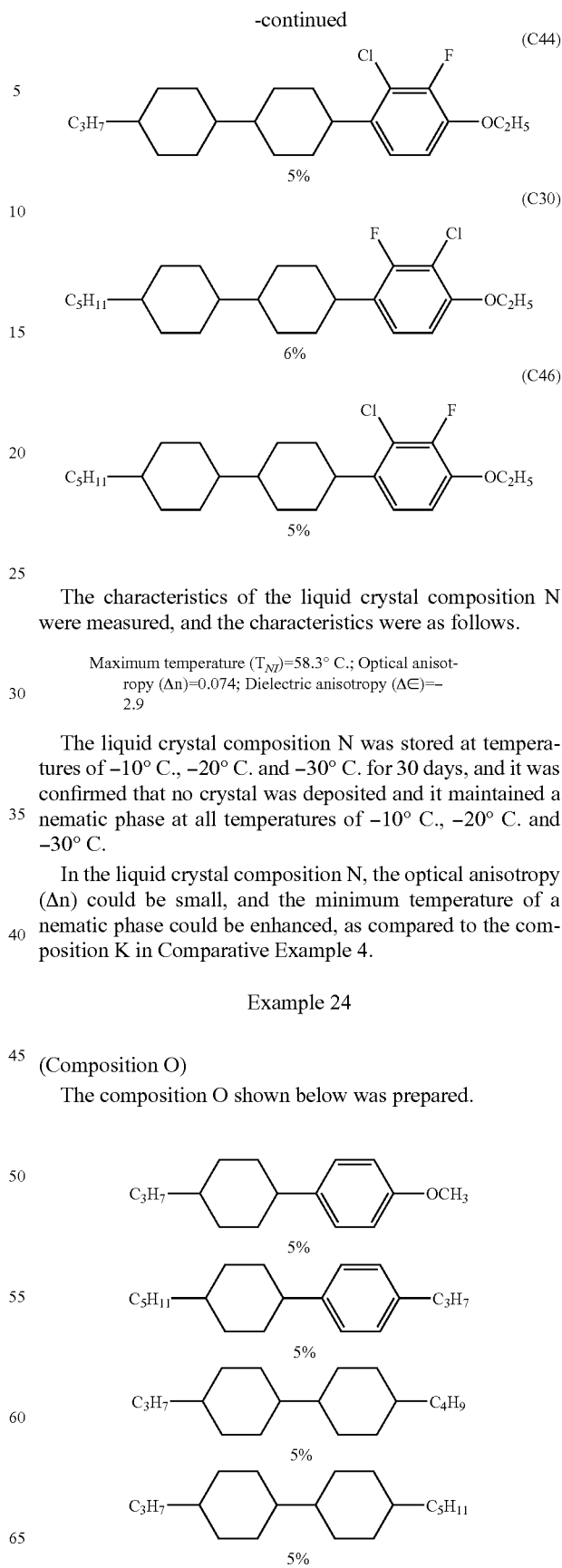

The characteristics of the liquid crystal composition N were measured, and the characteristics were as follows.

Maximum temperature ($T_{NI}$)=58.3° C.; Optical anisotropy ($\Delta n$)=0.074; Dielectric anisotropy ($\Delta\varepsilon$)=−2.9

The liquid crystal composition N was stored at temperatures of −10° C., −20° C. and −30° C. for 30 days, and it was confirmed that no crystal was deposited and it maintained a nematic phase at all temperatures of −10° C., −20° C. and −30° C.

In the liquid crystal composition N, the optical anisotropy ($\Delta n$) could be small, and the minimum temperature of a nematic phase could be enhanced, as compared to the composition K in Comparative Example 4.

Example 24

(Composition O)

The composition O shown below was prepared.

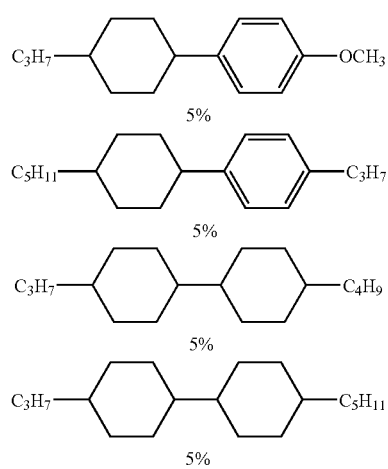

-continued

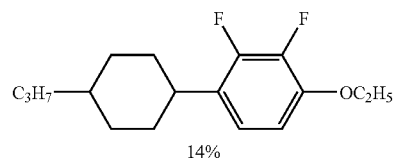
14%

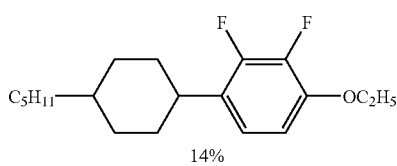
14%

(C21)

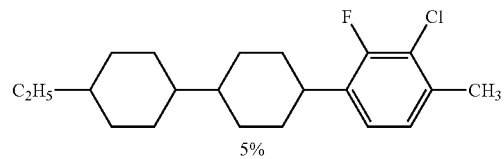
5%

(C39)

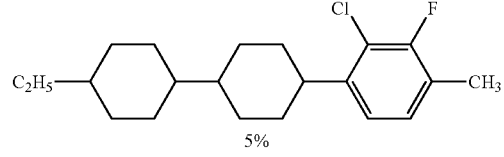
5%

(C22)

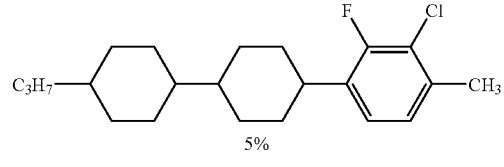
5%

(C40)

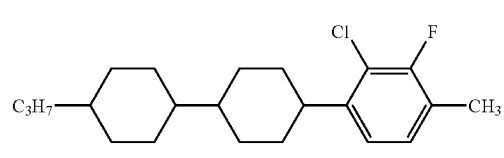
5%

(C28)

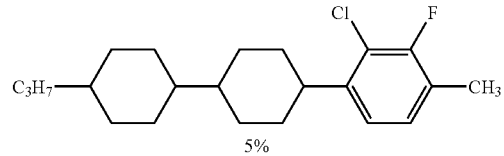
8%

(C44)

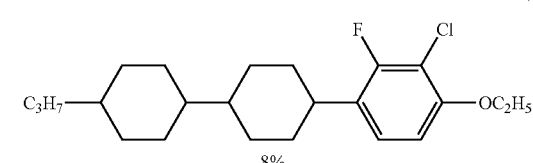
8%

(C30)

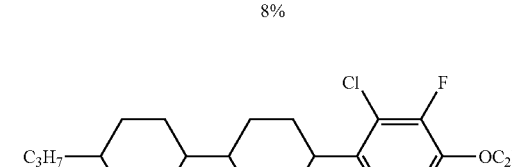
8%

-continued (C46)

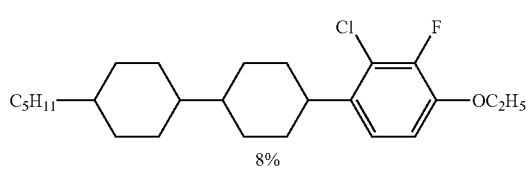
8%

The characteristics of the liquid crystal composition O were measured, and the characteristics were as follows.

Maximum temperature ($T_{NI}$)=70.0° C.; Optical anisotropy (Δn)=0.078; Dielectric anisotropy (Δ∈)=−3.4

The liquid crystal composition O was stored at temperatures of −10° C. and −20° C. for 30 days, and it was confirmed that crystals were deposited at −20° C., but no crystal was deposited and it maintained a nematic phase at −10° C.

In the liquid crystal composition O, the maximum temperature ($T_{NI}$) was high, and the minimum temperature of a nematic phase could be enhanced, as compared to the composition K in Comparative Example 4, and therefore, the liquid crystal composition O could be used in a wide temperature range. In the liquid crystal composition O, the dielectric anisotropy (Δ∈) is negatively large, and a liquid crystal display device having as a constitutional element the liquid crystal composition could be driven at a low voltage.

What is claimed is:

1. A liquid crystal compound represented by one of formulas (a) to (d):

(a)

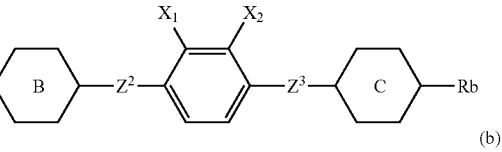

(b)

(c)

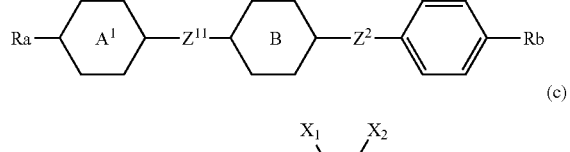

(d)

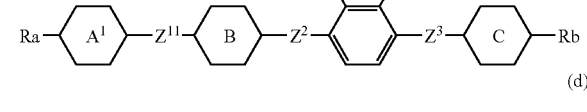

wherein Ra and Rb are independently hydrogen or linear alkyl having 1 to 10 carbons, provided that in the alkyl, —CH$_2$— may be replaced by —O—, —(CH$_2$)$_2$— may be replaced by —CH=CH—, and hydrogen may be replaced by a halogen; rings $A^1$, $A^2$, B and C are independently trans-1,4-cyclohexylene or 1,4-phenylene; $Z^{11}$, $Z^{12}$, $Z^2$ and $Z^3$ are independently a single bond or alkylene having 2 or 4 carbons, provided that in the alkylene, —CH$_2$— may be replaced by —O— and —(CH$_2$)$_2$— may be replaced by —CH=CH—; and X$_1$ is fluorine, and X$_2$ is chlorine, provided that:

in a case where:
in formula (a), rings B and C are trans-1,4-cyclohexylene, and Z$^2$ and Z$^3$ are a single bond,
in formula (b), rings A$^1$ and B are trans-1,4-cyclohexylene, Z$^{11}$ is a single bond, and Z$^2$ is —CH$_2$O—,
and
in formula (d), rings A$^1$, A$^2$ and B are trans-1,4-cyclohexylene, Z$^{11}$ and Z$^{12}$ are a single bond, and Z$^2$ is a single bond or —CH$_2$O—,
Rb is one of linear alkoxy having 1 to 9 carbons, linear alkoxyalkyl having 2 to 9 carbons, linear alkenyl having 2 to 10 carbons, linear alkenyloxy having 2 to 9 carbons.

2. A liquid crystal compound represented by one of formulas (a-1) to (d-1):

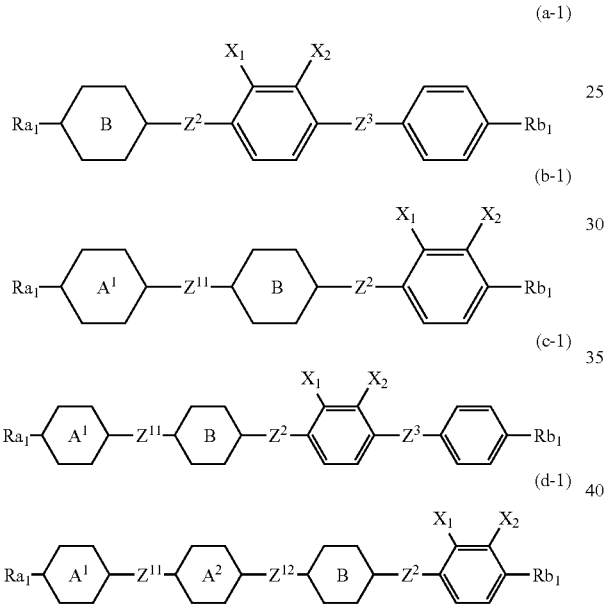

wherein Ra$_1$ and Rb$_1$ are independently linear alkyl having 1 to 10 carbons, provided that in the alkyl, —CH$_2$— may be replaced by —O—, —(CH$_2$)$_2$— may be replaced by —CH=CH—; rings A$^1$, A$^2$ and B are independently trans-1,4-cyclohexylene or 1,4-phenylene; Z$^{11}$, Z$^{12}$, Z$^2$ and Z$^3$ are independently a single bond or alkylene having 2 or 4 carbons, provided that in the alkylene, —CH$_2$— may be replaced by —O— and —(CH$_2$)$_2$— may be replaced by —CH=CH—; and X$_1$ is fluorine, and X$_2$ is chlorine, provided that:

in a case where:
in formula (b-1), rings A$^1$ and B are trans-1,4-cyclohexylene, Z$^{11}$ is a single bond, and Z$^2$ is —CH$_2$O—, and
in formula (d-1), rings A$^1$, A$^2$ and B are trans-1,4-cyclohexylene, Z$^{11}$ and Z$^{12}$ are a single bond, and Z$^2$ is a single bond or —CH$_2$O—,
Rb$_1$ is one of linear alkoxy having 1 to 9 carbons, linear alkoxyalkyl having 2 to 9 carbons, linear alkenyl having 2 to 10 carbons, and linear alkenyloxy having 2 to 9 carbons.

3. A liquid crystal compound represented by one of formulas (b-2-2) to (b-7-2):

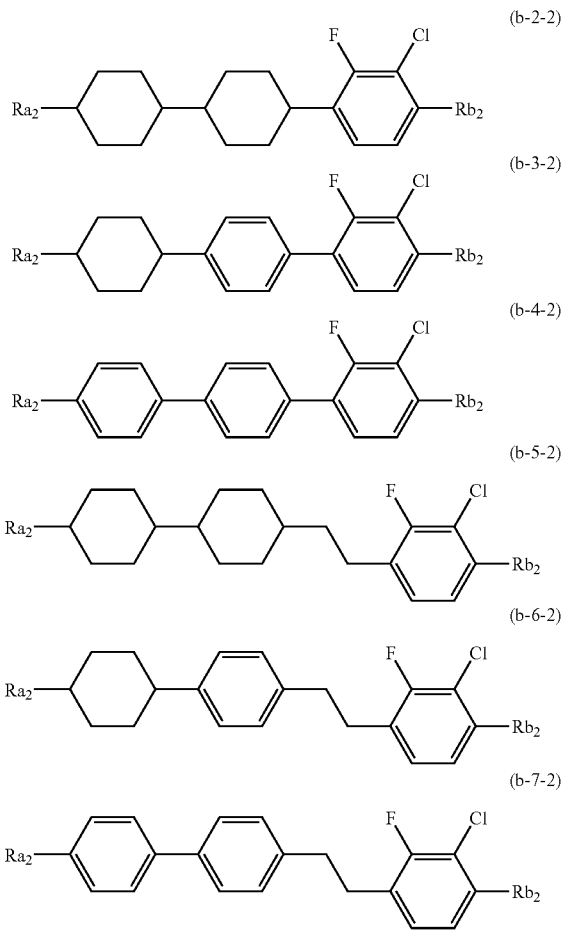

wherein Ra$_2$ is linear alkyl having 1 to 10 carbons or linear alkenyl having 2 to 10 carbons, Rb$_2$ is linear alkyl having 1 to 10 carbons or linear alkoxy having 1 to 9 carbons, and the cyclohexylene ring is trans-1,4-cyclohexylene.

4. The liquid crystal compound according to claim 3, wherein the compound represented by one of formulas (b-2-2) to (b-7-2), wherein Ra$_2$ is linear alkyl having 1 to 10 carbons, and Rb$_2$ is linear alkoxy having 1 to 9 carbons.

5. A liquid crystal compound represented by one of formulas (b-8-2) to (b-10-2):

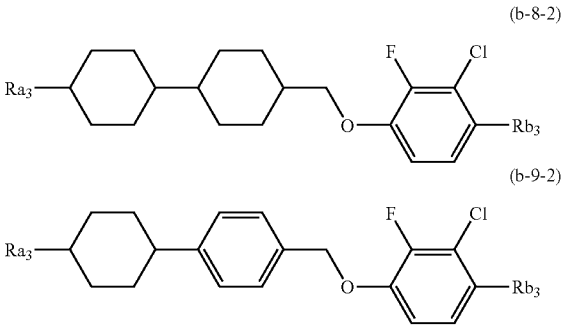

(b-10-2)

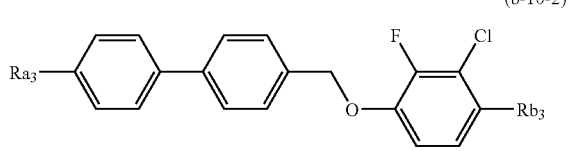

wherein Ra₃ is linear alkyl having 1 to 10 carbons or linear alkenyl having 2 to 10 carbons, Rb₃ is linear alkoxy having 1 to 9 carbons, and the cyclohexylene ring is trans-1,4-cyclohexylene.

6. The liquid crystal compound according to claim 5, wherein the compound represented by one of formulas (b-8-2) to (b-10-2), wherein Ra₃ is linear alkyl having 1 to 10 carbons.

7. A liquid crystal composition comprising the liquid crystal compound according to claim 1.

8. A liquid crystal display device comprising a liquid crystal composition comprising the liquid crystal compound according to claim 1.

9. A liquid crystal compound represented by one of formulas (a-2) to (d-2):

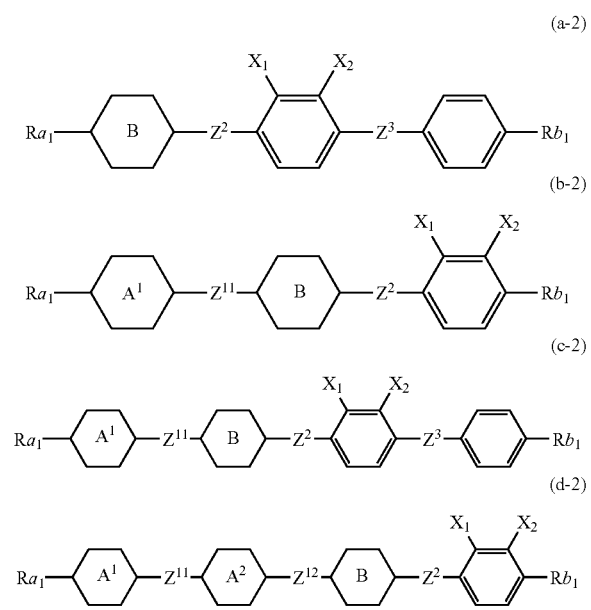

wherein Ra₁ and Rb₁ are independently linear alkyl having 1 to 10 carbons, provided that in the alkyl, —CH₂— may be replaced by —O—, —(CH₂)₂— may be replaced by —CH=CH—; rings A¹, A² and B are independently trans-1,4-cyclohexylene or 1,4-phenylene; Z¹¹ is a single bond or —(CH₂)₂—, and Z¹², Z² and Z³ are independently a single bond or alkylene having 2 or 4 carbons, provided that in the alkylene, —CH₂— may be replaced by —O— and —(CH₂)₂— may be replaced by —CH=CH—; and X₁ is fluorine, and X₂ is chlorine, provided that:

in a case where:
in formula (b-2), rings A¹ and B are trans-1,4-cyclohexylene, Z¹¹ is a single bond, and Z² is —CH₂O—, and
in formula (d-2), rings A¹, A² and B are trans-1,4-cyclohexylene, Z¹¹ and Z¹² are a single bond, and Z² is a single bond or —CH₂O—,
Rb₁ is one of linear alkoxy having 1 to 9 carbons, linear alkoxyalkyl having 2 to 9 carbons, linear alkenyl having 2 to 10 carbons, and linear alkenyloxy having 2 to 9 carbons.

10. The liquid crystal compound according to claim 9, wherein the compound represented by formula (a-2) or (b-2), wherein Ra₁ and Rb₁ are independently linear alkyl having 1 to 10 carbons, linear alkoxy having 1 to 9 carbons, linear alkoxyalkyl having 1 to 9 carbons, linear alkenyl having 2 to 10 carbons, or linear alkenyloxy having 2 to 9 carbons, Z¹¹ is a single bond or —(CH₂)₂— and Z¹², Z² and Z³ are independently a single bond, —(CH₂)₂—, —CH=CH—, —CH₂O— or —OCH₂—.

11. The liquid crystal compound according to claim 9, wherein the compound represented by formula (c-2) or (d-2), wherein Ra₁, and Rb₁ are independently linear alkyl having 1 to 10 carbons, linear alkoxy having 1 to 9 carbons, linear alkoxyalkyl having 1 to 9 carbons, or linear alkenyl having 2 to 10 carbons, and
Z¹¹ is a single bond or —(CH₂)₂— and Z¹², Z² and Z³ are independently a single bond, —(CH₂)₂—, —CH=CH—, —CH₂O— or —OCH₂—.

12. The liquid crystal compound according to claim 9, wherein the compound represented by one of formulas (a-2) to (d-2), wherein Ra₁ is linear alkyl having 1 to 10 carbons or linear alkenyl having 2 to 10 carbons, Rb₁ is linear alkyl having 1 to 10 carbons or linear alkoxy having 1 to 9 carbons;
Z¹¹ is a single bond or —(CH₂)₂— and Z¹², Z² and Z³ are independently a single bond, —(CH₂)₂—, —CH=CH—, —CH₂O— or —OCH₂—.

13. The liquid crystal compound according to claim 9, wherein the compound represented by one of formulas (a-2) to (d-2), wherein Z¹¹ is a single bond or —(CH₂)₂— and Z¹², Z² and Z³ are independently a single bond, —(CH₂)₂— or —CH=CH—.

14. The liquid crystal compound according to claim 9, wherein the compound represented by one of formulas (a-2) to (d-2), wherein Ra₁ is linear alkyl having 1 to 10 carbons or linear alkenyl having 2 to 10 carbons, Rb₁ is linear alkoxy having 1 to 9 carbons, Z¹¹ is a single bond or —(CH₂)₂— and Z¹² and Z³ are independently a single bond, —(CH₂)₂—, —CH=CH—, —CH₂O— or —OCH₂—, and Z² is —CH₂O—.

* * * * *